(12) United States Patent
Edwards et al.

(10) Patent No.: US 6,534,516 B1
(45) Date of Patent: Mar. 18, 2003

(54) ANDROGEN RECEPTOR MODULATOR COMPOUNDS AND METHODS

(75) Inventors: James P Edwards, San Diego; Robert Higuchi; Todd K Jones, both of Solana Beach; Lawrence G Hamann, San Diego, all of CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 0 days.

(21) Appl. No.: 09/448,992

(22) Filed: Nov. 24, 1999

Related U.S. Application Data

(60) Division of application No. 09/373,460, filed on Aug. 12, 1999, now Pat. No. 6,017,924, which is a continuation-in-part of application No. 08/883,115, filed on Jun. 26, 1997, now abandoned.
(60) Provisional application No. 60/021,997, filed on Jun. 27, 1996.

(51) Int. Cl.$^7$ .................... C07D 487/04; C07D 491/06; A61K 31/4738

(52) U.S. Cl. .......................................... 514/285; 546/70

(58) Field of Search .............................. 546/70; 514/285

(56) References Cited

U.S. PATENT DOCUMENTS

| | | | |
|---|---|---|---|
| 3,331,846 A | 7/1967 | Easton et al. ............... | 260/280 |
| 3,798,031 A | 3/1974 | Janssens et al. ............. | 96/1.8 |
| 3,830,647 A | 8/1974 | Janssens et al. ............. | 96/1.5 |
| 3,832,171 A | 8/1974 | Janssens et al. ............. | 96/1.5 |
| 3,928,686 A | 12/1975 | Poot et al. .................. | 428/457 |
| 3,979,394 A | 9/1976 | Janssens et al. ...... | 260/283 BZ |
| 4,594,179 A * | 6/1986 | Harrah et al. .......... | 252/301.17 |
| 4,736,032 A * | 4/1988 | Fox et al. ..................... | 546/66 |
| 4,891,352 A * | 1/1990 | Byers ........................ | 503/227 |
| 4,943,502 A | 7/1990 | Terrell et al. ................. | 430/58 |
| 4,981,784 A | 1/1991 | Evans et al. .................... | 435/6 |
| 5,071,773 A | 12/1991 | Evans et al. ................. | 436/501 |
| 5,147,844 A | 9/1992 | Weber et al. ............... | 503/227 |
| 5,696,130 A | 12/1997 | Jones et al. | |

FOREIGN PATENT DOCUMENTS

| | | | |
|---|---|---|---|
| SU | 555119 | | 6/1977 |
| WO | WO 88/04850 | * | 6/1988 |
| WO | WO 91/00732 A1 | | 1/1991 |
| WO | WO 95/11215 A1 | | 4/1995 |
| WO | WO 96/19458 A2 | | 6/1996 |
| WO | 96/19458 | | 6/1996 |

OTHER PUBLICATIONS

Harrah et al., Chem. Abstract 103: 185647, 1985.*
Hollins et al., Chem. Abstract 109:160267, 1988.*
Byers, Chem. Abstract 113:99588, 1990.*
Atkins, et al., "Substituted Coumarins and Azacoumarins. Synthesis and Fluoresent Properties," *J. Org. Chem.*, 43:1975–1980 (1978).
Berger, et al., "Interaction of Glucocorticoid Analogues with the Human Glucocorticoid Receptor," *J. Steriod Biochem. Mol. Biol.*, 41:733–738 (1992).
Bissell, et al., "Synthesis and Chemistry of 7–amino–4–(trifluoromethyl)coumarin and Its Amino Acid and Peptide Deriviatives," *J. Org. Chem*, 45:2283–2287 (1980).
Catterall, et al., "Regulation of Gene Expression and Androgens in Murine Kidney," *Recent Prog. Horm. Res.*, 42:71–109 (1986).
Damassa, et al., "Negative Feedback Control of LH by Testosterone: A Quantitative Study in Male Rats," *Endocrinology*, 99:736–742 (1976).
Djurhuus, R., "Ornithine Decarboxylase (EC 4.1.1.17) Assay Based upon the Retention of Putrecine by a Strong Cation–Exchange Paper," *Anal. Biochem.*, 113:352–355 (1981).
Dziuk, et al., "Passage of Steriods Through Silicone Rubber," *Endocrinology*, 78:208–211 (1966).
Easton, et al., "A Novel Synthesis of Quinolines and Dihydroquinolines," *J. Org. Chem*, 27:4713–4714 (1962).
Evans, et al., "The Steriod and Thyroid Hormone Receptor Superfamily," *Science*, 240:889–95 (1988).
Furr, et al., "A Novel Non–steriodal, Peripherally Selective Antiandrogen," *J. Endocrinology*, 113:R7–R9 (1987).
Gromova, et al., "Relative volatility of stabilizers for polymer materials," *Khim. Prom.st.*, 43:97 (Moscow, 1967).
Hershberger, et al., "Myotropic Activity of 19–Nortestosterone and Other Steriods Determined by Modified Levator Ani Muscle Method," *Proc. Soc. Exp. Biol. Med.*, 83:175–180 (1953).
Imada, et al., "Copper(I)–Catalyzed Amination of Propargyl Esters. Selective Synthesis of Proparagylamines, 1–Alken–3–ylamines, and (Z)–Allylamines," *J. Org. Chem.*, 59:2282–2284.
Janne, et al., "Ornithine Decarboxylase mRNA in Mouse Kidney: A Low Abundancy Gene Product Regulated by Androgens with Rapid Kinetics$^a$," *Ann. N. Y. Acad. Sci.*, 438:72–84 (1984).
Jones, G., *Comprehensive Heterocyclic Chemistry*, Katrizky and Rees Eds. Pergamon, NY (1984), V.2, Chap. 2.08:421–426.

(List continued on next page.)

Primary Examiner—Deepak R. Rao
(74) Attorney, Agent, or Firm—Brobeck, Phleger & Harrison LLP

(57) ABSTRACT

Non-steroidal compounds that are high affinity, high selectivity modulators for androgen receptors are disclosed. Also disclosed are pharmaceutical compositions incorporating such compounds, methods for employing the disclosed compounds and compositions for treating patients requiring androgen receptor agonist, partial agonist or antagonist therapy, intermediates useful in the preparation of the compounds and processes for the preparation of the androgen receptor modulator compounds.

18 Claims, No Drawings

OTHER PUBLICATIONS

Labrie, et al., "Science behind total androgen blockade: from gene therapy to combination therapy," *Clin. Invest. Med.*, 16:475–492 (1993).

Lucky, et al., "Hair Follicle Response of the Golden Syrian Hamster Flank Organ to Continuous Testosterone Stimulation Using Silastic Capsules," *J. Invest. Dermatol.*, 86:83–86.

Lucky, et al., "Hair Follicle Response of the Golden Syrian Hamster Flank Organ to Continous Testosterone Stimulation Using Silastic Capsules," *J. Invest. Dermatol.*, 86:83–86, 1986.

Luke, et al., "The Male Sex Accessory Tissues; Structure, Androgen Action; and Physiology," *The Physiology of Reproduction*, Knobil and Neill, Eds., 1:1435–1487 (1994).

Manske, et al., "The Skraup Synthesis of Quinolines," *Organic Reactions*, 7:59–98 (1953).

McBee, et al., "The Preparation and Reactions of Fluorine–containing Acetoacetic Esters," *J. Am. Chem. Soc.*, 75:3152–3153 (1953).

Okuda, et al., "Testosterone Dependent Regulation of the Enzymes involved in DNA Synthesis in the Rat Ventral Prostate," *J. Urol.*, 145:188–91 (1991).

Scalabrino, et al., "Polyamines and mammalian hormones. Part 1: Biosynthesis, interconversion and hormone effects," *Mol. Cell. Endocrinol.*, 77:1–35 (1991).

Simental, et al., Transcriptional Activation and Nuclear Targeting Signals of the Human Androgen Receptor, *J. Biol Chem.*, 266:510–518 (1991).

Walsh, et al., "Inhibition of Extratesticular Stimuli to Prostatic Growth in the Castrate Rat by Antiandrogens," *Endocrinology*, 87:624–627 (1970).

Langden, J. et al., "Mathematics and Statistics of Ligand Assays: An Illustrated Guide," Ligand Assay, Masson Publishing, NY 45–99 (1981).

Seeman, PubMed Abstract (Rev. Endocr. Metab. Disord., 2(1):45–64), Jan. 2001.*

Dobs, PubMed Abstract (Baillieres Clin. Endocrinol. Metab., 12(3):379–90), Oct. 1998.*

Mulligan et al., PubMed Abstract (JPEN J. Parenter Enteral Nutr., 23(6 Suppl):S202–9), Nov.–Dec., 1999.*

Bhasin et al., Emerging Issues in Androgen Replacement Therapy, Journal of Clinical Endocrinology and Metabolism, vol. 82, No. 1, pp. 3–8, 1997.*

Simone, Oncology: Introduction, Cecil Textbook of Medicine, 20$^{th}$ Edition, vol. 1, pp. 1004–10, 1996.*

Rittmaster, Hirsutism, Cecil Textbook of Medicine, 20$^{th}$ Edition, vol. 2, pp. 1315–7, 1996.*

Nadzan, et al., "Nybomycin. 8. Biosynthetic Origin of the Central Ring Carbons Studied by $^{13}$C–Labeled Substrates[1,2], " *Journal of the American Chemical Society*, 98(16):5012–5014 (1976).

* cited by examiner

ANDROGEN RECEPTOR MODULATOR COMPOUNDS AND METHODS

RELATED APPLICATIONS

This application is a Divisional of Ser. No. 09/373,460 filed Aug. 12, 1999 now U.S. Pat. No. 6,017,924 which is a continuation-in part of U.S. application Ser. No. 08/883,115 filed Jun. 26, 1997 now abandoned, which claims the benefit of U.S. Provisional Application No. 60/021,997, filed Jun. 27, 1996.

FIELD OF THE INVENTION

This invention relates to non-steroidal compounds that are modulators (i.e. agonists and antagonists) of androgen receptors, and to methods for the making and use of such compounds.

BACKGROUND OF THE INVENTION

Intracellular receptors (IRs) form a class of structurally-related genetic regulators scientists have named "ligand dependent transcription factors." R. M. Evans, 240 *Science*, 889 (1988). Steroid receptors are a recognized subset of the IRs, including the progesterone receptor (PR), androgen receptor (AR), estrogen receptor (ER), glucocorticoid receptor (GR) and mineralocorticoid receptor (MR). Regulation of a gene by such factors requires both the IR itself and a corresponding ligand that has the ability to selectively bind to the IR in a way that affects gene transcription.

Ligands to the IRs can include low molecular weight native molecules, such as the hormones progesterone, estrogen and testosterone, as well as synthetic derivative compounds such as medroxyprogesterone acetate, diethylstilbesterol and 19-nortestosterone. These ligands, when present in the fluid surrounding a cell, pass through the outer cell membrane by passive diffusion and bind to specific IR proteins to create a ligand/receptor complex. This complex then translocates to the cell's nucleus, where it binds to a specific gene or genes present in the cell's DNA. Once bound to DNA, the complex modulates the production of the protein encoded by that gene. In this regard, a compound that binds an IR and mimics the effect of the native ligand is referred to as an "agonist", while a compound that inhibits the effect of the native ligand is called an "antagonist."

Ligands to the steroid receptors are known to play an important role in health of both women and men. For example, the native female ligand, progesterone, as well as synthetic analogues, such as norgestrel (18-homonorethisterone) and norethisterone (17α-ethinyl-19-nortestosterone), are used in birth control formulations, typically in combination with the female hormone estrogen or synthetic estrogen analogues, as effective modulators of both PR and ER. On the other hand, antagonists to PR are potentially useful in treating chronic disorders, such as certain hormone dependent cancers of the breast, ovaries, and uterus, and in treating non-malignant conditions such as uterine fibroids and endometriosis, a leading cause of infertility in women. Similarly, AR antagonists, such as cyproterone acetate and flutamide have proved useful in the treatment of prostatic hyperplasia and cancer of the prostate.

The effectiveness of known modulators of steroid receptors is often tempered by their undesired side-effect profile, particularly during long-term administration. For example, the effectiveness of progesterone and estrogen agonists, such as norgestrel and diethylstilbesterol respectively, as female birth control agents must be weighed against the increased risk of breast cancer and heart disease to women taking such agents. Similarly, the progesterone antagonist, mifepristone (RU486), if administered for chronic indications, such as uterine fibroids, endometriosis and certain hormone-dependent cancers, could lead to homeostatic imbalances in a patient due to its inherent cross-reactivity as a GR antagonist. Accordingly, identification of compounds which have good specificity for one or more steroid receptors, but which have reduced or no cross-reactivity for other steroid or intracellular receptors, would be of significant value in the treatment of male and female hormone responsive diseases.

A group of quinoline analogs having an adjacent polynucleic ring system of the indene or fluorene series or an adjacent polynucleic heterocyclic ring system with substituents having a nonionic character have been described as photoconductive reducing agents, stabilizers, laser dyes and antioxidants. See e.g., U.S. Pat. Nos. 3,798,031; 3,830,647; 3,832,171; 3,928,686; 3,979,394; 4,943,502 and 5,147,844 as well as Soviet Patent No. 555,119; R. L. Atkins and D. E. Bliss, "Substituted Coumarins and Azacoumarins: Synthesis and Fluorescent Properties", 43 *J. Org. Chem.*, 1975 (1978), E. R. Bissell et al., "Synthesis and Chemistry of 7-Amino-4-(trifluoromethyl)coumarin and Its Amino Acid and Peptide Derivatives", 45 *J. Org. Chem.*, 2283 (1980) and G. N. Gromova and K. B. Piotrovskii, "Relative Volatility of Stabilizers for Polymer Materials," 43 *Khim. Prom-st.*, 97 (Moscow, 1967). Further, a group of quinoline derivatives was recently described as modulators of steroid receptors. WO 96/19458, published Jun. 27, 1996.

SUMMARY OF THE INVENTION

The present invention is directed to compounds, pharmaceutical compositions, and methods for modulating processes mediated by androgen receptors (AR). More particularly, the invention relates to non-steroidal compounds and compositions which are high affinity, high specificity agonists, partial agonists (i.e., partial activators and/or tissue-specific activators) and antagonists for androgen receptors. Also provided are methods of making such compounds and pharmaceutical compositions, as well as critical intermediates used in their synthesis.

These and various other advantages and features of novelty that characterize the invention are pointed out with particularity in the claims annexed hereto and forming a part hereof. However, for a better understanding of the invention, its advantages, and objects obtained by its use, reference should be had to the accompanying descriptive matter, in which preferred embodiments of the invention are described.

DEFINITIONS AND NOMENCLATURE

As used herein, the following terms are defined with the following meanings, unless explicitly stated otherwise. Furthermore, in an effort to maintain consistency in the naming of compounds of similar structure but differing substituents, the compounds described herein are named according to the following general guidelines. The numbering system for the location of substituents on such compounds is also provided.

The term alkyl, alkenyl, alkynyl and allyl includes straight-chain, branched-chain, cyclic, saturated and/or unsaturated structures, and combinations thereof.

The term aryl refers to an optionally substituted six-membered aromatic ring, including polyaromatic rings and polycyclic ring systems of from two to four, more preferably two to three, and most preferably two rings.

The term heteroaryl refers to an optionally substituted five-membered heterocyclic ring containing one or more heteroatoms selected from the group consisting of carbon, oxygen, nitrogen and sulfur, including polycyclic rings of from two to four, more preferably two to three, and most preferably two rings, or a six-membered heterocyclic ring containing one or more heteroatoms selected from the group consisting of carbon and nitrogen, including polycyclic rings of from two to four, more preferably two to three, and most preferably two rings.

A 6a,10-dihydro-pyrrolidino[1,2a]quinoline is defined by the following structure.

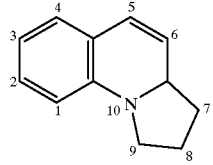

A 7a,11-dihydro-2-pyridono[5,6g]pyrrolidino[1,2a]quinoline is defined by the following structure.

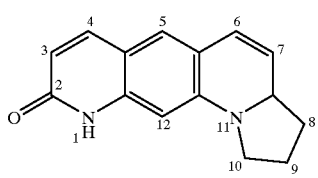

An 8-pyridono[5,6g]quinoline is defined by the following structure.

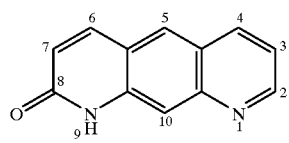

A 9-pyridono[6,5i]julolidine is defined by the following structure.

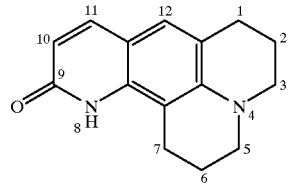

A 1,10-[1,3-dihydro-3-oxo-(2,1-isooxazolyl)]-8-pyridono[5,6g]quinoline is defined by the following structure.

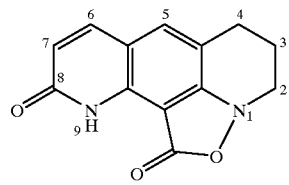

DETAILED DESCRIPTION OF EMBODIMENTS OF THE INVENTION

Compounds of the present invention are defined as those having the formula:

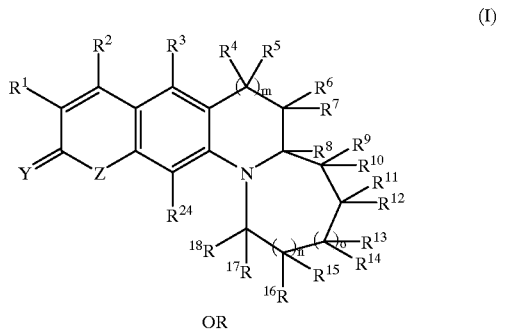

(I)

OR

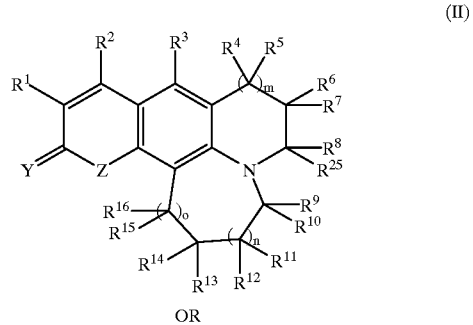

(II)

OR

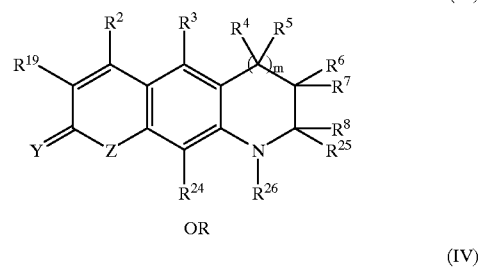

(III)

OR

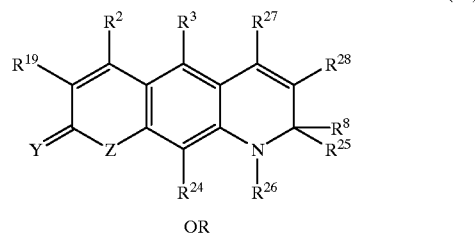

(IV)

OR

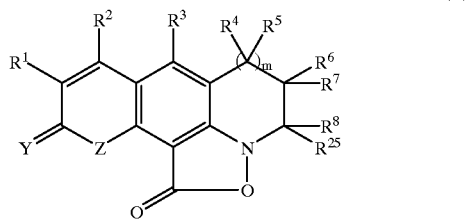

(V)

wherein:
$R^1$ is hydrogen, F, Cl, Br, I, $NO_2$, $OR^{20}$, $NR^{21}R^{22}$, $SR^{20}$, a $C_1$–$C_4$ alkyl or perhaloalkyl, or is an optionally substituted allyl, arylmethyl, alkynyl, alkenyl, aryl or heteroaryl, where R21 is hydrogen, a $C_1$–$C_6$ alkyl or perfluoroalkyl, aryl, heteroaryl, optionally substituted allyl or arylmethyl, $SO_2R^{23}$ or $S(O)R^{23}$, where $R^{23}$ is hydrogen, a $C_1$–$C_6$ alkyl or perfluoroalkyl, aryl, heteroaryl, optionally substituted allyl or arylmethyl, $R^{20}$ is hydrogen, a $C_1$–$C_6$ alkyl or perfluoroalkyl, aryl, heteroaryl, optionally substituted allyl or arylmethyl, and $R^{22}$ is hydrogen, a $C_1$–$C_4$ alkyl or perfluoroalkyl, aryl, heteroaryl, optionally substituted allyl $OR^{20}$ arylmethyl, OR or $NHR^{21}$;

$R^2$ is hydrogen, F, Br, Cl, a $C_1$–$C_4$ alkyl or perhaloalkyl, aryl, heteroaryl, $CF_3$, $CF_2H$, $CFH_2$, $CF_2OR^{20}$, $CH_2OR^{20}$, or $OR^{20}$, where $R^{20}$ has the same definition given above;

$R^3$ is hydrogen, a $C_1$–$C_4$ alkyl, F, Cl, Br, I, $OR^{20}$, $NR^{21}R^{22}$ or $SR^{20}$, where $R^{20}$ through $R^{22}$ have the definitions given above;

$R^4$ and $R^5$ each independently are hydrogen, a $C_1$–$C_4$ alkyl or perfluoroalkyl, heteroaryl, optionally substituted allyl, arylmethyl, alkynyl or alkenyl, or an aryl optionally substituted with hydrogen, F, Cl, Br, $OR^{20}$ or $NR^{21}R^{22}$, or $R^4$ and $R^5$ taken together can form a three- to seven-membered ring optionally substituted with hydrogen, F, Cl, Br, $OR^{20}$ or $NR^{21}R^{22}$, where $R^{20}$ through $R^{22}$ have the definitions given above;

$R^6$ and $R^7$ each independently are hydrogen, a $C_1$–$C_4$ alkyl or perfluoroalkyl, heteroaryl, optionally substituted allyl, arylmethyl, alkynyl or alkenyl, or an aryl optionally substituted with hydrogen, F, Cl, Br, $OR^{20}$ or $NR^{21}R^{22}$, or $R^6$ and $R^7$ taken together can form a three- to seven-membered ring optionally substituted with hydrogen, F, Cl, Br, $OR^{20}$ or $NR^{21}R^{22}$, where $R^{20}$ through $R^{22}$ have the definitions given above;

$R^8$ is hydrogen, a $C_1$–$C_{12}$ alkyl or perfluoroalkyl, hydroxymethyl, aryl, heteroaryl or optionally substituted allyl, arylmethyl, alkynyl or alkenyl;

$R^9$ through $R^{18}$ each independently are hydrogen, a $C_1$–$C_4$ alkyl or perfluoroalkyl, heteroaryl, optionally substituted allyl, arylmethyl, alkynyl or alkenyl, or an aryl optionally substituted with hydrogen, F, Cl, Br, $OR^{20}$ or $NR^{21}R^{22}$, or any two of $R^9$ through $R^{18}$ taken together can form a three- to seven-membered ring optionally substituted with hydrogen, F, Cl, Br, $OR^{20}$ or $NR^{21}R^{22}$, where $R^{20}$ through $R^{22}$ have the definitions given above;

$R^{19}$ is F, $NO_2$ or $SR^{20}$, where $R^{20}$ has the definition given above;

$R^{24}$ is hydrogen, a $C_1$–$C_4$ alkyl, F, Cl, Br, I, $NO_2$, $OR^{20}$, $NR^{21}R^{22}$ or $SR^{20}$, where $R^{20}$ through $R^{22}$ have the definitions given above;

$R^{25}$ is hydrogen, a $C_1$–$C_{12}$ alkyl, or perfluoroalkyl, hydroxymethyl, aryl, heteroaryl or optionally substituted allyl, arylmethyl, alkynyl or alkenyl, or $R^{25}$ and $R^8$ taken together can form a three- to seven-membered ring optionally substituted with hydrogen, F, Cl, Br, $OR^{20}$ or $NR^{21}R^{22}$, where $R^{20}$ through $R^{22}$ have the definitions given above;

$R^{26}$ is hydrogen, a $C_1$–$C_6$ alkyl or perfluoroalkyl, $NO_2$, $OR^{20}$, $C(O)R^{20}$, $C(O)OR^{20}$, $C(O)NR^{21}R^{22}$, or an optionally substituted aryl, heteroaryl, allyl or arylmethyl, where $R^{20}$ through $R^{22}$ have the definitions given above;

$R^{27}$ and $R^{28}$ each independently are hydrogen, F, Cl, Br, I, $OR^{20}$, $NR^{21}R^{22}$, a $C_1$–$C_4$ alkyl or perfluoroalkyl, heteroaryl, optionally substituted allyl, arylmethyl, alkynyl or alkenyl, or an aryl optionally substituted with hydrogen, F, Cl, Br, $OR^{20}$ or $NR^{21}R^{22}$, or $R^{27}$ and $R^{28}$ taken together can form a three- to seven-membered ring optionally substituted with hydrogen, F, Cl, Br, $OR^{20}$ or $NR^{21}R^{22}$, where $R^{20}$ through $R^{22}$ have the definitions given above;

m is 0 or 1;

n is 0 or 1;

o is 0 or 1;

Y is O or S;

Z is O, S, NH, $NR^{22}$ or $NCOR^{22}$, where $R^{22}$ has the same definition given above; and any two of $R^4$ through $R^8$, $R^{25}$ and $R^{28}$ taken together can form a three- to seven-membered ring optionally substituted with hydrogen, F, Cl, Br, $OR^{20}$ or $NR^{21}R^{22}$, where $R^{20}$ through $R^{22}$ have the definitions given above.

In a preferred aspect, the present invention provides a pharmaceutical composition comprising an effective amount of an androgen receptor modulating compound of formulae I through V shown above wherein $R^1$ through $R^{28}$, Y, Z, m, n and o all have the same definitions as given above.

In a further preferred aspect, the present invention comprises a method of modulating processes mediated by androgen receptors comprising administering to a patient an effective amount of a compound of the formulae I through V shown above, wherein $R^1$ through $R^{28}$, Y and Z all have the same definitions as those given above.

Any of the compounds of the present invention can be synthesized as pharmaceutically acceptable salts for incorporation into various pharmaceutical compositions. As used herein, pharmaceutically acceptable salts include, but are not limited to, hydrochloric, hydrobromic, hydroiodic, hydrofluoric, sulfuric, citric, maleic, acetic, lactic, nicotinic, succinic, oxalic, phosphoric, malonic, salicylic, phenylacetic, stearic, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydroxymethyl) aminomethane. Additional pharmaceutically acceptable salts are known to those skilled in the art.

AR agonist, partial agonist and antagonist compounds of the present invention will prove useful in the treatment of acne, male-pattern baldness, male hormone replacement therapy, wasting diseases, hirsutism, stimulation of hematopoiesis, hypogonadism, prostatic hyperplasia, various hormone-dependent cancers, including, without limitation, prostate and breast cancer and as anabolic agents.

It will be understood by those skilled in the art that while the compounds of the present invention will typically be employed as a selective agonists, partial agonists or antagonists, that there may be instances where a compound with a mixed steroid receptor profile is preferred. For example, use of a PR agonist (i.e., progestin) in female contraception often leads to the undesired effects of increased water retention and acne flare-ups. In this instance, a compound that is primarily a PR agonist, but also displays some AR and MR modulating activity, may prove useful. Specifically, the mixed MR effects would be useful to control water balance in the body, while the AR effects would help to control any acne flare-ups that occur.

Furthermore, it will be understood by those skilled in the art that the compounds of the present invention, including pharmaceutical compositions and formulations containing these compounds, can be used in a wide variety of combination therapies to treat the conditions and diseases described above. Thus, the compounds of the present invention can be used in combination with other hormones and other therapies, including, without limitation, chemotherapeutic agents such as cytostatic and cytotoxic agents, immunological modifiers such as interferons, interleukins, growth hormones and other cytokines, hormone therapies, surgery and radiation therapy.

Representative AR modulator compounds (i.e., agonists and antagonists) according to the present invention include: (R/S)-6,7,7a,11-tetrahydro-7a-methyl-4-trifluoromethyl-2-pyridono[5,6-g]pyrrolidino[1,2-a]quinoline; (R/S)-3-fluoro-6,7,7a,11-tetrahydro-7a-methyl-4-trifluoromethyl-2-pyridono[5,6-g]pyrrolidino[1,2-a]quinoline; (R/S)-6,7,7a, 11-tetrahydro-1,7a-dimethyl-4-trifluoromethyl-2-pyridono[5,6-g]pyrrolidino[1,2-a]quinoline; (R/S)-3-fluoro-6,7,7a, 11-tetrahydro- 1,7a-dimethyl-4-trifluoromethyl-2-pyridono[5,6-g]pyrrolidino[1,2-a]quinoline; 11-(trifluoromethyl)-9-pyridono[6,5-i]julolidine; 8-methyl-11-(trifluoromethyl)-9-pyridono[6,5-i]julolidine; 7-fluoro- 1,2,3,4-tetrahydro-2,2-dimethyl-6-trifluoromethyl-8-pyridono[5,6-g]quinoline; 6-difluoromethyl-7-fluoro- 1,2,3,4-tetrahydro-2,2-dimethyl-8-pyridono[5,6-g]quinoline; 7-fluoro-1,2,3,4-tetrahydro-2,2,9-trimethyl-6-trifluoromethyl-8-pyridono[5,6-g]quinoline; 6-difluoromethyl-7-fluoro-1,2,3,4-tetrahydro-2,2,9-trimethyl-8-pyridono[5,6-g]quinoline; 7-fluoro-1,2,3,4-tetrahydro-1,2,2,9-tetramethyl-6-trifluoromethyl-8-pyridono[5,6-g]quinoline; 6-difluoromethyl-7-fluoro-1,2,3,4-tetrahydro-1,2,2,9-tetramethyl-8-pyridono[5,6-g]quinoline; 7-fluoro-1,2-dihydro-2,2,4-trimethyl-6-trifluoromethyl-8-pyridono[5,6-g]quinoline; 7-fluoro-1,2,3,4-tetrahydro-2,2,4-trimethyl-6-trifluoromethyl-8-pyridono[5,6-g]quinoline; 1,10-[1,3-dihydro-3-oxo-(2,1-isoxazolyl)]-1,2,3,4-tetrahydro-2,2,4,10-tetramethyl-6-trifluoromethyl-8-pyridono[5,6-g]quinoline; 7-fluoro-1,2-dihydro-2,2,4,10-tetramethyl-6-trifluoromethyl-8-pyridono[5,6-g]quinoline; 7-fluoro-1,2,3,4-tetrahydro-2,2,4,10-tetramethyl-6-trifluoromethyl-8-pyridono[5,6-g]quinoline; 7-fluoro-1,2,3,4-tetrahydro-2,2,4,9,10-pentamethyl-6-trifluoromethyl-8-pyridono[5,6-g]quinoline; 7-fluoro-1,2,3,4-tetrahydro-1,2,2,4,10-pentamethyl-6-trifluoromethyl-8-pyridono[5,6-g]quinoline; 1,2,3,4-tetrahydro-1-hydroxy-2,2-dimethyl-6-trifluoromethyl-8-pyridono[5,6-g]quinoline; 1,2,3,4-tetrahydro-1-hydroxy-2,2,9-trimethyl-6-trifluoromethyl-8-pyridono[5,6-g]quinoline; 2,2-diethyl-7-fluoro-1,2,3,4-tetrahydro-6-trifluoromethyl-8-pyridono[5,6-g]quinoline; (R/S)-4-ethyl-1-formyl-1,2,3,4-tetrahydro-6-(trifluoromethyl)-8-pyridono[5,6-g]quinoline; (R/S)-4-ethyl-1,2,3,4-tetrahydro-1-(trifluoroacetyl)-6-(trifluoromethyl)-8-pyridono[5,6-g]quinoline; (R/S)-1-acetyl-4-ethyl-1,2,3,4-tetrahydro-6-(trifluoromethyl)-8-pyridono[5,6-g]quinoline; (R/S)-4-ethyl-1,2,3,4-tetrahydro-10-nitro-6-(trifluoromethyl)-8-pyridono[5,6-g]quinoline; 1,2,3,4-tetrahydro-2,2-dimethyl-10-nitro-6-(trifluoromethyl)-8-pyridono[5,6-g]quinoline; 1,2,3,4-tetrahydro-2,2-dimethyl-7,10-dinitro-6-(trifluoromethyl)-8-pyridono[5,6-g]quinoline; and (R/S)-4-ethyl-1,2,3,4-tetrahydro-1-nitro-6-(trifluoromethyl)-8-pyridono[5,6-g]quinoline.

Compounds of the present invention, comprising classes of heterocyclic nitrogen compounds and their derivatives, that can be obtained by routine chemical synthesis by those skilled in the art, e.g., by modification of the heterocyclic nitrogen compounds disclosed or by a total synthesis approach.

The sequences of steps for several general schemes to synthesize the compounds of the present invention are shown below. In each of the Schemes the R groups (e.g., $R^1$, $R^2$, etc.) correspond to the specific substitution patterns noted in the Examples. However, it will be understood by those skilled in the art that other functionalities disclosed herein at the indicated positions of compounds of formulas I through V also comprise potential substituents for the analogous positions on the structures within the Schemes.

Scheme I

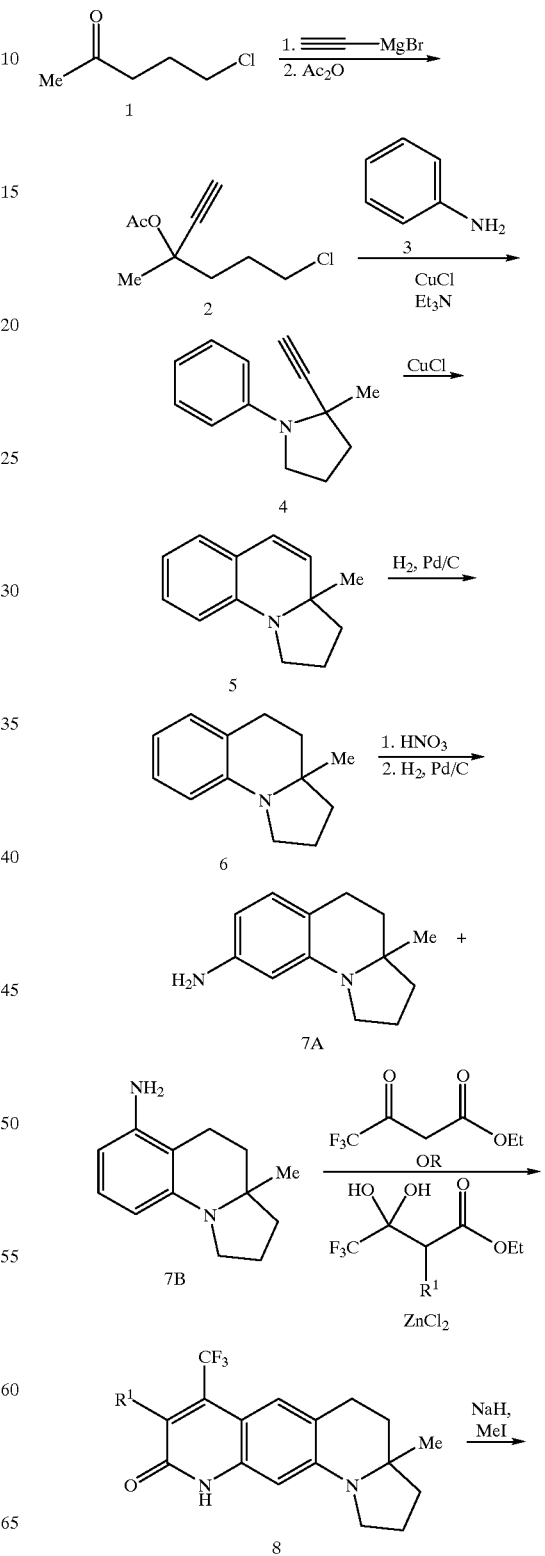

-continued

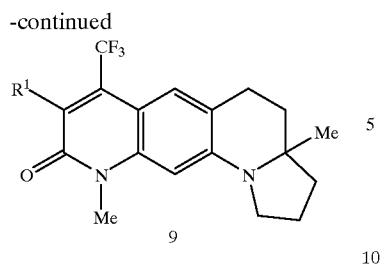
9

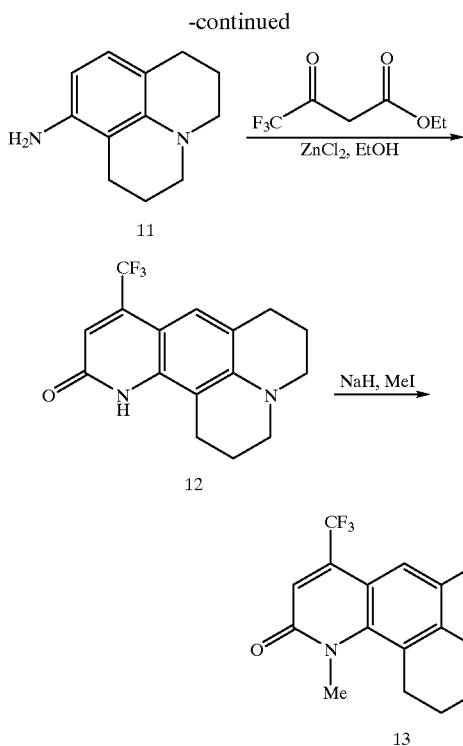

The process of Scheme I begins with an acetylide addition to 5-chloro-2-pentanone (Compound 1) with, for example, ethynylmagnesium bromide. The alcohol is then esterified to the corresponding acetate (Compound 2) with, for example, acetic anhydride and 4-dimethylaminopyridine in pyridine. A tandem propargylation/alkylation of Compound 2 with aniline (Compound 3) in the presence of a copper (I) or copper (II) salt, such as copper(I) chloride, and a base, such as triethylamine, affords Compound 4. See Y. Imada, M. Yuasa, I. Nakamura and S.-I. Murahashi, "Copper(I)-Catalyzed Amination of Propargyl Esters. Selective Synthesis of Propargylamines, 1-Alken-3-ylamines, and (Z)-Allylamines.", *J. Org. Chem.* 1994, 59, 2282, the disclosure of which is herein incorporated by reference. Cyclization of Compound 4 occurs in the presence of a copper catalyst, such as copper(I) chloride, to afford Compound 5. See N. R. Easton and D. R. Cassady, "A Novel Synthesis of Quinolines and Dihydroquinolines." *J. Org. Chem.* 1962, 27, 4713, and N. R. Easton and G. F. Hennion, "Metal Catalyst Process for Converting α-Amino-Acetylenes to Dihydroquinoline", U.S. Pat. No. 3,331,846 (1967), the disclosure of which is herein incorporated by reference.

Reduction of the olefin with, for example, hydrogen over a metal catalyst such as palladium on carbon, affords Compound 6. Nitration of Compound 6 with, for example, fuming nitric acid, followed by reduction of the nitro group with, for example, hydrogen over a metal catalyst such as palladium on carbon, affords the desired diamine (Compound 7A) along with small amounts of a regioisomer, which was separated (Compound 7B). A Knorr cyclization of Compound 7A with a β-keto ester or hydrated derivative, effected by, for example, zinc chloride, affords a compound of structure 8. See: E. T. McBee, O. R. Pierce, H. W. Kilbourne, and E. R. Wilson, "The Preparation and Reactions of Fluorine-containing Acetoacetic Esters." *J. Am. Chem. Soc.* 1953, 75, 3152, the disclosure of which is herein incorporated by reference, for the preparation of the fluorinated acetoacetate reagents. A compound of structure 8 may be further transformed into a compound of structure 9 by treatment of structure 8 with a base, such as sodium hydride, and an alkylating agent, such as methyl iodide.

Scheme II

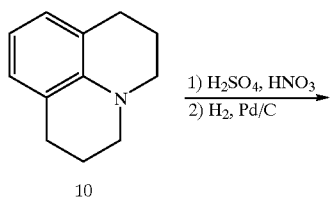
10

The process of Scheme II begins with the nitration of a tricyclic tetrahydroquinoline such as julolidine, Compound 10, followed by reduction of the nitro group to afford an aniline such as Compound 11. Treatment of Compound 11 with a β-keto ester such as ethyl 4,4,4-trifluoroacetoacetate and a Lewis acid such as zinc chloride (the Knorr reaction) affords a tetracyclic quinolinone such as Compound 12. The quinoline may be further functionalized by alkylation of the amide nitrogen by, for example, treatment with a base such as sodium hydride followed by the addition of an alkylating agent such as iodomethane, to afford a compound like Compound 13.

Scheme III

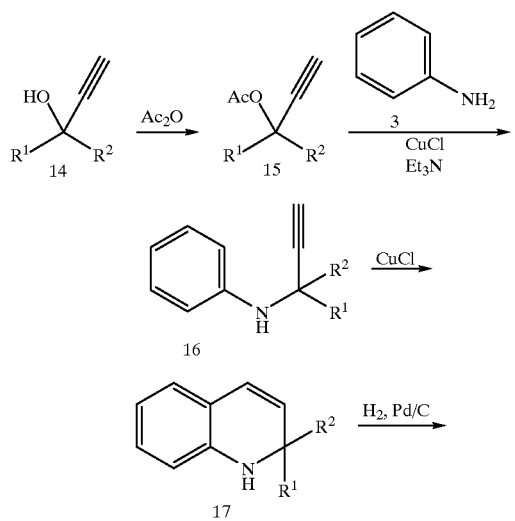

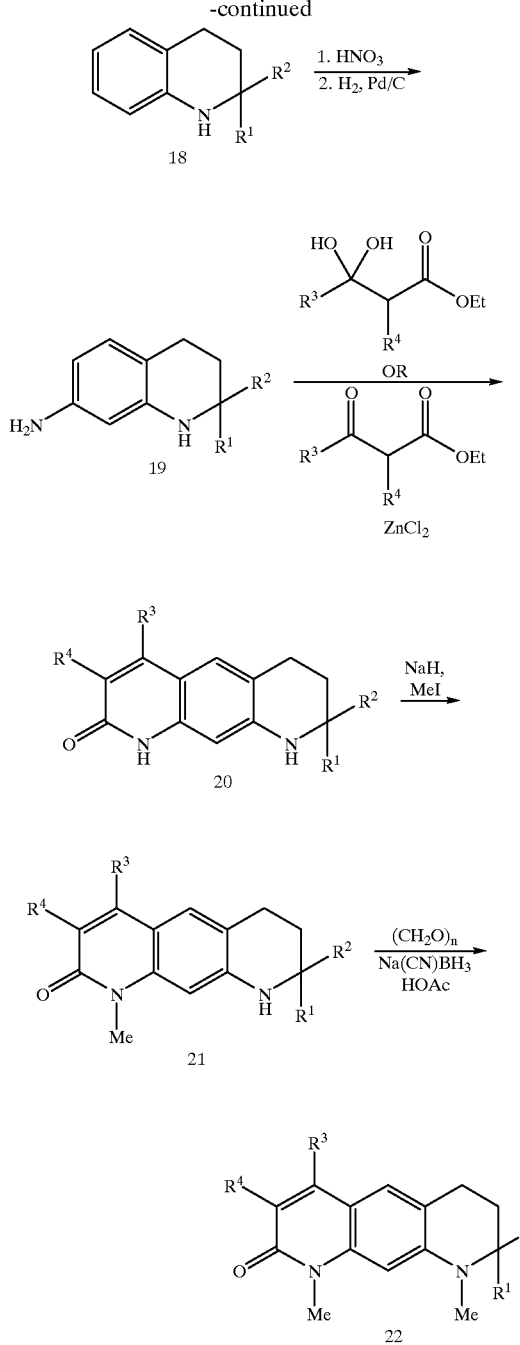

compound of DOCKET NO. structure 19. A Knorr cyclization of a compound of structure 19 with a β-keto ester or hydrated derivative, effected by, for example, zinc chloride, affords a compound of structure 20. A compound of structure 20 may be further transformed into a compound of structure 21 by treatment of structure 20 with a base, such as sodium hydride, and an alkylating agent, such as methyl iodide. A compound of structure 21 may be further transformed by reductive alkylation with, for example, paraformaldehyde and sodium borohydride in acetic acid, to afford a compound of structure 22.

Scheme IV

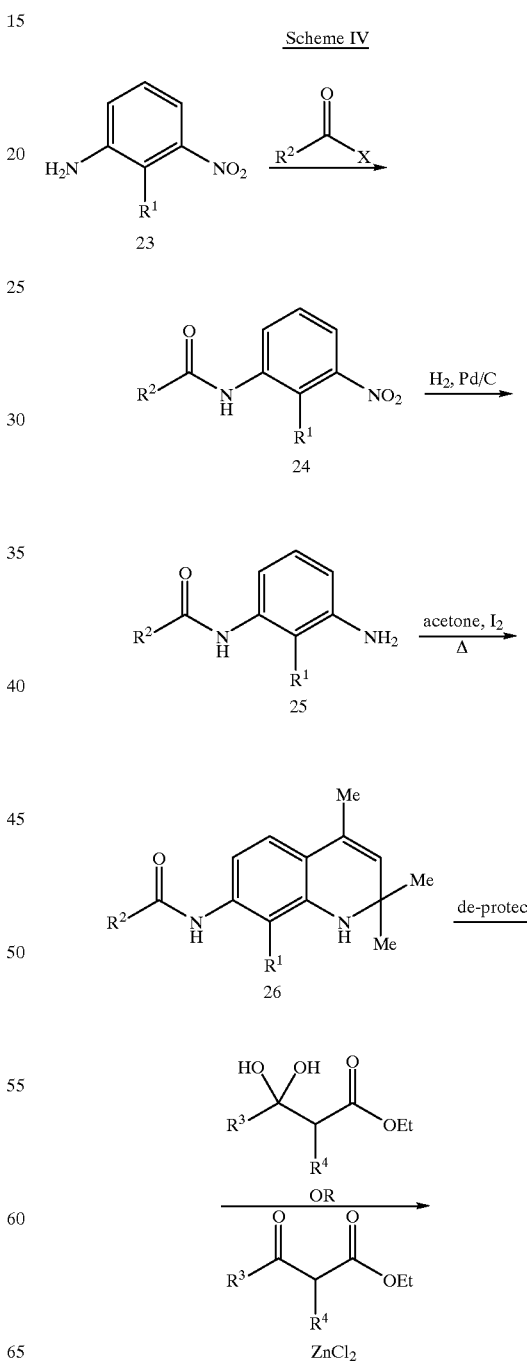

The process of Scheme III begins with an esterification of a propargyl alcohol (structure 14) with, for example, acetic anhydride and 4-dimethylaminopyridine in pyridine (structure 15). Alkylation of the acetate with aniline (Compound 3) in the presence of a copper(I) or copper(II) salt, such as copper(I) chloride, and a base, such as triethylamine affords a compound of structure 16. Cyclization of structure 16 occurs in the presence of a copper catalyst, such as copper(I) chloride, to afford a compound of structure 17.

Reduction of the olefin, with for example, hydrogen over a metal catalyst, such as palladium on carbon, affords a compound of structure 18. Nitration of a compound of structure 18 with, for example, fuming nitric acid, followed by reduction of the nitro group, with, for example hydrogen over a metal catalyst such as palladium on carbon, affords a

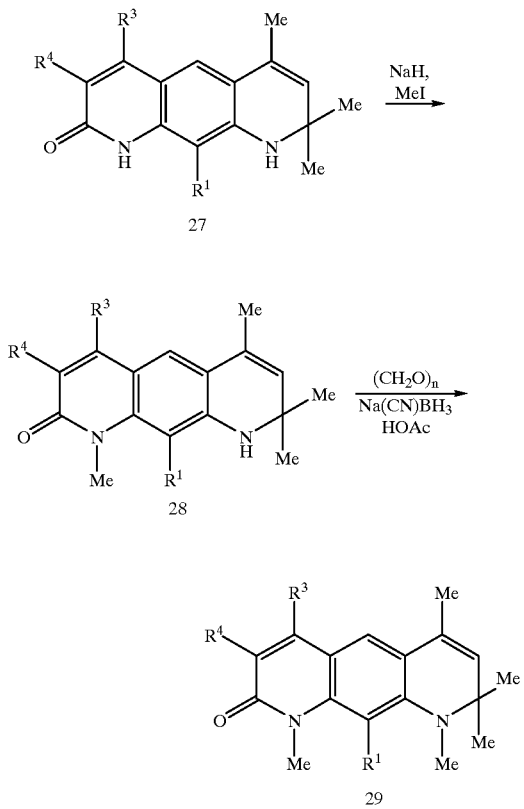

27

28

29

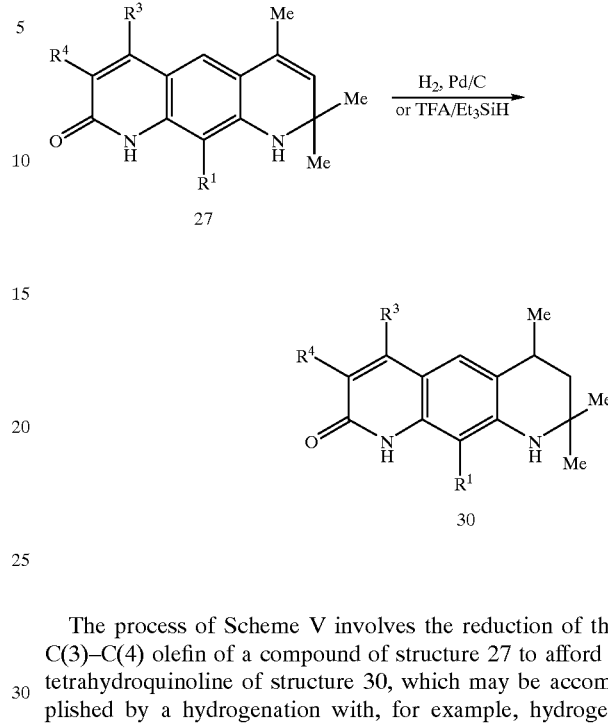

Scheme V

27

30

The process of Scheme V involves the reduction of the C(3)–C(4) olefin of a compound of structure 27 to afford a tetrahydroquinoline of structure 30, which may be accomplished by a hydrogenation with, for example, hydrogen over palladium on carbon, or by a cationic process with, for example, trifluoroacetic acid and triethylsilane.

The process of Scheme IV begins with the acylation of a 3-nitroaniline (structure 23) with an acylating agent, for example, di-tert-butyl dicarbonate or trimethylacetyl chloride, to afford a compound of structure 24. Reduction of the nitro group with, for example, hydrogen over a metal catalyst such as palladium on carbon, affords the corresponding aniline (structure 25). Treatment of a compound of structure 25 with acetone and a catalyst such as iodine affords a compound of structure 26, in a process known as the Skraup cyclization. See R. H. F. Manske and M. Kulka, "The Skraup Synthesis of Quinolines", *Organic Reactions* 1953, 7, 59, the disclosure of which is herein incorporated by reference. Deprotection by either acid or base, followed by treatment of the corresponding aniline with a β-keto ester (or corresponding hydrate) in the presence of a Lewis acid such as zinc chloride, affords as the major product a compound of structure 27. The cyclization of an aniline as described above is known as a Knorr cylization. See G. Jones, "Pyridines and their Benzo Derivatives: (v) Synthesis". In *Comprehensive Heterocyclic Chemistry*, Katritzky, A. R.; Rees, C. W., eds. Pergamon, New York, 1984. Vol. 2, chap. 2.08, pp 421–426. In turn, the quinolinone nitrogen may be alkylated by, for example, treatment with sodium hydride followed by iodomethane, to afford a compound of structure 28. Likewise, the quinoline nitrogen may be alkylated by, for example, treatment with paraformaldehdye and sodium cyano borohydride, to afford a compound of structure 29.

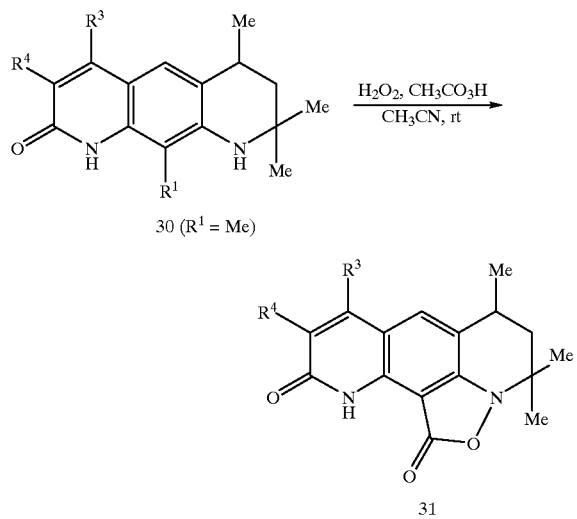

Scheme VI 30 (R$^1$ = Me)

31

The process of Scheme VI involves the oxidation of both the quinoline nitrogen and C(10) alkyl group of a compound of structure 30, followed cyclization and loss of water to afford a compound of structure 31. This may be effected by treatment of a compound of structure 30 (R$^1$=alkyl, preferably methyl) with an oxygen transfer agent or combination of oxygen transfer agents, such as hydrogen peroxide in the presence of peracetic acid, to afford a (Y compound of structure 31.

Scheme VII

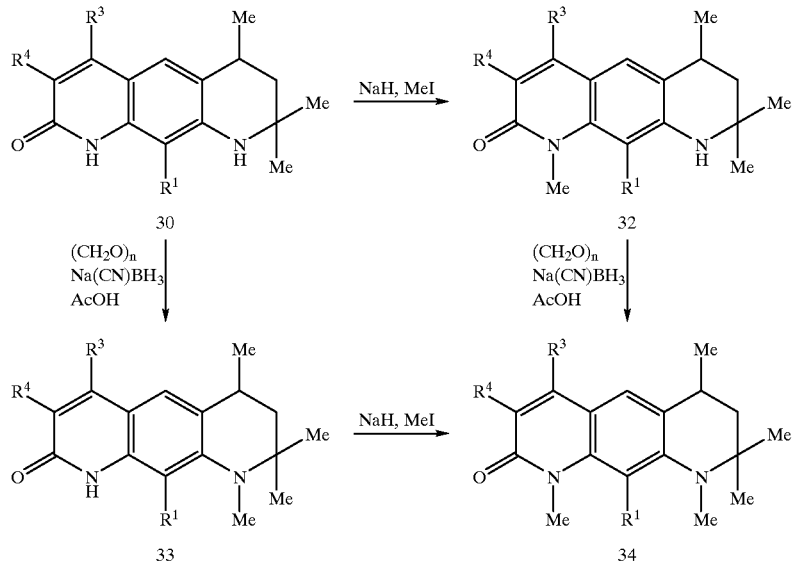

The process of Scheme VII involves the alkyation of one or both of the nitrogen atoms of a compound of structure 30. The quinolinone nitrogen may be selectively alkylated by treatment with a base, such as sodium hydride, followed by an alkylating agent, such as methyl iodide, to afford a compond of structure 32. The quinoline nitrogen may be selectively alkylated by a reductive alkylation procedure using, for example, paraformaldehdye in the presence of sodium cyano borohydride and acetic acid, to afford a compound of structure 33. Subsequently, the quinoline nitrogen of a compound of structure 32 may be reductively alkylated in a manner similar to the conversion of 30 to 33, or the quinolinone nitrogen of a compound of structure 33 may be alkylated in a manner similar to the conversion of 30 to 32. Either of these processes will afford a compound of structure 34.

The process of Scheme VIII begins with the oxidation of the quinoline nitrogen atom of a compound of structure 20 with an oxygen transfer agent or mixture of oxygen transfer agents, for example, hydrogen peroxide in the presence of peracetic acid, to afford a compound of structure 35. The quinolinone nitrogen may subsequently be alkylated by, for example, treatment with sodium hydride and methyl iodide, to afford a compound of structure 36.

Scheme IX

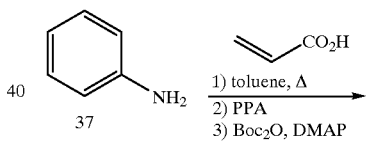

Scheme VIII

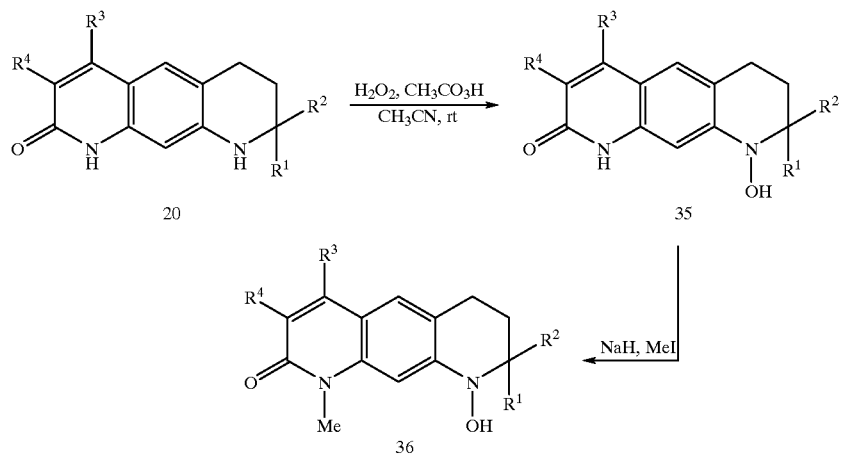

-continued

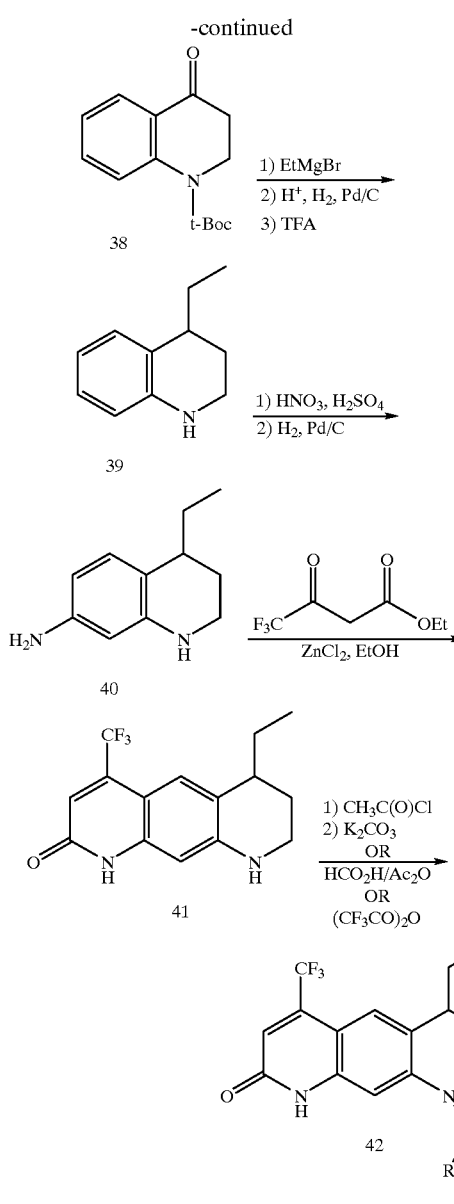

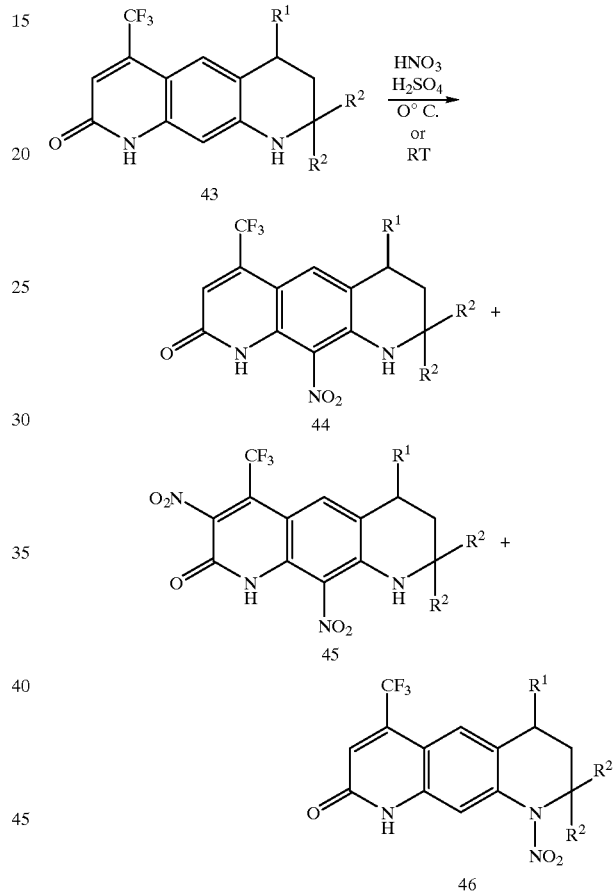

The process of Scheme IX begins with the reaction of an aniline (structure 37) with an unsaturated acid, for example acrylic acid, followed by a cyclization reaction mediated by, for example, polyphosphoric acid to afford a 4-quinolinone. The nitrogen atom is then protected by treatment with a base, for example, 4-dimethylaminopyridine, followed by the addition of an acylating agent such as di-tert-butyldicarbonate, to afford a compound of structure 38. Addition of an organomagnesium or organolithium reagent, with, for example, ethyl magnesium bromide, affords an alcohol. Reduction of the alcohol with, for example hydrogen over palladium on carbon, followed by deprotection of the nitrogen atom, affords a compound of structure 39. Nitration of a compound of structure 39 by the action of nitric acid in the presence of, for example, sulfuric acid, followed by reduction of the nitro group with, for example, hydrogen over palladium on carbon, affords a 7-amino-1,2,3,4-tetrahydroquinoline of structure 40. A Knorr cyclization with a β-keto ester effected by, for example, zinc chloride, affords a compound of structure 41. A compound of structure 41 may be further transformed into a compound of structure 42 by acylation of the quinoline nitrogen, which may be accomplished in one of two ways. Treatment of structure 41 with an acid chloride, for example, acetyl chloride, followed by treatment with a base, for example, potassium carbonate, to afford a compound of structure 42. Alternatively, treatment of structure 41 may be treated with an anhydride, for example, trifluoroacetic anhyride, likewise to afford a compound of structure 42.

The process of Scheme X involves the treatment of structure 43 with, for example, nitric acid in the presence of, for example, sulfuric acid, to afford compounds of structure 44, 45 and 46.

The compounds of the present invention also include racemates, stereoisomers and mixtures of said compounds, including isotopically-labeled and radio-labeled compounds. Such isomers can be isolated by standard resolution techniques, including fractional crystallization and chiral column chromatography.

As noted above, any of the steroid modulator compounds of the present invention can be combined in a mixture with a pharmaceutically acceptable carrier to provide pharmaceutical compositions useful for treating the biological conditions or disorders noted herein in mammalian, and more preferably, in human patients. The particular carrier employed in these pharmaceutical compositions may take a wide variety of forms depending upon the type of administration desired, e.g., intravenous, oral, topical, suppository or parenteral.

In preparing the compositions in oral liquid dosage forms (e.g., suspensions, elixirs and solutions), typical pharmaceutical media, such as water, glycols, oils, alcohols, flavoring agents, preservatives, coloring agents and the like can be employed. Similarly, when preparing oral solid dosage forms (e.g., powders, tablets and capsules), carriers such as starches, sugars, diluents, granulating agents, lubricants, binders, disintegrating agents and the like will be employed. Due to their ease of administration, tablets and capsules represent the most advantageous oral dosage form for the pharmaceutical compositions of the present invention.

For parenteral administration, the carrier will typically comprise sterile water, although other ingredients that aid in solubility or serve as preservatives may also be included. Furthermore, injectable suspensions may also be prepared, in which case appropriate liquid carriers, suspending agents and the like will be employed.

For topical administration, the compounds of the present invention may be formulated using bland, moisturizing bases, such as ointments or creams. Examples of suitable ointment bases are petrolatum, petrolatum plus volatile silicones, lanolin, and water in oil emulsions such as Eucerin™ (Beiersdorf). Examples of suitable cream bases are Nivea™ Cream (Beiersdorf), cold cream (USP), Purpose Cream™ (Johnson & Johnson), hydrophilic ointment (USP), and Lubriderm™ (Warner-Lambert).

The pharmaceutical compositions and compounds of the present invention will generally be administered in the form of a dosage unit (e.g., tablet, capsule etc.) at from about 1 μg/kg of body weight to about 500 mg/kg of body weight, more preferably from about 10 μg/kg to about 250 mg/kg, and most preferably from about 20 μg/kg to about 100 mg/kg. As recognized by those skilled in the art, the particular quantity of pharmaceutical composition according to the present invention administered to a patient will depend upon a number of factors, including, without limitation, the biological activity desired, the condition of the patient, and tolerance for the drug.

The compounds of this invention also have utility when radio- or isotopically-labeled as ligands for use in assays to determine the presence of AR in a cell background or extract. They are particularly useful due to their ability to selectively activate androgen receptors, and can therefore be used to determine the presence of such receptors in the presence of other steroid receptors or related intracellular receptors.

Due to the selective specificity of the compounds of this invention for steroid receptors, these compounds can be used to purify samples of steroid receptors in vitro. Such purification can be carried out by mixing samples containing steroid receptors with one or more of the compounds of the present invention so that the compounds bind to the receptors of choice, and then separating out the bound ligand/receptor combination by separation techniques that are known to those of skill in the art. These techniques include column separation, filtration, centrifugation, tagging and physical separation, and antibody complexing, among others.

The compounds and pharmaceutical compositions of the present invention can advantageously be used in the treatment of the diseases and conditions described herein. In this regard, the compounds and compositions of the present invention will prove particularly useful as modulators of male sex steroid-dependent diseases and conditions such as the treatment of acne, male-pattern baldness, male hormone replacement therapy, wasting diseases, hirsutism, stimulation of hematopoiesis, hypogonadism, prostatic hyperplasia, various hormone-dependent cancers, including, without limitation, prostate and breast cancer and as anabolic agents.

The compounds and pharmaceutical compositions of the present invention possess a number of advantages over previously identified steroidal and non-steroidal compounds.

Furthermore, the compounds and pharmaceutical compositions of the present invention possess a number of advantages over previously identified steroid modulator compounds. For example, the compounds are extremely potent activators AR, preferably displaying 50% maximal activation of AR at a concentration of less than 100 nM, more preferably at a concentration of less than 50 nM, more preferably yet at a concentration of less than 20 nM, and most preferably at a concentration of 10 nM or less. Also, the selective compounds of the present invention generally do not display undesired cross-reactivity with other steroid receptors, as is seen with the compound mifepristone (RU486; Roussel Uclaf), a known PR antagonist that displays an undesirable cross reactivity on GR and AR, thereby limiting its use in long-term, chronic administration. In addition, the compounds of the present invention, as small organic molecules, are easier to synthesize, provide greater stability and can be more easily administered in oral dosage forms than other known steroidal compounds.

The invention will be further illustrated by reference to the following non-limiting Examples.

EXAMPLE 1

(R/S)-6,7,7a,11-Tetrahydro-7a-methyl-4-trifluoromethyl-2-pyridono[5,6-g]pyrrolidino[2-a] quinoline (Compound 101, Structure 8 of Scheme 1, where $R^1$=H)

(R/S)-6-Chloro-3-methylhex-1-yn-3-yl acetate (Compound 2)

In a 1-L, 3-neck r.b. flask with an addition funnel, a solution 5-chloro-2-pentanone (33.1 g, 274 mmol) in THF (140 mL) was treated with ethynylmagnesium bromide (564 mL of a 0.5 M solution in THF, 282 mmol, 1.03 equiv) over 0.5 h at −78° C. The internal temperature rose to −30° C. during the addition. The mixture was allowed to warm to 0° C. and stirred for 1 h, then was poured into a cold mixture of ether (400 mL) and 1 N $NaHSO_4$ (400 mL). The aqueous layer was extracted with ether (2×200 mL), and the combined organic layers were washed with brine, dried ($MgSO_4$) filtered, and concentrated to 42 g of a brown oil. This material was transferred to a 250-mL r.b. flask, whereupon pyridine (27 mL) and acetic anhydride (36.4 g, 356 mmol, 1.3 equiv) were added, then the flask was cooled to 0° C. DMAP (1.67 g, 13.7 mmol, 5%) was added, and the solution was stirred for 2 d, then treated with MeOH (10 mL). After 1 h, the solution was poured into a cold mixture of ether (250 mL) and 2 N $NaHSO_4$ (250 mL). The aqueous layer was extracted with ether (250 mL), and the combined organic layers were washed with brine (250 mL), dried ($MgSO_4$), filtered, and concentrated to a brown oil. Distillation afforded 30.5 g (58.8%) of Compound 2, a colorless oil, bp 79–80° C. @ 10 mm Hg. Data for Compound 2: $^1$H NMR (400 MHz, $CDCl_3$) 3.52–3.65 (m, 2H), 2.57 (s, 1H), 1.85–2.15 (m, 4H), 2.04 (s, 3H), 1.71 (s, 3H).

(R/S)-2-Ethynyl-2-methyl-1-phenylpyrrolidine (Compound 4)

In a 250-mL 3-neck r.b. flask with a water cooled reflux condensor, a mixture of aniline (5.43 g, 58.3 mmol, 1.07 equiv), copper(I) chloride (0.528 g, 5.33 mmol, 0.098 equiv), and triethylamine (5.90 g, 58.3 mmol, 1.07 equiv) in THF (110 mL) was treated with 6-chloro-3-methylhex-1-yn-3-yl acetate (10.2 g, 54.3 mmol) in THF (10 mL) over 5 min. The mixture was heated at reflux for 5 h, cooled to rt, and poured into a mixture of EtOAc (100 mL) and saturated $NH_4Cl$ (100 mL). The aqueous layer was extracted with EtOAc (100 mL). The extracts were washed with brine (100 mL), dried ($MgSO_4$), filtered, and concentrated to a brown oil. Purification by flash chromatography (7×20 cm column, hexane:EtOAc, 19:1) afforded 6.35 g (63%) of compound 4 as a light golden oil. Data for Compound 4: $R_f$=0.32 (19:1 hexanes:EtOAc); $^1$H NMR (400 MHz, $CDCl_3$) 7.20–7.28 (m, 2H), 6.95 (d J=8.1, 2H), 6.72 (t, J=7.2, 1H), 3.43–3.52 (m, 1H), 3.35–3.43 (m, 1H), 2.40–2.50 (m, 1H), 2.40 (s,1H), 2.05–2.17 (m, 2H), 1.92–2.02 (m, 1H), 1.62 (s, 3H).

(R/S)-6a,10-Dihydro-6a-methyl-pyrrolidino[1,2,a]-quinoline (Compound 5)

In a 100-mL r.b. flask equipped with a water cooled condensor, a mixture of Compound 4 (1.85 g, 10.0 mmol) and copper(I) chloride in THF (40 mL) was heated at reflux for 10 h, cooled to rt, then poured into a mixture of EtOAc (75 mL) and saturated $NH_4Cl$ (75 mL). The aqueous layer was extracted with EtOAc (75 mL). The extracts were washed with brine (75 mL), dried ($MgSO_4$), filtered, and concentrated to a brown oil. Purification by flash chromatography (5×15 cm column, hexane:EtOAc, 24:1) afforded 1.37 g (74%) of Compound 5 as a light amber oil. Data for Compound 5: $R_f$ 0.37 (24:1 hexanes:EtOAc); $^1$H NMR (400 MHz, $CDCl_3$) 7.06 (td, J=7.9, 1.0, 1H), 6.92 (dd, J=7.3, 0.9, 1H), 6.55 (t, J=7.3, 1H), 6.37 (d, J=8.0, 1H), 6.27 (d, J=9.6, 1H), 5.62 (d, J=9.6, 1H), 3.40–3.50 (m, 1H), 3.28–3.38 (m, 1H), 1.85–2.05 (m, 4H), 1.08 (s, 3H).

5,6,6a,10-Tetrahydro-6a-methyl-pyrrolidino[1,2-a]quinoline (Compound 6)

In a 100 mL r.b. flask, a mixture of Compound 5 (1.37 g, 7.39 mmol) and 10% Pd/C (68 mg, 5%) in EtOAc (15 mL) was flushed with hydrogen gas, then placed under a balloon of hydrogen. After 4 d, the mixture was filtered through Celite and concentrated to 1.36 g (98.6%) of Compound 6 as a colorless oil. Data for Compound 6: $^1$H NMR (400 MHz, $CDCl_3$) 7.07 (t, J=7.7, 1H), 7.03 (d, J=7.4, 1H), 6.55 (td, J=7.3, 0.9, 1H), 6.41 (d, J=8.0 Hz, 1H), 3.46 (td, J=9.1, 2.1, 1H), 3.19 (q, J=9.1 Hz, 1H), 2.86–2.96 (m, 1H), 2.72 (ddd, J=16.5, 5.1, 1.9), 2.05–2.20 (m, 1H), 1.88–2.08 (m, 3H), 1.60 (td, J=12.0, 7.8, 1H), 1.42 (td, J=13.2, 5.1, 1H), 1.04 (s, 3H).

(R/S)-5 6,6a,10-Tetrahydro-6a-methyl-2-nitropyrrolidino[1,2-a]quinoline

In a 25 mL r.b. flask, a solution of Compound 6 (1.21 g, 6.47 mmol) in concentrated sulfuric acid (12.9 mL) was cooled to −5° C. and treated with fuming nitric acid (0.26 mL, 6.5 mmol) dropwise over 3 min. The reddish solution was stirred for 20 min, then poured carefully into a cold mixture of $CH_2Cl_2$ (100 mL) and saturated $K_2CO_3$ (100 mL). The aqueous layer was extracted with $CH_2Cl_2$ (2×100 mL), and the combined organic layers were washed with phosphate buffer (pH 7, 100 mL), dried ($MgSO_4$), filtered, and concentrated to an orange oil. Purification by flash chromatography (5×12 cm column, hexane:EtOAc, 9:1) afforded 1.11 g (74%) of (R/S)-5,6,6a,10-tetrahydro-6a-methyl-2-nitro-pyrrolidino[1,2-a]quinoline as an orange oil. Data for (R/S)-5,6,6a,10-tetrahydro-6a-methyl-2-nitro-pyrrolidino[1,2-a]quinoline: $R_f$ 0.39 (9:1 hexanes:EtOAc); $^1$H NMR (400 MHz, $CDCl_3$) 7.38 (dd, 8.1, 2.3, 1H), 7.18 (d, J=2.3, 1H), 7.09 (d, J=8.1, 1H), 3.52 (td, J=9.2, 1.9, 1H), 3.25 (q, J=9.2, 1H), 2.88–2.98 (m, 1H), 2.78–2.88 (m, 1H), 2.15–2.25 (m, 1H), 1.95–2.15 (m, 3H), 1.64 (td, J=12.1, 7.8, 1H), 1.41 (td, J=13.2, 5.2, 1H), 1.07 (s, 3H).

(R/S)-2-Amino-5,6,6a,10-Tetrahydro-6a-methyl-pyrrolidino[1.2-a]quinoline (Compound 7)

In a 25 mL r.b. flask, a mixture of (R/S)-5,6,6a,10-tetrahydro-6a-methyl-2-nitro-pyrrolidino[1,2-a]quinoline (1.02 g, 4.37 mmol) and 10% Pd/C (51 mg, 5%) in EtOAc (2.2 mL) and EtOH (2.2 mL) was flushed with hydrogen gas, then placed under an atmosphere of hydrogen. After 16 h, the mixture was filtered through Celite and concentrated to a colorless oil. Purification by flash chromatography (5×12 cm column, hexane:EtOAc, 7:3) afforded 589 mg (67%) of desired Compound 7A, a colorless oil. Also isolated was 89 mg (10%) of regioisomeric Compound 7B, a colorless oil. Data for Compound 7A: $R_f$ 0.34 (7:3 hexanes:EtOAc); $^1$H NMR (400 MHz, $CDCl_3$) 6.81 (d, J=7.7, 1H), 5.95 (dd, J=7.7, 2.2, 1 H), 5.79 (d, J=2.1, H), 3.46 (broad s, 2H), 3.40 (td, J=9.1, 1.7, 1H), 3.16 (q, J=8.9, 1H), 2.75–2.85 (m, 1H), 2.62 (dd, J=16.1, 3.8, 1H), 2.06–2.18 (m, 1H), 1.85–2.05 (m, 3H), 1.57 (td, J=12.0, 7.9, 1H), 1.39 (td, J=13.0, 5.1, 1H), 1.02 (s, 3H). Data for Compound 7B: $R_f$ 0.45 (7:3 hexanes:EtOAc); $^1$H NMR (400 MHz, $CDCl_3$) δ6.91 (t, J=7.9, 1H), 6.04 (d, J=7.8, 1H), 5.96 (d, J=8.1, 1H), 3.50 (broad s, 2H), 3.40 (td, J=9.0, 2.2, 1H), 3.23 (q, J=8.7, 2H), 2.4–2.6-(m, 2H), 1.75–2.15 (m, 4H), 1.55–1.65 (m, 1H), 1.45 (td, J=12.5, 6.7, 1H), 1.00 (s, 3H).

(R/S)-6,7,7a,11-Tetrahydro-7a-methyl-4-trifluoromethyl-2-pyridono[5,6-g]pyrrolidino[1,2-a]quinoline (Compound 101, Structure 8 of Scheme 1 where $R^1$=H)

In a 100 mL r.b. flask, a suspension of Compound 7 (512 mg, 2.56 mmol), ethyl 4,4,4-trifluoroacetoacetate (518 mg, 2.82 mmol, 1.1 equiv) and 4 angstrom molecular sieves (260 mgs, 50%) in benzene (25.6 mL) was treated with $ZnCl_2$ (523 mg, 3.83 mmol, 1.5 equiv). The mixture was heated at reflux for 1 h, then treated with benzene (15 mL) and isopropanol (5 mL) to disperse the precipitates, and heated at reflux for 3 h. The mixture was treated with p-TsOH (190 mg, 1.00 mmol, 0.39 equiv), heated at reflux for 2 h, cooled to 0° C., and poured into a mixture of EtOAc (200 mL) and water (200 mL). The sieves were filtered, and the organic layer was washed with brine (100 mL), dried ($MgSO_4$), filtered, and concentrated to light brown solid. Purification by flash chromatography (5×12 cm column, $CH_2Cl_2$:EtOAc, 3:2) afforded 130 mg (16%) of Compound 101 as a yellow solid, plus 320 mg (39%) of impure Compound 101. Data for Compound 101: $R_f$ 0.15 1:1:1 EtOAc:$CH_2Cl_2$:hexanes); $^1$H NMR (400 MHz, acetone-$d_6$) 10.54 (s, 1H), 7.34 (s, 1H), 6.42 (s, 1H), 6.36 (s, 1H), 3.52 (t, J=9.7, 1H), 3.28 (q, J=9.6, 1H), 2.92–3.05 (m, 1H), 2.80–2.90 (m, 1H), 2.18–2.30 (m, 1H), 2.00–2.20 (m, 3 H), 1.68 (td, J=12.1, 7.9, 1H), 1.46 (td, J=13.3, 5.1, 1H), 1.14 (s, 3H).

EXAMPLE 2

(R/S)-3-Fluoro-6,7,7a,11-tetrahydro-7a-methyl-4-trifluoromethyl-2-pyridono[5,6-g]pyrrolidino[1,2-a]quinoline (Compound 102, Structure 8 of Scheme 1, where $R^1$=F)

Ethyl 2,4,4,4-tetrafluoro-3,3-dihydroxybutanoate (Scheme 1)

In a 100 mL-r.b flask, a suspension of ethyl trifluoroacetate (31.6 g, 223 mmol, 1.44 equiv) and NaH (7.79 g of a 60% mineral oil suspension, 195 mmol, 1.05 equiv, rinsed with 20 mL of pentane) was treated with ethyl fluoroacetate (16.4 g, 154 mmol) at 50° C. over 6 h. The addition was stopped when the evolution of $H_2$ was no longer observed. The mixture was heated at 50° C. for 2 h, allowed to stir at rt overnight, then poured into a mixture of ice (100 g), concentrated $H_2SO_4$ (19.5 mL) and ether (200 mL). The aqueous layer was extracted with ether (200 mL). The combined organic layers were washed with phosphate buffer (pH 7, 50 mL), brine (50 mL), dried ($MgSO_4$), filtered, and concentrated to a 2-phase oil. The lower layer was drawn off and distilled to afford 15.1 g of a colorless liquid, bp 30–31° C. @ 15 mm Hg. The oil crystallized at 0° C. to afford 5.76 g (18%) of ethyl 2,4,4,4-tetrafluoro-3,3-dihydroxybutanoate, a white solid. Data for ethyl 2,4,4,4-tetrafluoro-3,3-dihydroxybutanoate: $^1$H NMR (400 MHz, $CDCl_3$) 5.06 (d, J=47.7, 1H), 4.80 (broad s, 1H), 4.40 (q, J=7.2, 2H), 4.07 (broad s, 1H), 1.39 (t, J=7.2, 3H).

In a 15-mL r.b. flask equipped with a water cooled condensor, a suspension of Compound 7 (122 mg, 0.609 mmol), ethyl 2,4,4,4-tetrafluoro-3,3-dihydroxybutanoate (147 mg, 0.670 mmol, 1.1 equiv) and 4 angstrom molecular sieves (120 mgs, 100%) in benzene (1.2 mL) was treated with $ZnCl_2$ (124 mg, 0.913 mmol, 1.5 equiv). The mixture was heated at reflux for 6 h, then treated with p-TsOH (23 mg, 0.12 mmol, 0.20 equiv) and EtOH (0.3 mL). After 2 h at reflux, the mixture was poured into a mixture of EtOAc (50 mL) and water (25 mL), filtered through Celite, and the aqueous layer was extracted with EtOAc (50 mL). The combined organic layers were washed with brine, dried ($MgSO_4$), filtered, and concentrated to light brown residue. Purification by flash chromatography (3.5×15 cm column, $CH_2Cl_2$:MeOH, 23:2) afforded 77 mg (37%) of Compound 102 as a yellow solid. Data for Compound 102: $R_f$ 0.54 ($CH_2Cl_2$:MeOH, 23:2); $^1$H NMR (400 MHz, $CDCl_3$) 11.29 (s, 1H), 7.41 (s, 1H), 6.17 (s, 1H), 3.53 (t, J=9.5, 1H), 3.30 (q, J=9.2, 1H), 2.95–3.05 (m, 1H), 2.77–2.86 (m, 1 H), 2.15–2.25 (m, 1H), 2.03–2.15 (m, 2H), 2.00 (dd, J=11.9, 6.8, 1H), 1.60–1.70 (m, 1H), 1.46 (td, J=13.3, 4.9, 1H), 1.10 (s, 3H).

EXAMPLE 3

(R/S)-6,7,7a,11-Tetrahydro-1,7a-dimethyl-4-trifluoromethyl-2-pyridono[5,6-g]pyrrolidino[1,2-a]quinoline (Compound 103, Structure 9 of Scheme 1, where $R^1$=H)

In a 25-mL r.b. flask, a mixture of Compound 101 (73 mg, 0.23 mmol) and NaH (36 mg of a 60% mineral oil dispersion. 0.91 mmol, 4 equiv) in THF (3.3 mL) was stirred for 0.5 h, then treated with iodomethane (129 mg, 0.91 mmol, 4 equiv). The mixture was quenched with phosphate buffer (pH 7, 20 mL), and aqueous layer was extracted with EtOAc (2×20 mL). The combined organic layers were washed with brine (20 mL), dried ($MgSO_4$), filtered, and concentrated to a yellow solid. Purification by flash chromatography (3×15 cm column, $CH_2Cl_2$:EtOAc:hexanes, 2:1:1) afforded 31 mg (41%) of Compound 103, a yellow solid. Data for Compound 103: $R_f$ 0.52 (2:1:1 $CH_2Cl_2$: EtOAc:hexanes); $^1$H NMR (400 MHz, $CDCl_3$) 7.44 (s, 1H), 6.71 (s, 1H), 6.12 (s, 1H), 3.67 (s, 3H), 3.56 (t, J=9.0, 1 H), 3.30 (q, J=9.2, 1 H), 2.95–3.05 (m, 1H), 2.80–2.90 (m, 1H), 2.20–2.32 (m, 1H), 2.08–2.20 (m, 2 H), 2.03 (dd, J=11.9, 6.8, 1H), 1.68 (td,J= 12.2, 7.9, 1H), 1.48 (td,J=13.3, 5.1, 1H), 1.13 (s, 3H).

EXAMPLE 4

(R/S)-3-Fluoro-6,7,7a,11-tetrahydro-1,7a-dimethyl-4-trifluoromethyl-2-pyridono[5,6-g]pyrrolidino[1,2-a]quinoline (Compound 104, Structure 9 of Scheme 1, where $R^1$=F)

This compound was prepared in a manner similar to that described for the preparation of Compound 103 (EXAMPLE 3) from Compound 102 (40 mg, 0.12 mmol), NaH (9.3 mg of a 60% mineral oil dispersion. 0.23 mmol, 2 equiv), and iodomethane (33 mg, 0.23 mmol, 2 equiv) in THF (1.2 mL) to afford 4.8 mg (12%) of Compound 104, a yellow solid, after chromatography ($CH_2Cl_2$:EtOAc, 24:1). Data for Compound 104: $^1$H NMR (400 MHz, $CDCl_3$) 7.46 (s, 1H), 6.11 (s, 1H), 3.72 (s, 3H), 3.54 (t, J=8.8, 1H), 3.31 (q, J=9,1, 1H), 2.95–3.07 (m, 1H), 2.80–2.88 (m, 1H), 2.20–2.30 (m, 1H), 2.07–2.22 (m, 2H ), 2.03 (dd, J=12.0, 6.8, 1H), 1.68 (td, J=12.2, 7.9, 1H), 1.47 (td, J=13.4, 5.1, 1H), 1.12 (s, 3H).

EXAMPLE 5

11-(Trifluoromethyl)-9-pyridono[6,5-i]julolidine (Compound 12 of Scheme II)

7-Nitrojulolidine

In a 250 mL r.b. flask was introduced julolidine (2.12 g, 12.2 mmol), and concentrated sulfuric acid (14 mL). The reaction mixture was cooled to 0° C. and 90% nitric acid (0.55 mL, 12 mmol, 1.0 equiv) was added via syringe over a period of 10 min. The reaction mixture was stirred an additional 10 min and poured over ice (100 g). The resulting suspension was neutralized by the slow addition of potassium carbonate (40 g) in four equal portions. The product was extracted with $CH_2Cl_2$ (3×100 mL) and washed with saturated $NaHCO_3$ (1×100 mL). The extracts were combined, dried ($MgSO_4$), filtered through a pad of Celite, and concentrated to a yellow solid (2.68 g, 99%). Data for 7-nitrojulolidine: $^1$H NMR (400 MHz, $CDCl_3$) 6.99 (d, J=8.3, 1H), 6.82 (d, J=8.3, 1H), 3.20 (q, J=5.7, 4H), 2.91 (t, J=6.5, 2H), 2.77 (t, J=6.4, 2H), 1.94 (m, 4H).

11-(Trifluoromethyl)-9-pyridono[6,5-i]juloldine (Compound 12 of Scheme II).

In a 100 mL r.b. flask, a solution of 7-nitrojulolidine (0.44 g, 2.0 mmol) in 1:1 EtOH:EtOAc (20 mL) was treated with 10% Pd/C (200 mg) and stirred under an atmosphere of $H_2$ for 4 h. The reaction mixture was filtered and concentrated to a reddish oil (0.37 g) which was dissolved in EtOH (30 mL), treated with ethyl 4,4,4-trifluoroacetoacetate (0.30 mL) and zinc chloride (0.30 g), and heated at reflux for 12 h. The reaction mixture was poured into $H_2O$ (30 mL) and extracted with EtOAc (3×30 mL). The extracts were washed with $H_2O$ (2×30 mL) and brine (1×30 mL), combined, dried ($MgSO_4$), filtered, and concentrated. Purification by silica gel chromatography ($CH_2Cl_2$:MeOH, 12:1) afforded Compound 12 (0.41 g, 66%) as a yellow solid. Data for Compound 12: $^1$H NMR (400 MHz, DMSO-$d_6$) 12.5 (br s, 1H), 7.16 (s, 1H), 6.50 (s, 1H), 3.40 (m, 4H), 2.99 (t, J=6.2, 2H), 1.95 (m, 4H), 1.91 m, 2H).

EXAMPLE 6

8-Methyl-11-(trifluoromethyl)-9-pyridono[6,5-i] julolidine (Compound 13 of Scheme II)

In a 10 mL r.b. flask, a solution of Compound 12 (32 mg, 0.10 mmol) in DMF (1 mL) was treated with 60% NaH (6 mg, 0.1 mmol, 1 equiv) and treated with MeI (7 mL, 0.1 mmol, 1 equiv). The reaction mixture was stirred at rt for 6 h, poured into $H_2O$ (5 mL) and extracted with EtOAc (3×6 mL). The extracts were washed with $H_2O$ (1×5 mL) and brine (1×6 mL), combined, dried ($MgSO_4$), filtered, and concentrated. Purification by silica gel chromatography ($CH_2Cl_2$:MeOH, 30:1) afforded Compound 13 (3 mg, 10%) as a yellow solid. Data for Compound 13: $^1$H NMR (400 MHz, acetone-$d_6$) 7.14 (s, 1H), 6.44 (s, 1H), 3.60 (s, 3H), 3.38 (m, 4H), 2.98 (t, J=6.2, 2H), 1.95 (m, 4H), 1.91 (m, 2H).

EXAMPLE 7

7-Fluoro-1,2,3,4-tetrahydro-2,2-dimethyl-6-trifluoromethyl-8-pyridono[5,6-g]quinoline (Compound 105, Structure 20 of Scheme III, where $R^1$=$R^1$=Me, $R^3$=trifluoromethyl, $R^4$=F)

2-Methyl-3-butyn-2-yl(phenyl)amine (structure 16 of Scheme III, where $R^1$=$R^2$=Me)

In a 500 mL r.b., a solution of 2-methyl-3-butyn-2-ol (10.0 mL, 0.10 mol, 1.3 equiv) in $CH_2Cl_2$ (100 mL) was treated sequentially with Et$_3$N (15.0 mL, 0.107 mol, 1.4 equiv), acetic anhydride (11.6 mL, 0.12 mol, 1.5 equiv), and DMAP (0.61 g, 5.0 mmol, 5.0 mol %). The reaction mixture was stirred at rt for 2 h and poured into sat'd NH$_4$Cl (60 mL). The layers were separated. The aqueous layer was extracted with CH$_2$Cl$_2$ (2×100 mL). The organic layers were washed with 1 N HCl (2×100 mL), combined, dried (MgSO$_4$), filtered through a pad of Celite, and the volatiles were removed by distillation (<45° C. distillate). The residue was dissolved in THF (100 mL) and aniline (7.00 mL, 77 mmol) was added slowly via syringe, followed by CuCl (0.76 g, 10 mol%). The reaction mixture was heated to reflux for 3 h. The resulting red solution was allowed to cool to rt, the bulk of the volatiles were removed in vacuo, and the residue was diluted with EtOAc (120 mL). The solution was washed with sat'd NH$_4$Cl (2×100 mL) and brine (1×100 mL). The aqueous layers were extracted with EtOAc (2×100 mL). The combined organic layers were dried (MgSO$_4$), filtered, and concentrated. Purification by silica gel chromatography (hexane:EtOAc, 16:1) afforded 10.5 g (87%) of 2-methyl-3-butyn-2-yl(phenyl)amine as a pale yellow liquid. Data for 2-methyl-3-butyn-2-yl(phenyl)amine: $^1$H NMR (400 MHz, CDCl$_3$) 7.20 (t, J=7.7, 2H), 6.95 (d, J=7.7, 2H), 6.80 (t, J=7.7, 1H), 3.65 (br s, 1H), 2.36 (s, 1H), 1.61 (s, 6H).

1,2-Dihydro-2,2-dimethylquinoline (structure 17 of Scheme III where R$^1$=R$^2$=Me)

In a 1 L r.b., a solution of 2-methyl-3-butyn-2-yl(phenyl) amine (24.3 g, 152 mmol) in THF (200 mL) was treated with CuCl (1.70 g, 11 mol %) and heated at reflux for 14 h. The reaction mixture was cooled to rt, filtered, and the bulk of the THF was removed in vacuo. The residue was poured into sat'd NH$_4$Cl (200 mL) and extracted with EtOAc (3×250 mL). The extracts were washed with sat'd NH$_4$Cl (1×200 mL) and brine (1×200 mL), combined, dried (MgSO$_4$), filtered through a pad of Celite, and concentrated to an orange oil. Purification by silica gel chromatography (hexane:EtOAc, 40:1) afforded 18.0 g (74%) of the quinoline as a pale yellow oil. Data for 1,2-dihydro-2,2-dimethylquinoline: $^1$H NMR (400 MHz, CDCl$_3$) 6.95 (t, J=7.7, 1H), 6.87 (d, J=7.3, 1H), 6.57 (t, J=7.3, 1H), 6.40 (d, J=7.7, 1H), 6.25 (d, J=9.7, 1H), 5.46 (d, J=9.7, 1H), 3.63 (br s, 1H), 1.31 (s, 6H).

1,2,3,4-Tetrahydro-2,2-dimethylquinoline (structure 18 of Scheme III, where R$^1$=R$^2$=methyl)

In a 1 L r.b., a solution of the dihydroquinoline (16.2 g) in 1:1 EtOH:EtOAc (300 mL) was treated with 10% Pd/C (1.05 g) and stirred under an atmosphere of hydrogen. The reaction was monitored by $^1$H NMR and was complete after 4 h. The reaction mixture was purged, filtered through a pad of Celite, and the pad was rinsed with EtOAc (200 mL). Concentration of the filtrate afforded 16.2 g (99%) of the tetrahydroquinoline as a pale yellow oil. $^1$H NMR (400 MHz, CDCl$_3$) 6.98 (m, 2H), 6.60 (t, J=7.3, 1H), 6.44 (d, J=8.0, 1H), 2.77 (t, J=6.7, 2H), 1.70 (t, J=6.7, 2H), 1.21 (s, 6H).

1,2,3,4-Tetrahydro-2,2-dimethyl-7-nitroquinoline

In a 250 mL r.b., 1,2,3,4-tetrahydro-2,2-dimethylquinoline (6.06 g) in H$_2$SO$_4$ (40 mL) was cooled to −5° C. To this slurry, 90% HNO$_3$ (1.70 mL) was added dropwise over a 15 min period. The reaction mixture was stirred an additional 15 min and poured over ice (300 g). K$_2$CO$_3$ (100 g) was added slowly with vigorous stirring. The residue was extracted with CH$_2$Cl$_2$ (3×300 mL). The extracts were washed with H$_2$O (1×200 mL) and sat'd NaHCO$_3$ (1×100 mL), combined, dried (MgSO$_4$), filtered through pad of Celite, and concentrated. Purification by silica gel chromatography (hexane:EtOAc, 40:1 to 20:1 gradient) afforded 4.40 g (57%) of the product as an orange solid. Data for 1,2,3,4-tetrahydro-2,2-dimethyl-7-nitroquinoline: $^1$H NMR (400 MHz, CDCl$_3$) 7.39 (dd, J=7.9, 2.2, 1H), 7.27 (d, J=2.2, 1H), 7.04 (d, J=7.9, 1H), 3.95 (bs, 1H), 2.81 (t, J=6.7, 2H), 1.72 (t, J=6.7, 2H), 1.21 (s, 6H).

7-Amino-1,2,3,4-tetrahydro-2,2-dimethylquinoline (structure 19 of Scheme III, where R$^1$=R$^2$=Me)

In a 200-mL r.b. flask, a solution of 1,2,3,4-tetrahydro-2,2-dimethyl-7-nitroquinoline (1.00 g, 4.84 mmol) in 1:1 EtOH:EtOAc (40 mL) was treated with 10% Pd/C (0.20 g). The reaction mixture was de-gassed and fitted with a balloon of H$_2$. The reaction mixture was stirred for 6 h, de-gassed, and filtered through a pad of Celite. The pad was rinsed with EtOAc (300 mL). The filtrate was concentrated to afford 0.85 g (99%) of the crude aniline as a reddish oil. Data for 7-amino-1,2,3,4-tetrahydro-2,2-dimethylquinoline: $^1$H NMR (400 MHz, CDCl$_3$) 6.77 (d, J=7.9, 1H), 6.00 (dd, J=7.9, 2.2, 1H), 5.81 (d, J=2.2, 1H), 3.47 (bs, 1H) 3.40 (bs, 2H), 2.66 (t, J=6.7, 2H), 1.65 (t, J=6.7, 2H), 1.18 (s, 6H).

7-Fluoro-1,2,3,4-tetrahydro-2,2-dimethyl-6-trifluoromethyl-8-pyridono[5,6-g]quinoline (Compound 105, Structure 20 of Scheme III, where R$^1$, R$^2$=Me, R$^3$=trifluoromethyl, R$^4$=F)

This compound was prepared in a manner similar to that described for Compound 102 (EXAMPLE 2) from 7-amino-1,2,3,4-tetrahydro-2,2-dimethylquinoline (269 mg, 1.53 mmol), ethyl 2,4,4,4-tetrafluoro-3,3-dihydroxybutanoate (370 mg, 1.68 mmol, 1.1 equiv) and, ZnCl$_2$ (313 mg, 2.30 mmol, 1.5 equiv) in benzene (15 mL) followed by p-TsOH (72.8 mg, 0.383 mmol, 0.25 equiv) to afford 298 mg (62%) of Compound 105 after chromatography (CH$_2$Cl$_2$:EtOAc, 5:2). Data for Compound 105: R$_f$ 0.40 (5:2 CH$_2$Cl$_2$:EtOAc); $^1$H NMR (400 MHz, CDCl$_3$) 12.49 (s, 1H), 7.39 (s, 1H), 6.45 (s, 1H), 4.46 (s, 1H), 2.83 (t, J=6.5, 2H), 1.69 (t, J=6.6, 2H), 1.20 (s, 6H); Anal. Calc'd for C$_{15}$H$_{14}$F$_4$N$_2$O: C, 57.33;H, 4.49; N, 8.91. Found: C, 57.04;H, 4.72; N, 8.74.

EXAMPLE 8

6-Difluoromethyl-7-fluoro-1,2,3,4-tetrahydro-2,2-dimethyl-8-pyridono[5,6-g]quinoline (Compound 106, Structure 20 of Scheme III, where R$^1$=R$^2$=Me, R$^3$=difluoromethyl, R$^4$=F)

This compound was prepared in a manner similar to that described for Compound 102 (EXAMPLE 2) from 7-amino-1,2,3,4-tetrahydro-2,2-dimethylquinoline (150 mg, 0.851 mmol), ethyl 2,4,4-trifluoroacetoacetate (172 mg, 0.936 mmol, 1.1 equiv), and 4 angstrom molecular sieves (75 mgs, 50%), and ZnCl$_2$ (174 mg, 1.28 mmol, 1.5 equiv) in benzene (9.5 mL) followed by p-TsOH (40.5 mg, 0.213 mmol, 0.25 equiv) and EtOH (0.8 mL) to afford 116 mg (46%) of Compound 106 after chromatography (CH$_2$Cl$_2$:MeOH, 23:2) and recrystallization from EtOAc. Data for Compound 106: R$_f$ 0.33 (23:2 CH$_2$Cl$_2$:MeOH); $^1$H NMR (400 MHz, acetone-d$_6$) 10.93 (broad s, 1H), 7.52 (s, 1H), 7.33 (t, J=53.1, 1H), 6.48 (s, 1 H), 5.85 (broad s, 1H), 2.8–2.9 (m, 2H), 1.73 (t, J=6.7, 2H), 1.25 (s, 6H).

EXAMPLE 9

7-Fluoro-1,2,3,4-tetrahydro-2,2,9-trimethyl-6-trifluoromethyl-8-pyridono[5,6-g]quinoline (Compound 107, Structure 21of Scheme III, where R$^1$=R$^2$=Me, R$^3$=trifluoromethyl, R$^4$=F)

This compound was prepared in a manner similar to that described for Compound 103 (EXAMPLE 3) from Compound 105 (20 mg, 0.064 mmol), NaH (3.6 mg of a 60% mineral oil dispersion, 0.088 mmol, 1.4 equiv) and iodomethane (13 mg, 0.089 mmol, 1.4 equiv) in THF (1.3 mL) to afford 11 mg (51%) of Compound 107, a yellow solid, after chromatography ($CH_2Cl_2$:EtOAc, 19:1). Recrystallization from ethyl acetate afforded 5.6 mg (27%) of a yellow solid. Data for Compound 107: $R_f$ 0.29 ($CH_2Cl_2$:EtOAc, 19:1); $^1$H NMR (400 MHz, $CDCl_3$) 7.44 (s, 1H), 6.32 (s, 1H), 4.32 (broad s, 1H), 3.66 (s, 3H), 2.87 (t, J=6.6, 2H), 1.76 (t, J=6.7, 2H), 1.28 (s, 6H).

EXAMPLE 10

6-Difluoromethyl-7-fluoro-1,2,3,4-tetrahydro-2,2,9-trimethyl-8-pyridono[5,6-g]quinoline (Compound 108, Structure 21 of Scheme III, where $R^1=R^2$=Me, $R^3$=difluoromethyl, $R^4$=F)

This compound was prepared in a manner similar to that described for Compound 103 (EXAMPLE 3) from Compound 106 (40 mg, 0.14 mmol), NaH (6.8 mg of a 60% mineral oil dispersion, 0.17 mmol, 1.4 equiv) and iodomethane (25 mg, 0.18 mmol, 1.4 equiv) in THF (2.6 mL) to afford 40 mg (96%) of Compound 108, a yellow solid after chromatography ($CH_2Cl_2$:EtOAc, 19:1). Data for Compound 108: $R_f$ 0.53 ($CH_2Cl_2$:MeOH, 23:2); $^1$H NMR (400 MHz, acetone-$d_6$) 7.57 (s, 1H), 7.35 (t, J=53.0, 1H), 6.58 (s, 1H), 5.87 (broad s, 1H), 3.59 (s, 3H), 2.87 (t =6.6, 2H), 1.75 (t, J=6.6, 2H), 1.27 (s, 6H).

EXAMPLE 11

7-Fluoro-1,2,3,4-tetrahydro-1,2,2,9-tetramethyl-6-trifluoromethyl-8-pyridono[5,6-g]quinoline (Compound 109, Structure 22 of Scheme III, where $R^1=R^2$=Me, $R^3$=trifluoromethyl, $R^4$=F)

In a 10-mL r.b. flask, a mixture of Compound 107 (16 mg, 0.049 mmol) and paraformaldehyde (15 mg, 0.49 mmol, 10 equiv) in AcOH (3.0 mL) was treated with sodium cyanoborohydride (15 mg, 0.24 mmol, 4.8 equiv). The resultant mixture was stirred at rt for 18 h, then poured carefully into 25% aqueous NaOH (25 mL) and ice to make the mixture strongly alkaline (pH 11). The aqueous layer was extracted with $CH_2Cl_2$ (3×20 mL), and the combined organic layers were dried ($Na_2SO_4$), filtered, and concentrated to a yellow solid. Purification by flash chromatography ($CH_2Cl_2$:EtOAc, 20:1) afforded 15.2 mg (91%) of Compound 109, a yellow solid. Data for Compound 109: $R_f$ 0.74 (12:1 $CH_2Cl_2$:MeOH); $^1$H NMR (400 MHz, $CDCl_3$) 7.39 (s, 1H), 6.28 (s, 1H), 3.74 (s, 3H), 2.95 (s, 3H), 2.82 (t, J=6.4, 2H), 1.85 (t, J=6.4, 2H), 1.32 (s, 6H).

EXAMPLE 12

6-Difluoromethyl-7-fluoro-1,2,3,4-tetrahydro-1,2,2,9-tetramethyl-8-pyridono[5,6-g]quinoline (Compound 110, Structure 22 of Scheme III, where $R^1=R^2$=Me, $R^3$=difluoromethyl, $R^4$=F)

This compound was prepared in a manner similar to that described for the preparation of Compound 109 (EXAMPLE 11) from Compound 108 (18.4 mg, 0.0590 mmol), paraformaldehyde (17.7 mg, 0.592 mmol, 10 equiv) and sodium cyanoborohydride (17.9 mg, 0.286 mmol, 4.8 equiv) in AcOH (3.0 mL) to afford 11 mg (57%) of Compound 110, a yellow solid, after purification by flash chromatography ($CH_2Cl_2$:EtOAc, 19:1). Data for Compound 110: $^1$H NMR (400 MHz, acetone-$d_6$) 7.54 (s, 1H), 7.36 (t, J=7.36 (t, J=53.0, 1H), 6.48 (s, 1H), 3.71 (s, 3H), 3.02 (s, 3H), 2.75–2.85 (m, 2H), 1.87 (t, J=6.4, 2H), 1.34 (s, 6H).

EXAMPLE 13

7-Fluoro-1,2-dihydro-2,2,4-trimethyl-6-trifluoromethyl-8-pyridono[5,6-g]quinoline (Compound 111, structure 27 of Scheme IV, where $R^1$=H, $R^3$=trifluoromethyl, $R^4$=F)

1-tert-Butyloxycarbamoyl-3-nitrobenzene (structure 24 of Scheme IV, where $R^1$=H, $R^2$=t-BuO)

To a flame-dried 500 mL round-bottomed flask containing 3-nitroaniline (structure 23 of Scheme IV, where $R^1$=H) (20.0 g, 144.8 mmol) in 150 mL THF was added di-tert-butyl dicarbonate (31.60 g, 144.8 mmol, 1.00 equiv), and the mixture was cooled to 0° C. 4-N,N-Dimethylaminopyridine (19.46 g, 159.3 mmol, 1.10 equiv) was added portionwise, and the mixture was allowed to warm to rt overnight. Ethyl acetate (400 mL) was added, and the mixture was washed with 1M $NaHSO_4$(aq) (2×200 mL) and brine (200 mL), dried ($Na_2SO_4$), and concentrated under reduced pressure. Purification by flash column chromatography (silica gel, hexanes/ethyl acetate, 9:1) afforded 31.4 g (91%) of 1-tert-butyloxycarbamoyl-3-nitrobenzene as a white solid. Data for 1-tert-butyloxycarbamoyl-3-nitrobenzene: $^1$H NMR (400 MHz, $CDCl_3$) 8.31 (dd, 1H, J=2.2, 2.2, 2-H), 7.88 (dd, 1H, J=7.9, 1.5, 4-H), 7.69 (br d, 1H, J=7.8, 6-H), 7.44 (dd, 1H, J=8.3, 8.1, 5-H), 6.74 (br s, 1H, NH), 1.54 [s, 9H, $(CH_3)_3CO$)].

3-tert-Butyloxycarbamoylaniline (structure 25 of Scheme IV, where $R^1$=H, $R^2$=t-BuO)

To an oven-dried 1 L round-bottomed flask containing 1-tert-butyloxycarbamoyl-3-nitrobenzene (20.0 g, 83.9 mmol) in 500 mL 1:1 ethyl acetate/ethanol at rt was added 10% Pd on C (approx 1 mol %), and the mixture was stirred under an atmosphere of $H_2$ gas for 6 h. The reaction mixture was then filtered, and concentrated under diminished pressure to give 17.4 g quantitative) of 3-tert-butyloxycarbamoylaniline as a white oily solid. Data for 3-tert-butyloxycarbamoylaniline: $^1$H NMR (400 MHz, $CDCl_3$) 7.04 (dd, 1H, J=8.0, 8.0, 5-H), 6.98 (br s, 1H, NH), 6.53 (dd, 1H;J=7.9, 1.8, 4-H), 6.36 (m, 2H, 6,2-H), 3.66 (br s, 2H, $NH_2$), 1.51 [s, 9H, $(CH_3)3CO$)].

7-tert-Butyloxycarbamoyl-1,2-dihydro-2,2,4-trimethylquinoline (structure 26 of Scheme IV, where $R^1$=H, $R^2$=t-BuO)

To an oven-dried 1 L round-bottomed flask containing 3-tert-butyloxycarbamoylaniline (17.4 g, 83.5 mmol), $MgSO_4$ (50 g, 5 equiv), and 4-tert-butylcatechol (420 mg, 3 mol %) in 120 mL acetone (approx 0.75 M in the aniline) was added iodine (1.07 g, 5 mol %), and the mixture was heated to reflux for 8 h. The crude reaction mixture was then cooled to r.t., filtered through a bed of Celite™ on a fritted-glass funnel, rinsing with ethyl acetate, dried ($Na_2SO_4$), and concentrated under redcued pressure. Purification by flash column chromatography (silica gel, hexanes/ethyl acetate, gradient elution) afforded 19.9 g (82%) of 7-tert-butyloxycarbamoyl-1,2-dihydro-2,2,4-trimethylquinoline as a white solid, which was further purified by recrystallization from acetonitrile to give white needles. Data for 7-tert-butyloxycarbamoyl-1,2-dihydro-2, 2,4-trimethylquinoline: $^1$H NMR (400 MHz, $CDCl_3$) 6.93 (d, 1H, J=8.3, 5-H), 6.81 (br s, 1H, HNBoc), 6.34 (m, 2H, 6,8-H), 5.21 (d, 1H, J=0.9, 3-H), 3.71 (br s, 1H, NH), 1.94 (d, 3H, J=1.0, 4-$CH_3$), 1.50 [s, 9H, $(CH_3)_3CO$)], 1.24 [s, 6H, 2-$(CH_3)_2$].

7-Amino-1,2-dihydro-2,2,4-trimethylquinoline

To an oven-dried 25 mL round-bottomed flask containing 7-tert-butyloxycarbamoyl-1,2-dihydro-2,2,4- trimethylquinoline (400 mg, 1.38 mmol) in 2 mL dichloromethane at 0° C. was added trifluoroacetic acid (1.06 mL, 10 equiv), and the mixture was allowed to warm to r.t.. After 3 h at r.t., the reaction mixture was diluted with 50 mL dichloromethane, transferring to a 125 mL erlynmeyer flask, and cooled to 0° C. before neutralization to pH 8 with sat'd aqueous $NaHCO_3$. The biphasic mixture was transferred to a separatory funnel, the layers were separated, and the organic phase was dried ($Na_2SO_4$), and concentrated under reduced pressure to afford a light reddish oil. The crude material thus obtained was of greater than 98% purity by $^1$H NMR, and was carried on to the next step without further purification. While the 7-amino-quinoline obtained decomposed appreciably within a few hours upon standing at rt, ethanolic solutions could be stored at −20° C. for 2–3 days without substantial adverse effect on the subsequent reaction outcome. Typically however, the material was stored in bulk as the crystalline Boc-protected amine, and portions were hydrolysed as needed. Data for 7-amino-1,2-dihydro-2,2,4-trimethylquinoline: $^1$H NMR (400 MHz, $CDCl_3$) 6.86 (d, 1H, J=8.2, 5-H), 5.99 (dd, 1H, J=8.0, 2.3, 6-H), 5.79 (d, 1H, J=2.0, 8-H), 5.12 (d, 1H, J=1.4, 3-H), 3.53 (br, s 3H, $NH_2$, NH), 1.93 (d, 3H, J=1.2, 4-$CH_3$), 1.24 [s, 6H, 2-($CH_3$)$_2$].

7-Fluoro-1,2-dihydro-2,2,4-trimethyl-6-trifluoromethyl-8-pyridono[5 6-g]quinoline (Compound 111, structure 27 of Scheme IV, where $R^1$=H, $R^3$=trifluoromethyl, $R^4$=F)

This compound was prepared in a manner similar to that described for Compound 102 (EXAMPLE 2) from 7-amino-1,2-dihydro-2,2,4-trimethylquinoline (174 mg, 0.924 mmol), ethyl 2,4,4,4-tetrafluoro-3,3-dihydroxybutanoate (205 mg, 1.02 mmol, 1.1 equiv), 4 angstrom molecular sieves (90 mgs, 52%) and $ZnCl_2$ (189 mg, 1.39 mmol, 1.5 equiv) in benzene (9.2 mL) followed by p-TsOH (44 mg, 0.23 mmol, 0.25 equiv) to afford 235 mg (76%) of Compound 111 after chromatography ($CH_2Cl_2$:MeOH, 23:2). Data for Compound 111: $R_f$ 0.30 (23:2 $CH_2Cl_2$:MeOH); $^1$H NMR (400 MHz, $CDCl_3$) 12.58 (broad s, 1H), 7.40 (broad s, 1 H), 6.42 (s, 1H), 5.43 (s, 1H), 4.41 (broad s, 1H), 2.02 (d, J=1.1, 3H), 1.31 (s, 6H).

EXAMPLE 14

7-Fluoro-1,2,3,4-tetrahydro-2,2,4-trimethyl-6-trifluoromethyl-8-pyridono[5,6-g]quinoline
(Compound 112, Structure 30 of Scheme V, where $R^1$=H, $R^3$=trifluoromethyl, $R^4$=F)

A solution of Compound 111 (4.0 mg, 0.012 mmol) in EtOAc (0.49 mL) and EtOH (0.49 mL) containing 10% Pd/C (1 mg, 25%) was stirred under an atmosphere of $H_2$ for 12 h. The reaction mixture was filtered through a pad of Celite and purified by silica gel chromatography ($CH_2Cl_2$:EtOAc, 1:1) to afford 1.1 mg (28%) of Compound 112 as a yellow solid. Data for Compound 112: $R_f$ 0.44 (1:1 $CH_2Cl_2$:EtOAc); $^1$H NMR (400 MHz, $CDCl_3$) 11.94 (broad s, 1H), 7.56 (s, 1H), 6.38 (s, 1H), 4.38 (broad s, 1H), 2.90–3.00 (m, 1HO, 1.80 (dd, J=12.6, 4.5, 1H), 1.35–1.45 (m, 1H), 1.39 (d, J=6.7, 3H), 1.28 (s, 3H), 1.22 (S, 3H).

EXAMPLE 15

1,10-[1,3-dihydro-3-oxo-(2,1 -isoxazolyl)]-1,2,3,4-tetrahydro-2,2,4,10-tetramethyl-6-trifluoromethyl-8-pyridono[5,6-g]quinoline (Compound 113, structure 31 of of Scheme VI, where $R^3$=trifluoromethyl, $R^4$=H)

6-tert-Butyloxycarbamoyl-2-nitrotoluene (structure 24 of Scheme IV, where $R^1$=Me, $R^2$=t-BuO)

This compound was prepared from 2-methyl-3-nitroaniline (5.00 g, 32.8 mmol) in a manner similar to that described for 1-tert-butyloxycarbamoyl-3-nitrobenzne (EXAMPLE 13), affording 7.44 g (90%) of the desired carbamate as an off-white solid. Data for 6-tert-butyloxycarbamoyl-2-nitrotoluene: $^1$H NMR (400 MHz, $CDCl_3$) 7.98 (br d, 1H, J=8.0 Hz, 5-H), 7.51 (br d, 1H, J=8.1 Hz, 3-H), 7.28 (dd, 1H, J=7.6, 3.4 Hz, 4-H), 6.58 (br s, 1H, NH), 2.34 (s, 3H, 1-$CH_3$), 1.53 [s, 9H, ($CH_3$)$_3$CO)].

2-Amino-6-tert-butyloxycarbamoyltoluene (structure 25 of Scheme IV, where $R^1$=Me, $R^2$=t-BuO)

This compound was prepared from 6-tert-butyloxycarbamoyl-2-nitrotoluene (4.60 g, 18.2 mmol) in a manner similar to that described for 3-tert-butyloxycarbamoylaniline (EXAMPLE 13), affording 4.00 g (99%) of the desired aniline as a colorless oil. Data for 2-amino-6-tert-butyloxycarbamoyltoluene: $^1$H NMR (400 MHz, $CDCl_3$) 7.04 and 6.81 (br δ of ABq, 2H, $J_{AB}$=8.0 Hz, $J_A$=0 Hz, $J_B$=7.9 Hz, 4,5-H), 6.49 (d, 1H, J=8.3 Hz, 3-H), 6.26 (br s, 1H, NH), 3.61 (br s, 2H, $NH_2$), 2.02 (s, 3H, 1-$CH_3$), 1.51 [s, 9H, ($CH_3$)$_3$CO)].

7-tert-Butyloxycarbamoyl-1,2-dihydro-2,2,4,8-tetramethylquinoline (structure 26 of Scheme IV, where $R^1$=Me, $R^2$=t-BuO)

This compound was prepared from 2-amino-6-tert-butyloxycarbamoyltoluene (4.00 g, 18.0 mmol) in a manner similar to that described for 7-tert-butyloxycarbamoyl-1,2-dihydro-2,2,4-trimethylquinoline (EXAMPLE 13), affording 4.56 g (84%) of the desired dihydroquinoline as a white solid. Data for 7-tert-butyloxycarbamoyl-1,2-dihydro-2,2,4,8-tetramethylquinoline: $^1$H NMR (400 MHz, $CDCl_3$) 6.94 and 6.88 (br ABq, 2H, $J_{AB\cdot 8.3}$ Hz, 6,5-H), 6.16 (br s, 1H, HNBoc), 5.27 (s, 1H, 3-H), 3.61 [br s, 1H, ($CH_3$)$_2$CNH], 2.04 (s, 3H, 8-$CH_3$), 1.97 (s, 3H, 4-$CH_3$), 1.50 [s, 9H, ($CH_3$)$_3$CO)], 1.28 [s, 6H, 2-($CH_3$)$_2$].

7-Amino-1,2-dihydro-2,2,4,8-tetramethylquinoline

Removal of the Boc protective group of 7-tert-butyloxycarbamoyl-1,2-dihydro-2,2,4,8-tetramethylquinoline (400 mg, 1.32 mmol) was effected in the manner similar to that described for 7-amino-1,2-dihydro-2,2,4-trimethylquinoline (EXAMPLE 13), affording 267 mg (quantitative) of the desired aniline as a light reddish oil. Data for 7-amino-1,2-dihydro-2,2,4,8-tetramethylquinoline: $^1$H NMR (400 MHz, $CDCl_3$) 6.82 (d, 1H, J=8.2 Hz, 5-H), 6.08 (d, 1H, J=8.1 Hz, 6-H), 5.15 (d, 1H, J=1.2 Hz, 3-H), 3.56 (br s, 3H, $NH_2$, NH), 1.95 (D, 3H, J=1.2 Hz, 4-$CH_3$), 1.91 (s, 3H, 8-$CH_3$), 1.27 [s, 6H, 2-($CH_3$)$_2$].

1.2-Dihydro-2,2,4,10-tetramethyl-6-trifluoromethyl-8-pyridono[5,6-f]quinoline (structure 27 of Scheme IV, where $R^1$=Me, $R^2$=trifluoromethyl, $R^4$=H)

This compound was prepared in a manner similar to that described for Compound 102 (EXAMPLE 2) with 7-amino-1,2-dihydro-2,2,4,8-tetramethylquinoline (100 mg, 0.49 mmol) and ethyl 4,4,4-trifluoroacetoacetate (107 mL, 0.73 mmol, 1.5 equiv), affording 75 mg (47%) of the desired 2-quinolone as a fluorescent-yellow solid. Data for 1,2-dihydro-2,2,4,10-tetramethyl-6-trifluoromethyl-8-pyridono[5,6-f]quinoline: $^1$H NMR (400 MHz, $CDCl_3$) 9.23 (br s, 1H, CONH), 7.37 (s, 1H, 5-H), 6.67 (s, 1H, 7-H), 5.45 (s, 1H, 3-H), 4.14 [br s, 1H, ($CH_3$)$_2$CNH], 2.12 (s, 3H, 10-$CH_3$), 2.04 (d, 3H, J=1.1 Hz, 4-$CH_3$), 1.37 [s, 6H, 2-($CH_3$)$_2$].

1,2,3,4-Tetrahydro-2,2,4,10-tetramethyl-6-trifluoromethyl-8-pyridono[5,6-g]quinoline (structure 30 of Scheme V, where $R^1$=Me, $R^2$=trifluoromethyl, $R^4$=H)

To a 50-mL round-bottomed flask containing 1,2-dihydro-2,2,4,10-tetramethyl-6-trifluoromethyl-8-pyridono[5,6-f]

quinoline (421 mg, 1.31 mmol) in 5 mL 1,2-dichloroethane was added triethylsilane (1.04 mL, 6.53 mmol, 5.0 equiv) and trifluoroacetic acid (0.50 mL, 6.53 mmol, 5.00 equiv), and the mixture was heated to reflux using an oil bath. After 12 h, the mixture was cooled to 0° C. and quenced by the addition of 25 mL sat'd aqueous $NaHCO_3$. The resultant biphasic mixture was extracted with EtOAc (50 mL), and the organic solution was washed with 25 mL brine and dried over $Na_2SO_4$. The solvent was removed under reduced pressure, and the residue was purified by flash column chromatography (silica gel, hexanes/EtOAc, 2:1) affording 398 mg (94%) of the desired 3,4-saturated analogue as a pale fluorescent-yellow solid. Data for 1,2,3,4-tetrahydro-2,2,4,10-tetramethyl-6-trifluoromethyl-8-pyridono[5,6-g]quinoline: mp 239–40° C., $^1$H NMR (400 MHz, $CDCl_3$) 9.70 (br s, 1H, CONH), 7.50 (s, 1H, 5-H), 6.68 (s, 1H, 7-H), 4.13 [br s, 1H, $(CH_3)_2CNH$], 3.00 (ddq, 1H, J=12.9, 12.4, 6.3 Hz, 4-H), 2.15 (s, 3H, 10-$CH_3$), 1.83 and 1.46 [dd of ABq, 2H, $J_{AB}$=13.0 Hz, $J_A$=5.3, 1.6 Hz (3H$_{eq}$), $J_B$=12.9, 0 Hz (3-H$_{ax}$)], 1.40 (d, 3H, J=6.6 Hz, 4-$CH_3$), 1.36 and 1.25 [2s, 2×3H, 2-$(CH_3)_2$]. $^{13}$C NMR (100 MHz, $CDCl_3$) δ162.5, 144.9, 139.1, 137.1, 124.3, 122.7, 120.9, 113.8, 105.7, 101.6, 50.2, 43.5, 31.8, 28.9, 27.6, 20.1, 9.7. Anal. Calcd for $C_{17}H_{19}F_3N_2O$: C, 62.95;H, 5.90; N, 8.64. Found: C, 63.02;H, 6.01; N, 8.48.

1,10-[1,3-dihydro-3-oxo-(2,1-isoxazolyl)]-1,2,3,4-tetrahydro-2,2,4-trimethyl-6-trifluoromethyl-8-pyridonol[5,6-g]quinoline (Compound 113)

To a 10-mL round-bottomed flask containing 1,2,3,4-tetrahydro-2,2,4,10-tetramethyl-6-trifluoromethyl-8-pyridono[5,6-g]quinoline (50.0 mg, 0.15 mmol) in 1.5 mL $CH_3CN$ at rt was added 0.8 mL 30% aqueous $H_2O_2$ and 0.5 mL peracetic acid. The mixture was allowed to stir at rt 24 h, and was then transferred to a separatory funnel containing 40 mL $CH_2Cl_2$, 20 mL 10% aqueous $Na_2S_2O_3$ and 20 mL sat'd aqueous $NaHCO_3$). The layers were separated, and the organic solution was washed with 20 mL brine and dried over $Na_2SO_4$. The solvent was removed under reduced pressure, and the residue was purified by preparative TLC (silica gel, 500 mm, hexanes/EtOAc, 1:1) to give 22.3 mg (41%) of the oxo-isoxazolyl-derivative as a bright purple solid. Data for Compound 113: $^1$H NMR (400 MHz, $CDCl_3$) 9.70 (br s, 1H, CONH), 7.15 (s, 1H, 5-H), 6.58 (s, 1H, 7-H), 3.08 (m, 1H, 4-H), 2.13 and 2.07 [dd of ABq, 2H, $J_{AB}$=13.0 Hz, $J_A$=5.3, 1.6 Hz (3-H$_{eq}$), $J_B$=12.9, 0 Hz (3-H$_{ax}$)], 1.61 and 1.59 [2s, 2×3H, 2-$(CH_3)_2$], 1.46 (d, 3H, J=6.6 Hz, 4-$CH_3$).

EXAMPLE 16

7-Fluoro-1,2-dihydro-2,2,4, 10-tetramethyl-6-trifluoromethyl-8-pyridono[5,6-g]quinoline
(Compound 114, structure 27 of Scheme IV, where $R^1$=Me, $R^3$=trifluoromethyl, $R^4$=F)

This compound was prepared in manner similar to that described for Compound 102 (EXAMPLE 2) from 7-amino-1,2-dihydro-2,2,4,8-tetramethylquinoline (242 mg, 1.19 mmol) to afford Compound 114 (206 mg, 51%) as a yellow solid. Data for Compound 114: $^1$H NMR (400 MHz, $CDCl_3$) 9.78 (br s, 1H, CONH), 7.40 (s, 1H, 5-H), 5.46 (s, 1H, 3-H), 4.10 [br s, 1H, $(CH_3)_2CNH$], 2.16 (s, 3H, 10-$CH_3$), 2.04 (s, 3H, 4-$CH_3$), 1.37 ppm [s, 6H, 2-$(CH_3)_2$].

EXAMPLE 17

7-Fluoro-1,2,3,4-tetrahydro-2,2,4,10-tetramethyl-6-trifluoromethyl-8-pyridono[5,6-g]quinoline
(Compound 115, structure 30 of Scheme V, where $R^1$=Me, $R^3$=trifluoromethyl, $R^4$=F)

This compound was prepared in a manner similar to that described for 1,2,3,4-tetrahydro-2,2,4,10-tetramethyl-6-trifluoromethyl-8-pyridono[5,6-g]quinoline (EXAMPLE 15) from Compound 114 (84 mg, 0.25 mmol), affording Compound 115 (57 mg, 68%) as a yellow solid. Data for Compound 115: $^1$H NMR (400 MHz, $CDCl_3$) 10.21 (br s, 1H, CONH), 7.52 (s, 1H, 5-H), 4.06 [br s, 1H, $(CH_3)_2CNH$], 3.00 (ddq, 1H, J=12.9, 12.4, 6.3 Hz, 4-H), 2.19 (s, 3H, 10-$CH_3$), 1.83 and 1.46 [dd of ABq, 2H, $J_{AB}$=13.0 Hz, $J_A$=5.3, 1.6 Hz (3-H$_{eq)}$, $_{JB}$=12.9, 0 Hz (3-H$_{ax}$)], 1.39 (d, 3H, J=6.6 Hz, 4-$CH_3$), 1.36 and 1.24 [2s, 2×3H, 2-$(CH_3)_2$].

EXAMPLE 18

7-Fluoro-1,2,3,4-tetrahydro-2,2,4,9,10-pentamethyl-6-trifluoromethyl-8-pyridono[5,6-g]quinoline
(Compound 116, structure 32 of Scheme VII, where $R^1$=Me, $R^3$=trifluoromethyl, $R^4$=F)

This compound was prepared from 7-fluoro-1,2,3,4-tetrahydro-2,2,4,10-tetramethyl-6-trifluoromethyl-8-pyridono[5,6-g]quinoline in the manner previously described for the methylation of the amide nitrogen (EXAMPLE 3) from Compound 115 (21 mg, 0.06 mmol), affording Compound 116 (18 mg, 85%) as a yellow solid. Data for Compound 116: $^1$H NMR (400 MHz, $CDCl_3$) 7.67 (s, 1H, 5-H), 4.13 (s, 3H, 9-$CH_3$), 3.98 [br s, 1H, $(CH_3)_2CNH$], 3.00 (ddq, 1H, J=12.9, 12.4, 6.3 Hz, 4-H), 2.41 (s, 3H, 10-$CH_3$), 1.83 and 1.54 [dd of ABq, 2H, $J_{AB}$=13.0 Hz, $J_A$=5.3, 1.6 Hz (3-H$_{eq}$), $J_B$=12.9, 0 Hz (3-H$_{ax}$)], 1.45 (d, 3H, J=6.6 Hz, 4-$CH_3$), 1.36 and 1.25 [2s, 2×3H, 2-$(CH_3)_2$].

EXAMPLE 19

7-Fluoro-1,2,3,4-tetrahydro-1,2,2,4,10-pentamethyl-6-trifluoromethyl-8-pyridono[5,6-g]quinoline
(Compound 117, structure 33 of Scheme VII, where $R^1$=Me, $R^3$=trifluoromethyl, $R^4$=F)

This compound was prepared from 7-fluoro-1,2,3,4-tetrahydro-2,2,4,10-tetramethyl-6-trifluoromethyl-8-pyridono[5,6-g]quinoline (18 mg, 0.05 mmol) in the manner previously described for the methylation of the quinoline nitrogen (EXAMPLE 11), affording Compound 117 (17 mg, 91%) as a yellow solid. Data for Compound 117: $^1$H NMR (400 MHz, $CDCl_3$) 10.34 (br s, 1H, CONH), 7.53 (s, 1H, 5-H), 3.62 (s, 3H, 1-$CH_3$), 3.00 (ddq, 1H, J=12.9, 12.4, 6.3 Hz, 4-H), 2.21 (s, 3H, 10-$CH_3$), 1.82 and 1.42 [dd of ABq, 2H, $J_{AB}$=13.0 Hz, $J_A$5.3, 1.6 Hz (3-H$_{eq}$), $J_B$=12.9, 0 Hz (3-H$_{ax}$)], 1.45 (d, 3H, J=6.6 Hz, 4-$CH_3$), 1.33 and 1.25 [2s, 2×3H, 2-$(CH_3)_2$].

EXAMPLE 20

1,2,3,4-Tetrahydro-1-hydroxy-2,2-dimethyl-6-trifluoromethyl-8-pyridono[5,6-g]quinoline
(Compound 118, structure 35 of Scheme VIII, where $R^1$=$R^2$=Me, $R^3$=trifluoromethyl, $R^4$=H)

1,2,3,4-Tetrahydro-2,2-dimethyl-6-trifluoromethyl-8-pyridono[5,6-g]quinoline (structure 20 of Scheme III, where $R^1$=$R^2$=Me, $R^3$=trifluoromethyl, $R^4$=H)

In a 50-mL r.b. flask, a solution of the 7-amino-1,2,3,4-tetrahydro-2,2-dimethylquinoline (EXAMPLE 7) (0.85 g) in EtOH (10 mL) was treated with ethyl 4,4,4-trifluoroacetoacetate (0.70 mL, 4.8 mmol) and $ZnCl_2$ (0.96 g, 7.0 mmol, 1.5 equiv) and heated to reflux for 18 h. Two major products are observed by TLC (30:1 $CH_2CH_2$:MeOH, $R_f$ 0.85 and $R_f$ 0.35). The reaction mixture was allowed to cool to rt and the bulk of the solvent was removed in vacuo. The residue was dissolved in EtOAc (100 mL) and washed with H$_2$O (3×80 mL) and brine (1×100 mL). The aqueous layers were extracted with EtOAc (2×100 mL). The combined organic layers were dried (MgSO$_4$), filtered through a pad of Celite, and the pad was rinsed with EtOAc (200 mL). The filtrate was concentrated and purified by silica gel chromatography (CH$_2$Cl$_2$:MeOH, 60:1 to 15:1 gradient). The lower major band afforded 0.74 g (52%) of 1,2,3,4-tetrahydro-2,2-dimethyl-6-trifluoromethyl-8-pyridono[5,6-g]quinoline as a yellow powder. Data for 1,2,3,4-tetrahydro-2,2-dimethyl-6-trifluoromethyl-8-pyridono[5,6-g]quinoline: $^1$H NMR (400 MHz, DMSO d$_6$) 11.70 (s, 1H), 7.18 (s, 1H), 6.85 (s, 1H), 6.35 (s, 1H), 2.65 (t, J=6.6, 2H), 1.61 (t, J=6.6, 2H), 1.17 (s, 6H).

1,2,3,4-Tetrahydro-1-hydroxy-2.2-dimethyl-6-trifluoromethyl-8-pyridono[5,6-g]quinoline (Compound 118, structure 35 of Scheme VIII, where R$^1$=R$^2$=Me, R$^3$=trifluoromethyl, R$^4$=H)

To a 10-mL round-bottomed flask containing 1,2,3,4-tetrahydro-2,2-dimethyl-6-trifluoromethyl-8-pyridono[5,6-g]quinoline (40 mg, 0.13 mmol) in 1.0 mL CH$_3$CN at rt was added 0.5 mL 30% aqueous H$_2$O$_2$ and 0.3 mL peracetic acid. The mixture was allowed to stir at rt 24 h, and was then transferred to a separatory funnel containing 30 mL CH$_2$Cl$_2$, 15 mL 10% aqueous Na$_2$S$_2$O$_3$ and 15 mL sat'd aqueous NaHCO$_3$). The layers were separated, and the organic solution was washed with 15 mL brine and dried over Na$_2$SO$_4$. The solvent was removed under reduced pressure, and the residue was purified by preparative TLC (silica gel, 500 mm, hexanes,EtOAc, 1:1) to give 27 mg (65%) of the N-hydroxy-derivative as a bright purple solid. Data for Compond 118: $^1$H NMR (400 MHz, CDCl$_3$) 9.88 (br s, 1H, CONH), 7.26 (s, 1H, 5-H), 7.14 (s, 1H, 7-H), 6.50 (s, 1H, 10-H) 2.96 (dd, 2H, J=7.0, 6.1, 4-H), 2.23 (dd, 2H, J=6.8, 6.8, 3-H), 1.32 [s, 6H, 2-(CH$_3$)$_2$].

EXAMPLE 21

1,2,3,4-Tetrahydro-1-hydroxy-2,2,9-trimethyl-6-trifluoromethyl-8-pyridono[5,6-g]quinoline (Compound 119, structure 36 of Scheme VIII, where R$^1$=R$^2$=Me, R$^3$=trifluoromethyl, R$^4$=H)

This compound was prepared by the methylation of 1,2,3,4-tetrahydro-1-hydroxy-2,2-dimethyl-6-trifluoromethyl-8-pyridono[5,6-g]quinoline (16 mg, 0.05 mmol) as previously described (EXAMPLE 2), affording 12 mg (73%) of the methylated derivative as a bright purple solid. Data for Compound 119: $^1$H NMR (400 MHz, CDCl$_3$) 7.26 (s, 1H, 5-H), 7.18 (s, 1H, 7-H), 6.44 (s, 1H, 10-H) 3.97 (s, 3H, 9-CH$_3$), 2.90 (dd, 2H, J 7.0, 6.1, 4-H), 2.21 (dd, 2H, J=6.8, 6.8, 3-H), 1.58 [s, 6H, 2-(CH$_3$)$_2$].

EXAMPLE 22

2,2-Diethyl-7-fluoro-1,2,3,4-tetrahydro-6-trifluoromethyl-8-pyridono[5,6-g]quinoline (Compound 120, Structure 20 of Scheme III, where R$^1$=R$^2$=Et, R$^3$=trifluoromethyl, R$^4$=F)

3-Ethylpent-1-yn-3-yl acetate (structure 14 of Scheme III, where R$^1$=R$^2$=Et)

In a 250-mL r.b., a solution of 3-ethyl-1-pentyn-3-ol (11.5 g, 102 mmol) in pyridine (10.2 mL) was treated sequentially with Et$_3$N (15.0 mL, 0.107 mol, 1.4 equiv), acetic anhydride (13.5 mL, 143 mmol, 1.4 equiv), and DMAP (1.25 g, 10.2 mmol, 10.0 mol %). The reaction mixture was stirred at rt for 5 d, then treated with MeOH (5 mL) and stirred for 1 h. The mixture was partitioned between ether (100 mL) and water (100 mL), and the aqueous layer was extracted with ether (100 mL). The organic layers were washed sequentially with 2 N NaHSO$_4$ and brine (50 mL), dried (MgSO$_4$), filtered, and concentrated. Distillation under reduced pressure afforded 11.8 g (58.8%) 3-ethylpent-1-yn-3-yl acetate, a colorless oil, bp 38–39° C. @ 15 mm Hg. Data for 3-ethylpent-1-yn-3-yl acetate: $^1$H NMR (400 MHz, CDCl$_3$) 2.54 (s, 1 H), 2.03 (s, 3H), 1.96–2.08 (m, 2H), 1.84–1.95 (m, 2H), 0.97 (t, J=7.4, 6H).

2-Ethyl-1-pentyn-3-yl(phenyl)amine (structure 16 of Scheme III, where R$^1$=R$^2$=Et)

This compound was prepared in a manner similar to that described for Compound 4 (Example 1) from aniline (4.10 g, 44.0 mmol, 1.1 equiv), CuCl (0.396 g, 4.00 mmol, 10 mol %), 3-ethylpent-1-yn-3-yl acetate (6.17 g, 40 mmol) and Et$_3$N (4.45 g, 44.0 mmol, 1.1 equiv) in THF (100 mL) to afford 5.11 g (68.2%) of 2-ethyl-1-pentyn-3-yl(phenyl) amine after flash chromatography (hexanes:EtOAc, 16:1). Data for 2-ethyl-1-pentyn-3-yl(phenyl)amine: R$_f$ 0.28 (16:1 hexanes:EtOAc); $^1$H NMR (400 MHz, CDCl$_3$) 7.15–7.22 (m, 2H), 6.96 (dd, J=8.5, 1.0, 2H), 6.78 (t, J=7.4, 1H), 3.58 (broad s, 1H), 2.44 (s, 1H), 1.75–1.94 (m, 4H), 1.02 (t, J=7.5, 6H).

2.2-Diethyl-1,2-dihydroquinoline (structure 17 of Scheme III, where R$^1$=R$^2$=Et)

This compound was prepared in a manner similar to that described for 1,2-Dihydro-2,2-dimethylquinoline (structure 17 of Scheme III, where R$^1$=R$^2$=Me) from 2-ethyl-1-pentyn-3-yl(phenyl)amine (3.00 g, 16.0 mmol) and CuCl (0.190 g, 1.92 mmol) in THF to afford 1.51 g (50%) of 2,2-diethyl-1,2-dihydroquinoline after flash chromatography (hexanes:EtOAc, 16:1). Data for 2,2-diethyl-1,2-dihydroquinoline: R$_f$ 0.44 (16:1 hexanes:EtOAc; $^1$H NMR (400 MHz, CDCl$_3$) 6.85–6.95 (m, 1H), 6.81 (d, J=7.3, 1H), 6.48 (t, J=7.3, 1H), 6.36 (d, J=9.9, 1H), 5.21 (d, J=9.9, 1H), 3.39 (broad s, 1H), 1.35–1.55 (m, 4H), 0.93 (t, J=7.5, 6H).

2,2-Diethyl-1,2,3,4-tetrahydroquinoline (structure 18 of Scheme III, where R$^1$=R$^2$=Et)

This compound was prepared in a manner similar to that described for 1,2,3,4-tetrahydro-2,2-dimethylquinoline (structure 18 of Scheme III, where R$^1$=R$^2$=Me) from 2,2-diethyl-1,2-dihydroquinoline (1.46 g, 7.80 mmol) and 10% Pd/C (146 mg, 10% by weight) in EtOAc (18.7 mL) to afford 1.04 g (70%) 2,2-diethyl-1,2,3,4-tetrahydroquinoline after flash chromatography (hexanes:EtOAc, 97:3). Data for 2,2-diethyl-1,2,3,4-tetrahydroquinoline: R$_f$ 0.43 (24:1 hexanes-:ethyl acetate); $^1$H NMR (400 MHz, CDCl$_3$) 6.90–7.00 (m, 2H), 6.57 (td, J=7.3, 1.0, 1H), 6.46 (dd, J=8.4, 1.0, 1H), 3.63 (broad s, 1H), 2.72 (t, J=6.7, 2H), 1.69 (t, J=6.7, 2H), 1.38–1.53 (m, 4H), 0.86 (t,J=7.4, 6H).

2,2-Diethyl-1,2,3,4-tetrahydro-7-nitroquinoline

This compound was prepared in a manner similar to that described for 1,2,3,4-tetrahydro-2,2-dimethyl-7-nitroquinoline (Scheme III) from for 2,2-diethyl-1,2,3,4-tetrahydroquinoline (0.955 g, 5.04 mmol) and fuming HNO$_3$ (0.32 g, 5.0 mmol) in concentrated sulfuric acid (10 mL) to afford 0.811 g (69%) of 2,2-diethyl-1,2,3,4-tetrahydro-7-nitroquinoline after chromatography (hexanes:EtOAc, 24:1). Data for 2,2-diethyl-1,2,3,4-tetrahydro-7-nitroquinoline: R$_f$ 0.43 (24:1 hexanes:ethyl acetate); $^1$H NMR (400 MHz, CDCl$_3$) 7.38 (dd, J=8.3, 2.3, 1H), 7.29 (d, J=2.3, 1H), 7.04 (d, J=8.3, 1H), 4.00 (broad s, 1H), 2.78 (t, J=6.7 2H), 1.71 (t, J=6.7, 2H), 1.38–1.58 (m, 4H), 0.88 (t, J=7.4, 6H).

7-Amino-2,2-diethyl-1,2,3,4-tetrahydroquinoline (structure 19 of Scheme III, where $R^1=R^2=Et$)

This compound was prepared in a manner similar to that described for 7-amino-1,2,3,4-tetrahydro-2,2-dimethylquinoline (structure 19 of Scheme III, where $R^1=R^2=Me$) from for 2,2-diethyl-1,2,3,4-tetrahydro-7-nitroquinoline (0.311 g, 1.33 mmol) and 10% Pd/C (31 mg, 10% by weight) in EtOAc (4.0 mL) and EtOH (4.0 mL) to afford 255 mg (94%) of 7-amino-2,2-diethyl-1,2,3,4-tetrahydroquinoline. Data for 7-amino-2,2-diethyl-1,2,3,4-tetrahydroquinoline: $R_f$ 0.26 (4:1 hexanes:ethyl acetate); $^1$H NMR (400 MHz, CDCl$_3$) 6.77 (d, J=7.9H, 1H), 6.12 (dd, J=7.9,1.9,1H), 6.05 (d,J=2.0,1H), 4.68 (broad s,3H), 2.62 (t, J=6.7, 2H), 1.67 (t, J=6.7, 2H), 1.38–1.55 (m, 4H), 0.85 (t, J=7.4, 6H). P 2,2-Diethyl-7-fluoro-1,2,3,4-tetrahydro-6-trifluoromethyl-8-pyridono[5,6-g]quinoline (Compound 120, Structure 20 of Scheme III, where $R^1$, $R^2$=Et, $R^3$=trifluoromethyl, $R^4$=F)

This compound was prepared in a manner similar to that described for Compound 102 (EXAMPLE 2) from 7-amino-2,2-diethyl-1,2,3,4-tetrahydroquinoline (0.100 g, 0.489 mmol), ethyl 2,4,4,4-tetrafluoro-3,3-dihydroxybutanoate (109 mg, 0.538 mmol, 1.1 equiv) and, ZnCl$_2$ (100 mg, 0.734 mmol, 1.5 equiv) in benzene (4.9 mL) followed by p-TsOH (23.2 mg, 0.122 mmol, 0.25 equiv) to afford 98 mg (58%) of Compound 120 after flash chromatography (CH$_2$Cl$_2$:EtOAc, 5:2). Data for Compound 120: $R_f$ 0.47 (5:2 CH$_2$Cl$_2$:EtOAc; $^1$H NMR (400 MHz, CDCl$_3$) 12.03 (broad s, 1H), 7.40 (s, 1H), 6.42 (s, 1H), 4.40 (s, 1H), 2.82 (t, J=6.6, 2 H), 1.74 (t, J=6.6, 2H), 1.40–1.60 (m, 4H), 0.93 (t, J=7.4, 6H).

EXAMPLE 23

(R/S)-4-Ethyl-1-formyl-1,2,3,4-tetrahydro-6-(trifluoromethyl)-8-pyridono[5,6-g]quinoline (Compound 121, structure 42 of Scheme IX, where R=H)

1,2,3,4-Tetrahydro-4-quinolinone

In a 200 mL r.b. flask was introduced aniline (9.78 mL, 0.107 mol), acrylic acid (7.36 mL, 0.107 mol) and toluene (100 mL). The reaction mixture was stirred and heated at 100° C. for 16 h, cooled to rt and the solvent was removed in vacuo to give 10.34 g (60%) of the desired intermediate carboxylic acid that was used directly without further purification for the next step.

In a 500 mL r.b. flask was introduced the acid (10.34 g, 0.064 mol) and polyphosphoric acid (200 mL). The reaction mixture was stirred and heated at 100° C. for 16 h. The reaction mixture was cooled to rt, poured onto 700 mL of a 1:1 mixture of ice/water and neutralized slowly with NaOH. The aqueous phase was extracted with ethyl acetate (3×200 mL), dried (Na$_2$SO$_4$) and the solvent was removed in vacuo to give a solid residue that was subjected to flash chromatography (silica gel, hexanes/ethyl acetate, 6:1) to afford 6.97 g (76%) of 1,2,3,4-tetrahydro-4-quinolinone. Data for 1,2,3,4-tetrahydro-4-quinolinone: $^1$H NMR (400 MHz, CDCl$_3$) δ7.84 (dd, J=7.9, 1.1, 1H), 7.28 (ddd, J=7.9, 7.9, 1.2, 1H), 6.72 (ddd, J=8.1, 8.1, 0.8, 1H), 6.66 (d,J=8.1, 1H), 4.49 (s, 1H), 3.56 (t, J=6.9, 2H), 2.69 (t, J=6.8, 2H).

1-tert-Butyloxycarbonyl-1,2,3,4-tetrahydro-4-quinolinone (structure 38 of Scheme IX)

To a stirred solution of Boc$_2$O (10.05 g, 0.046 mol) and 1,2,3,4-tetrahydro-4-quinolinone (6.16 g, 0.042 mol) in THF (100 mL) at 0° C. was added slowly DMAP (5.11 g, 0.042 mol) in 100 mL of THF. The reaction mixture was stirred overnight, then water (75 mL) was added and the mixture was extracted with ethyl acetate (2×200 mL). The organic phase was dried (Na$_2$SO$_4$) and the solvent was removed in vacuo to give a solid residue that was subjected to flash chromatography (silica gel, hexanes/ethyl acetate, 8:2) which afforded 8.5 g (82%) of 1-tert-butyloxycarbonyl-1,2,3,4-tetrahydro-4-quinolinone. Data for 1-tert-butyloxycarbonyl-1,2,3,4-tetrahydro-4-quinolinone: $^1$H NMR (400 MHz, CDCl$_3$) δ7.98 (dd, J=7.9, 1.7, 1H), 7.76 (d, J=8.4, 1H), 7.49 (ddd, J=7.5, 7.5, 1.7, 1H), 7.15 (ddd, J=8.0, 8.0, 0.9, 1H), 4.15 (t, J=6.3, 2H), 2.76 (t, J=6.6, 2H), 1.55 (s, 9H).

(RS-)1-tert-Butyloxycarbonyl-4-ethyl-1,2,3,4-tetrahydro-4-hydroxyquinoline

To a flame-dried 25-mL r.b. flask containing ethylmagnesium bromide (4.0 mL of a 3.0 M solution in Et$_2$O, 12.0 mmol, 3.0 equiv), at −10° C. was added dropwise a solution of 1-tert-butyloxycarbonyl-1,2,3,4-tetrahydro-4-quinolinone (1.0 g, 4.0 mmol) in Et$_2$O (4 mL). The reaction mixture was stirred at −10° C. for 15 min, then allowed to warm to rt over 10 min. A 1.0 M solution of NaHSO$_4$ (10 mL) was then rapidly added. The resulting biphasic mixture was extracted with EtOAc (3×10 mL), and the combined organic extracts were dried (Na$_2$SO$_4$) and concentrated under reduced pressure. The residue was purified by flash chromatography (silica gel, hexanes/EtOAc, 4:1), affording 800 mg (71%) of the desired product as a clear yellow oil ($R_f$ 0.14, hexanes/EtOAc, 4:1). Data for 1-tert-butoxycarbonyl-4-ethyl-1,2,3,4-tetrahydro-4-hydroxyquinoline: $^1$H NMR (400 MHz, CDCl$_3$) δ7.68 (d, 1H, J=8.4, 8-H), 7.47 (dd, 1H, J=7.9, 1.7, 5-H), 7.21 (ddd, 1H, J=7.4, 7.4, 1.6, 6-H), 7.09 (ddd, 1H, J=7.8, 7.8, 1.1, 7-H), 4.03 (ddd, 1H, J=12.9, 7.1, 4.7, 2-H), 3.47 (ddd, 1H, J=13.1, 8.6, 4.3, 2-H), 2.11 (ddd, 1H, J=13.5, 8.6, 4.8, 3-H), 1.86 (m, 3H, 3-H, CH$_2$CH$_3$), 1.52 [s, 9H, C(CH$_3$)$_3$], 0.89 (t, 3H, J=7.5, CH$_3$).

(R/S)-4-Ethyl-1,2,3,4-tetrahydroquinoline (structure 39 of Scheme IX)

To a flame-dried 100-mL r.b. flask containing 1-tert-butyloxycarbonyl-4-ethyl-1,2,3,4-tetrahydro-4-hydroxyquinoline (800 mg, 2.88 mmol ) in a 1:1 solution of EtOAc / EtOH (20 mL) at rt was added 10% Pd/C (approx. 1 mol %). After evacuation and flushing of the vessel three times with nitrogen, one drop of trifluoroacetic acid was added, the vessel evacuated once more, and the mixture stirred under an atmosphere of hydrogen for 16 h. The reaction mixture was then filtered, and concentrated under reduced pressure. The residue was transferred to a 25-mL rb flask with CH$_2$Cl$_2$ (3 mL) and stirred at rt. TFA (1.2 mL) was added and the reaction was vented and stirred for 2 h at rt. A solution of sat'd. NaHCO$_3$ (adjusted to pH 9 with 3.0 M NaOH) was added until the aqueous phase was approximately pH 9. The resulting aqueous phase was extracted with CH$_2$Cl$_2$ (3×10 mL), and the combined organic extracts were dried (Na$_2$SO$_4$), and concentrated under reduced pressure to yield 351 mg (71%) of a colorless oil, which turned blue on exposure to air ($R_f$ 0.40, hexanes/EtOAc, 2:1). Data for (R/S)-4-ethyl-1,2,3,4-tetrahydroquinoline: $^1$H NMR (400 MHz, CDCl$_3$) δ7.02 (d, 1H, J=7.6, 8-H), 6.96 (ddd, 1H, J=7.7, 7.7, 1.3, 7-H), 6.61 (ddd, 1H, J=8.2, 8.2, 1.0, 6-H), 6.47 (d, 1H, J=7.9, 5-H), 3.83 (br s, 1H, CH$_2$NH), 3.31 (ddd, 1H, J=11.3, 11.3, 3.6, 2-H), 3.25 (ddd, 1H, J=9.7, 9.7, 4.8, 2-H), 2.65 (dddd, 1H, J=10.1, 5.1, 5.1, 5.1, 4-H), 1.92 (dddd, 1H, J=9.6, 4.7, 4.7, 4.7, 3-H), 1.82 (m, 1H, 3-H), 1.74 (m, 1H, CH$_2$CH$_3$), 0.98 (t, 3H, J=7.4, CH$_3$).

(R/S)-7-Amino-4-ethyl-1,2,3,4-tetrahydroquinoline (structure 40 of Scheme IX)

A 25-mL rb flask containing (R/S)-4-ethyl-1,2,3,4-tetrahydroquinoline (340 mg, 2.1 mmol) was cooled to −10°

C., and conc. H$_2$SO$_4$ (5 mL) was added slowly. The resulting solution was warmed to rt to effect complete dissolution of the quinoline, then cooled again to −10° C. and stirred vigorously. Fuming HNO$_3$ (85 μL) was added dropwise, slowly, and the reaction mixture turned dark red. After 10 min, the reaction mixture was poured onto cracked ice and diluted with water (5 mL). Sat'd NaHCO$_3$ (80 mL) was added, and the pH was adjusted to pH 9 with 3.0 M NaOH. This aqueous phase was extracted with EtOAc (3×75 mL), and the combined extracts were dried (Na$_2$SO$_4$), and concentrated under reduced pressure to yield a dark red oil. This crude material was placed into a 250-mL rb flask with 1:1 EtOAc/EtOH (40 mL) and 10% Pd on C (approx. 1 mol %). The vessel was evacuated and flushed with nitrogen three times, then stirred under an atmosphere of hydrogen for 16 h, filtered, and concentrated under reduced pressure to yield a yellow oil, which was purified by flash chromatography (silica gel, CH$_2$Cl$_2$/methanol, 9:1), affording 210 mg (57 %) of the desired product as a dark yellow oil (R$_f$ 0.50, CH$_2$Cl$_2$/MeOH, 9:1). Data for (R/S)-7-amino-4-ethyl-1,2,3,4-tetrahydroquinoline: $^1$H NMR (400 MHz, CDCl$_3$) δ6.81 (d, 1H, J=8.1, 5-H), 6.02 (dd, 1H, J=8.0, 2.2, 6-H), 5.84 (d, 1H, J=2.3, 8-H), 3.48 (s, 2H, NH$_2$), 3.27 (ddd, 1H, J=11.1, 11.1, 3.5, 2-H), 3.20 (ddd, 1H, J=9.8, 5.3, 4.5, 2-H), 2.55 (dddd, 1H, J=10.2, 5.2, 5.2, 5.2, 4H), 1.90 (dddd, 1H, J=9.6, 9.6, 9.6, 4.7, 3-H), 1.72 (m, 2H, 3-H, CH$_2$CH$_3$), 1.48 (m, 1H, CH$_2$CH$_3$), 0.96 (t, 3H, J=7.4, CH$_3$).

(R/S)-4-Ethyl-1,2,3,4-tetrahydro-6-(trifluoromethyl)-8-pyridono[5,6-g]quinoline (structure 41 of Scheme IX)

To a flame-dried 100-mL rb flask containing 7-amino-4-ethyl-1,2,3,4-tetrahydroquinoline (210 mg, 1.19 mmol), in ethanol (20 mL), at rt, was added ethyl-4,4,4-trifluoroacetoacetate (190 μL, 1.31 mmol, 1.1 equiv) followed by ZnCl$_2$ (244 mg, 1.79 mmol, 1.5 equiv). The reaction mixture was heated to reflux for 6 h, at which point all starting material had been consumed (by TLC analysis). The reaction mixture was cooled to rt, and the solvent removed under reduced pressure. Dichloromethane (20 mL) was added and the organic phase washed with sat'd NaHCO$_3$ (2×10 mL) and brine (1×10 mL), then dried (Na$_2$SO$_4$), and concentrated under reduced pressure. This crude product was purified by flash chromatography (silica gel, CH$_2$Cl$_2$/MeOH, 15:1), affording 24.4 mg (7%) of the desired product as a yellow solid. Data for (R/S)-4-ethyl-1,2,3,4-tetrahydro-6-(trifluoromethyl)-8-pyridono[5,6-g] quinoline: R$_f$ 0.37, (CH$_2$Cl$_2$/MeOH, 9:1); $^1$H NMR (400 MHz, CD$_3$OD) δ7.31 (s, 1H, 5-H), 6.47 (s, 1H, 7-H), 6.37 (s, 1H, 10-H), 3.34 (m, 2H, 2-H), 2.70 (m, 1H, 4-H), 1.88 (m, 2H, 3-H), 1.62 (m, 2H, CH$_2$CH$_3$), 1.00 (t, 3H, J=7.5, CH$_3$).

(R/S)-4-Ethyl-1-formyl-1,2,3,4-tetrahydro-6-(trifluoromethyl)-8-pyridono[5,6-g]quinoline (Compound 121, structure 42, Scheme IX, where R=H)

In a 5 mL r.b. flask, a mixture of (R/S)-4-ethyl-1,2,3,4-tetrahydro-6-(trifluoromethyl)-8-pyridono[5,6-g]quinoline (27 mg, 0.091 mmol) in formic acid (0.14 mL, 3.6 mmol, 40 equiv) was treated with acetic anhydride (30 μL, 0.32 mmol, 3.5 equiv), and the reaction mixture was stirred at room temperature overnight. The reaction mixture was quenched with saturated aqueous NaHCO$_3$ (25 mL). The aqueous layer was extracted with EtOAc (3×25 mL), and the combined organic layers were dried (Na$_2$SO$_4$), filtered, and concentrated to 21 mg (70%) of Compound 121, a white solid. Data for Compound 121: R$_f$ 0.51 (11.5:1 CH$_2$CL$_2$:MeOH); $^1$H NMR (400 MHz, CDCl$_3$) δ12.40 (s, 1H, C(O)NH), 8.98 (s, 1H, C(O)H), 7.63 (s, 1H, 5-H), 7.21 (s, 1H, 10-H), 7.01 (s, 1H, 7-H), 3.85–3.95 (m, 1H, 2-H), 3.75–3.85 (m, 1H, 2-H), 2.75–2.85 (m, 1H, 4-H), 1.90–2.05 (m, 2H, 2×3-H), 1.70–1.80 (m, 1H, CHCH$_3$), 1.55–1.65 (m, 1H, CHCH$_3$), 1.02 (t, J=7.4 Hz, 3H, CH$_3$).

EXAMPLE 24

(R/S)-4-Ethyl-1,2,3,4-tetrahydro-1-(trifluoroacetyl)-6-(trifluoromethyl)-8-pyridono[5,6-g]quinoline (Compound 122, structure 42, Scheme IX, where R=CF$_3$)

In a 5.0 mL r.b. flask, a mixture of (R/S)-4-ethyl-1,2,3,4-tetrahydro-6-(trifluoromethyl)-8-pyridono[5,6-g]quinoline (11.3 mg, 0.038 mmol), triethylamine (6.4 μL, 0.046 mmol), and CH$_2$Cl$_2$ (2.0 mL) was treated with trifluoroacetic anhydride (6.5 μL, 0.046 mmol) and stirred for 24 h at rt. The mixture was then partitioned with H$_2$O (10 mL) and CH$_2$Cl$_2$ (10 mL). The aqueous layer was extracted with CH$_2$Cl$_2$ (2×15 mL), and the combined organic layers were washed with brine, dried (Na$_2$SO$_4$) filtered, and concentrated to a yellow solid. Purification by flash chromatography (2×15 cm column, hexane:EtOAc, 1:1) afforded 7.6 mg (50%) of Compound 122, a light yellow solid. Data for compound 122: R$_f$ 0.48 (11.5:1 CH$_2$Cl$_2$:MeOH); $^1$H NMR (400 MHz, CDCl$_3$) δ11.72 (broad s, 1H, C(O)NH), 7.77 (broad s, 1H, 10-H), 7.67 (s, 1H, 5-H), 7.08 (s, 1H, 7-H), 4.00–4.10 (m, 1H, 2-H), 3.72–3.82 (m, 1H, 2-H), 2.83–2.93 (m, 1H, 4-H), 2.19–2.29 (m, 1H, 3-H), 1.75–1.94 (m, 2H, 3-H, CHCH$_3$), 1.58–1.67 (m, 1H, CHCH$_3$), 1.00 (t, J=7.4 Hz, 3H, CH$_3$).

EXAMPLE 25

(R/S)-1-Acetyl-4-ethyl-1,2,3,4-tetrahydro-6-(trifluoromethyl)-8-pyridono[5,6-g]quinoline (Compound 123, structure 42, Scheme IX, where R=Me)

In a 25 mL r.b. flask, a mixture of (R/S)-4-ethyl-1,2,3,4-tetrahydro-6-(trifluoromethyl)-8-pyridono[5,6-g]quinoline (116 mg, 0.39 mmol, 1.0 equiv) and triethylamine (0.218 mL, 1.56 mmol, 4.0 equiv) in dichloroethane (3.0 mL) was treated with acetyl chloride (0.111 mL, 1.56 mmol, 4.0 equiv) dropwise, and stirred for 7 h. The mixture was partitioned with H$_2$O (25 mL) and CH$_2$Cl$_2$ (25 mL). The aqueous layers were extracted with CH$_2$Cl$_2$ (2×25 mL), and the combined extracts were washed with brine, dried (Na$_2$SO$_4$), filtered and concentrated to a yellow solid. The $^1$H NMR spectrum revealed that starting material remains. The crude material was treated with triethylamine (0.22 mL, 1.6 mmol, 4.0 equiv) and acetyl chloride (42 μL, 0.58 mmol, 1.5 equiv) in dichloroethane (7.0 mL). After 8 h, the mixture was partitioned with H$_2$O (25 mL) and CH$_2$Cl$_2$ (25 mL). The aqueous layers were extracted with CH$_2$Cl$_2$ (2×25 mL), and the combined extracts were washed with brine, dried (Na$_2$SO$_4$), filtered and concentrated to a yellow solid. The crude material (17.0 mg) was treated with K$_2$CO$_3$ (6.9 mg, 0.050 mmol, 1.0 equiv) in MeOH for 15 minutes. The reaction mixture was partitioned with CH$_2$Cl$_2$ (10 mL) and pH 7 phosphate buffer (10 mL), dried (Na$_2$SO$_4$), filtered, and concentrated to a yellow solid. Purification by semi-preparative HPLC (ODS reverse phase column, 3:1 MeOH:water) afforded 2.4 mg (14%) Compound 123, a white solid. Data for compound 123: R$_f$ 0.23 (1:1 hexane:EtOAc); $^1$H NMR (400 MHz, CDCl$_3$) δ11.25 (broad s, 1H, C(O)NH), 7.60 (broad s, 1H, 10-H), 7.58 (s, 1H, 5-H), 6.99 (s, 1H, 7-H), 3.88–3.98 (m, 1H, 2-H), 3.70–3.80 (m, 1H, 2-H), 2.70–2.80 (m, 1H, 4-H), 2.36 (s, 3H, C(O)CH$_3$), 2.05–2.12 (m, 1H, 3-H), 1.80–1.90 (m, 1H), 1.70–1.80 (m, 1H), 1.60–1.66 (m, 1H), 1.01 (t, J=7.4 Hz, 3H, CH$_3$).

EXAMPLE 26

(R/S)-4-Ethyl-1,2,3,4-tetrahydro-10-nitro-6-(trifluoromethyl)-8-pyridono[5,6-g]quinoline (Compound 124, structure 44 of Scheme X, where $R^1$=Et, $R^2$=H In a 15-mL r.b. flask, a mixture of (R/S)-4-ethyl-1,2,3,4-tetrahydro-6-(trifluoromethyl)-8-pyridono[5,6-g]quinoline (64.7 mg, 0.22 mmol) in $H_2SO_4$ (2.0 mL) was cooled to 0° C. Fuming $HNO_3$ (20.0 μL, 0.44 mmol, 2 equiv) diluted in $H_2SO_4$ (0.4 mL) was added over 1.2 min, and warmed to rt over a period of 10 min. The mixture was poured into a mixture of ice (25 g) and $K_2CO_3$ (7.0 g). The aqueous layer was extracted with $CH_2Cl_2$ (2×25 mL), and the combined organic layers were washed with pH 7 phosphate buffer, dried ($MgSO_4$), filtered, and concentrated to a yellow solid. Purification by flash chromatography (2×15 cm column, $CH_2Cl_2$:EtOAc, 9:1) afforded 5.1 mg (6%) of Compound 124, an orange solid. Data for Compound 124: $R_f$ 0.29 (9:1 $CH_2Cl_2$:EtOAc); $^1$H NMR (400 MHz, $CDCl_3$) δ12.38 (broad s, 1H, C(O)NH), 9.82 (broad s, 1H, NH), 7.48 (s, 1H, 5-H), 6.84 (s, 1H, 7-H), 3.62–3.70 (m, 2 H, 2×2-H), 2.75–2.84 (m, 1H, 4-H), 1.92–2.02 (m, 2H, 2×3-H), 1.59–1.67 (m, 2H, $CH_2CH_3$), 1.01 (t, J=7.4 Hz, 3H, $CH_3$).

EXAMPLE 27

1,2,3,4-Tetrahydro-2,2-dimethyl-10-nitro-6-(trifluoromethyl)-8-pyridono[5,6-g]quinoline (Compound 125, structure 44 of Scheme X, where $R^1$=H, $R^2$=Me) and 1,2,3,4-Tetrahydro-2,2-dimethyl-7,10-dinitro-6-(trifluoromethyl)-8-pyridono[5,6-g]quinoline (Compound 126, structure 45 of Scheme X, where $R^1$=H, $R^2$=Me)

1,2,3,4-Tetrahydro-2,2-dimethyl-6-trifluoromethyl-8-pyridono[5,6-g]quinoline (structure 20 of Scheme III, where $R^1$, $R^2$=Me, $R^3$=trifluoromethyl, $R^4$=H)

This compound was prepared in a manner similar to that described for Compound 102 (EXAMPLE 2) from 7-amino-1,2,3,4-tetrahydro-2,2-dimethylquinoline (2.35 g, 12 mmol), ethyl 4,4,4-trifluoroacetoacetate (2.15 g, 13 mmol, 1.1 equiv) and, $ZnCl_2$ (2.74 g, 20 mmol, 1.7 equiv) to afford 1.91 g (48%) of 1,2,3,4-tetrahydro-2,2-dimethyl-6-trifluoromethyl-8-pyridono[5,6-g]quinoline. Data for 1,2,3,4-tetrahydro-2,2-dimethyl-6-trifluoromethyl-8-pyridono[5,6-g]quinoline: $^1$H NMR (400 MHz, DMSO-$d_6$) δ11.70 (s, 1H), 7.18 (s, 1H), 6.85 (s, 1H), 6.35 (s, 1H), 2.65 (t, J=6.6 Hz, 2H), 1.61 (t, J=6.6 Hz, 2H), 1.17 (s, 6H).

1,2,3,4-Tetrahydro-2,2-dimethyl-10-nitro-6-(trifluoromethyl)-8-pyridono[5,6-g]quinoline (Compound 125, structure 44 of Scheme X, where $R^1$=H, $R^2$=Me) and 1,2,3,4-Tetrahydro-2,2-dimethyl-7,10-dinitro-6-(trifluoromethyl)-8-pyridono[5,6-g]quinoline (Compound 126, structure 45 of Scheme X, where $R^1$=H, $R^2$=Me)

This compound was prepared in a manner similar to that described for Compound 124 (EXAMPLE 26) from 1,2,3,4-tetrahydro-2,2-dimethyl-6-trifluoromethyl-8-pyridono[5,6-g]quinoline (65 mg, 0.22 mmol) and fuming $HNO_3$ (26 mL, 0.66 mmol, 3.0 equiv) in conc. $H_2SO_4$ (1.4 mL) to afford 18 mg (24%) of Compound 125, an orange solid, and 19 mg (22%) of Compound 126, an orange solid. Data for Compound 125: $R_f$ 0.38 (11.5:1 $CH_2Cl_2$:MeOH); $^1$H NMR (400 MHz, $CDCl_3$) δ12.38 (broad s, 1H, C(O)NH), 9.67 (broad s, 1H, NH), 7.51 (s, 1 H, 5-H), 6.83 (s, 1H, 7-H), 2.93 (t, J=6.6 Hz, 2H, benzylic $CH_2$), 1.84 (t, J=6.6 Hz, 2H, 2×3-H), 1.44 (s, 6H, 2×($CH3$)2). Data for Compound 126: $R_f$ 0.24 (2:1 hexanes:EtOAc); $^1$H NMR (400 MHz, $CDCl_3$) δ12.85 (broad s, 1H, C(O)NH), 9.83 (broad s, 1H, NH), 7.53 (s, 1 H, 5-H), 2.96 (t, J=6.7 Hz, 2H, benzylic $CH_2$), 1.88 (t, J=6.7 Hz, 2H, 2×3-H), 1.47 (s, 6 H, 2×($CH3$)2).

EXAMPLE 28

(R/S)-4-Ethyl-1,2,3,4-tetrahydro-1-nitro-6-(trifluoromethyl)-8-pyridono[5,6-g]quinoline (Compound 127, structure 46 of Scheme X, where $R^1$=Et, $R^2$=H In a 15-mL r.b. flask, a mixture of (R/S)-4-ethyl-1,2,3,4-tetrahydro-6-(trifluoromethyl)-8-pyridono[5,6-g]quinoline (50.0 mg, 0.17 mmol) and $H_2SO_4$ (2.0 mL) was cooled to 2° C. Fuming $HNO_3$ (15.0 μL, 0.33 mmol, 2 equiv) diluted in $H_2SO_4$ (0.5 mL) was added over a period of 2.0 min, and stirred at 4° C. for 45 min, then poured into a mixture of ice (25 g) and $K_2CO_3$ (6.0 g). The aqueous layer was extracted with $CH_2Cl_2$ (2×25 mL), and the combined organic layers were washed with pH 7 phosphate buffer, dried ($MgSO_4$), filtered, and concentrated to a yellow solid. Purification by flash chromatography (2×15 cm column, $CH_2Cl_2$:EtOAc, 9:1) afforded 10.2 mg (18%) of Compound 127, an orange solid, and 8.1 mg (14%) of Compound 124, an orange solid, and. Data for Compound 127: $R_f$ 0.14 (9:1 $CH_2Cl_2$:EtOAc); $^1$H NMR (400 MHz, $CDCl_3$) δ12.32 (broad s, 1H, C(O)NH), 8.17 (s, 1H, 10-H), 7.66 (s, 1H, 5-H), 7.06 (s, 1H, 7-H), 4.09 (dt, J=15.0, 4.9 Hz, 1H, 2-H), 3.71 (ddd, J=15.5, 10.0, 6.1 Hz, 1H, 2-H), 2.85–2.92 (m, 1H, 4-H), 2.00–2.10 (m, 2H, 2×3-H), 1.63–1.72 (m, 1H, $CHCH_3$), 1.53–1.61 (m, 1H, $CHCH_3$), 1.02 (t, J=7.4 Hz, 3H).

Steroid Receptor Activity

Utilizing the "cis-trans" or "co-transfection" assay described by Evans et al., *Science*, 240:889–95 (May 13, 1988), the disclosure of which is herein incorporated by reference, the compounds of the present invention were tested and found to have strong, specific activity as both agonists, partial agonists and antagonists of AR. This assay is described in further detail in U.S. Pat. Nos. 4,981,784 and 5,071,773, the disclosures of which are incorporated herein by reference.

The co-transfection assay provides a method for identifying functional agonists and partial agonists which mimic, or antagonists which inhibit, the effect of native hormones, and quantifying their activity for responsive IR proteins. In this regard, the co-transfection assay mimics an in vivo system in the laboratory. Importantly, activity in the co-transfection assay correlates very well with known in vivo activity, such that the co-transfection assay functions as a qualitative and quantitative predictor of a tested compounds in vivo pharmacology. See, e.g., T. Berger et al. 41 *J. Steroid Biochem. Molec. Biol.* 773 (1992), the disclosure of which is herein incorporated by reference.

In the co-transfection assay, a cloned cDNA for an IR (e.g., human PR, AR or GR) under the control of a constitutive promoter (e.g., the SV 40 promoter) is introduced by transfection (a procedure to induce cells to take up foreign genes) into a background cell substantially devoid of endogenous IRs. This introduced gene directs the recipient cells to make the IR protein of interest. A second gene is also introduced (co-transfected) into the same cells in conjunction with the IR gene. This second gene, comprising the cDNA for a reporter protein, such as firefly luciferase (LUC), controlled by an appropriate hormone responsive promoter containing a hormone response element (HRE). This reporter plasmid functions as a reporter for the transcription-modulating activity of the target IR. Thus, the reporter acts as a surrogate for the products (mRNA then protein) normally expressed by a gene under control of the target receptor and its native hormone.

The co-transfection assay can detect small molecule agonists or antagonists of target IRs. Exposing the transfected cells to an agonist ligand compound increases reporter activity in the transfected cells. This activity can be conveniently measured, e.g., by increasing luciferase production, which reflects compound-dependent, IR-mediated increases in reporter transcription. To detect antagonists, the co-transfection assay is carried out in the presence of a constant concentration of an agonist to the target IR (e.g., progesterone for PR) known to induce a defined reporter signal. Increasing concentrations of a suspected antagonist will decrease the reporter signal (e.g., luciferase production). The co-transfection assay is therefore useful to detect both agonists and antagonists of specific IRs. Furthermore, it determines not only whether a compound interacts with a particular IR, but whether this interaction mimics (agonizes) or blocks (antagonizes) the effects of the native regulatory molecules on target gene expression, as well as the specificity and strength of this interaction.

The activity of selected steroid receptor modulator compounds of the present invention were evaluated utilizing the co-transfection assay, and in standard IR binding assays, according to the following illustrative Examples.

EXAMPLE 29

Co-transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine AR agonist and antagonist activity of the compounds of the present invention, the CV-1 cells were transiently transfected by calcium phosphate coprecipitation according to the procedure of Berger et al., 41 *J. Steroid Biochem. Mol. Biol.,* 733 (1992) with the following plasmids: pRShAR (5 ng/well), MTV-LUC reporter (100 ng/well), pRS-β-Gal (50 ng/well) and filler DNA (pGEM; 45 ng/well). The receptor plasmid, pRShAR, contains the human AR under constitutive control of the SV-40 promoter, as more fully described in J. A. Simental et al., "Transcriptional activation and nuclear targeting signals of the human androgen receptor"266 *J. Biol. Chem.,* 510 (1991).

The reporter plasmid, MTV-LUC, contains the cDNA for firefly luciferase (LUC) under control of the mouse mammary tumor virus (MTV) long terminal repeat, a conditional promoter containing an androgen response element. See e.g., Berger et al. supra. In addition, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing reference compounds (i.e. progesterone as a PR agonist, mifepristone ((11 beta,17beta)-11-[4-(dimethylamino)phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)phenyl]propanamide; Schering-Plough) as an AR antagonist; estradiol (Sigma) as an ER agonist and ICI 164,384 (N-butyl-3,17-dihydroxy-N-methyl-(7-alpha,17-beta)-estra-1,3,5(10)-triene-7-undecanamide; ICI Americas) as an ER antagonist; dexamethasone (Sigma) as a GR agonist and RU486 as a GR antagonist; and aldosterone (Sigma) as a MR agonist and spironolactone ((7-alpha-[acetylthio]-17-alpha-hydroxy-3-oxopregn-4-ene-21-carboxylic acid gamma-lactone; Sigma) as an MR antagonist) and/or the modulator compounds of the present invention in concentrations ranging from $10^{-12}$ to $10^{-5}$ M were added to the cells. Three to four replicates were used for each sample. Transfections and subsequent procedures were performed on a Biomek 1000 automated laboratory work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC response/β-Gal rate where β-Gal rate=β-Gal•$1\times10^{-5}$/β-Gal incubation time.

The mean and standard error of the mean (SEM) of the NR were calculated. Data was plotted as the response of the compound compared to the reference compounds over the range of the dose-response curve. For agonist experiments, the effective concentration that produced 50% of the maximum response ($EC_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of DHT as an AR agonist and progesterone as a PR agonist at the $EC_{50}$ concentration. The concentration of test compound that inhibited 50% of LUC expression induced by the reference agonist was quantified ($IC_{50}$). In addition, the efficacy of antagonists was determined as a function (%) of maximal inhibition.

IR Binding Assay

AR Binding: For the whole cell binding assay, COS-1 cells in 96-well microtiter plates containing DMEM-10% FBS were transfected as described above with the following plasmid DNA: pRShAR (2 ng/well), pRS-β-Gal (50 ng/well) and pGEM (48 ng/well). Six hours after transfection, media was removed, the cells were washed with PBS and fresh media was added. The next day, the media was changed to DMEM-serum free to remove any endogenous ligand that might be complexed with the receptor in the cells.

After 24 hours in serum-free media, either a saturation analysis to determine the $K_d$ for tritiated dihydrotestosterone ($^3$H-DHT) on human AR or a competitive binding assay to evaluate the ability of test compounds to compete with $^3$H-DHT for AR was performed. For the saturation analysis, media (DMEM-0.2% CA-FBS) containing $^3$H-DHT (in concentrations ranging from 12 nM to 0.24 nM) in the absence (total binding) or presence (non-specific binding) of a 100-fold molar excess of unlabeled DHT were added to the cells. For the competitive binding assay, media containing 1 nM $^3$H-DHT and test compounds in concentrations ranging from $10^{-10}$ to $10^{-6}$ M were added to the cells. Three replicates were used for each sample. After three hours at 37° C., an aliquot of the total binding media at each concentration of $^3$H-DHT was removed to estimate the amount of free $^3$H-DHT. The remaining media was removed, the cells were washed three times with PBS to remove unbound ligand, and cells were lysed with a Triton X-100-based buffer. The lysates were assayed for amount of bound $^3$H-DHT and β-Gal activity using a scintillation counter or spectrophotometer, respectively.

For the saturation analyses, the difference between the total binding and the nonspecific binding, normalized by the β-Gal rate, was defined as specific binding. The specific binding was evaluated by Scatchard analysis to determine the $K_d$ for $^3$H-DHT. See e.g., D. Rodbard, "Mathematics and statistics of ligand assays: an illustrated guide" In: J. Langon and J J. Clapp, eds., *Ligand Assay*, Masson Publishing U.S.A., Inc., New York, pp. 45–99, (1981), the disclosure of which is herein incorporated by reference. For the competition studies, the data was plotted as the amount of $^3$H-DHT (% of control in the absence of test compound) remaining over the range of the dose-response curve for a given compound. The concentration of test compound that inhibited 50% of the amount of $^3$H-DHT bound in the absence of competing ligand was quantified ($IC_{50}$) after log-logit transformation. The $K_i$ values were determined by application of the Cheng-Prusoff equation to the $IC_{50}$ values, where:

$$K_i = \frac{IC_{50}}{(1 + [^3\text{H-DHT}])/K_d \text{ for } ^3\text{H-DHT}}$$

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_i$ values were determined by application of the Cheng-Prusoff equation to the $IC_{50}$ values, the labeled ligand concentration and the $K_d$ of the labeled ligand.

The agonist, antagonist and binding activity assay results of selected androgen receptor modulator compounds of present invention and the standard reference compounds on AR, as well as the cross-reactivity of selected compounds on the PR, ER, MR and GR receptors, are shown in Tables 1–2 below. Efficacy is reported as the percent maximal response observed for each compound relative to the reference agonist and antagonist compounds indicated above. Also reported in Tables 1–2 for each compound is its antagonist potency or $IC_{50}$ (which is the concentration (nM), required to reduce the maximal response by 50%), its agonist potency or $EC_{50}$ (nM).

TABLE 1

Agonist, partial agonist, antagonist and binding activity of androgen receptor modulator compounds of present invention and the reference agonist compound, dihydrotestosterone (DHT), and reference antagonists compound, 2-hydroxyflutamide (Flut) and Casodex (Cas), on AR.

| Cmpd No. | AR Agonist CV-1 Cells[a] | | AR Antagonist CV-1 Cells[a] | | AR Binding[a] |
|---|---|---|---|---|---|
| | Efficacy (%) | Potency (nM) | Efficacy (%) | Potency (nM) | $K_i$ (nM) |
| 101 | na[b] | na | 86 ± 6 | 325 ± 68 | 169 ± 88* |
| 102 | na | na | 85 ± 1 | 193 ± 19 | 11 |
| 103 | na | na | 85 ± 2 | 27 ± 5 | 78 ± 13* |
| 104 | na | na | 85 ± 2 | 40 ± 9 | 93 ± 48 |
| 12 | na | na | 53 ± 16* | 2366 ± 215* | na |
| 13 | na | na | 84 ± 6 | 726 ± 84 | na |
| 105 | 39 ± 6 | 125 ± 28 | 39 ± 6 | 34 ± 14 | 21 ± 11 |
| 106 | na | na | 78 ± 3 | 52 ± 14 | 73 ± 37 |
| 107 | na | na | 83 ± 3 | 38 ± 10 | 110 ± 42* |
| 109 | 13 ± 8* | 36 ± 45* | 77 ± 4 | 15 ± 2 | 18 ± 7* |
| 111 | 16 ± 2 | 227 ± 59 | 53 ± 5 | 43 ± 8 | 12 |
| 112 | 21 ± 6 | 26 ± 15 | 42 ± 10 | 20 ± 1 | 61 ± 16 |
| 113 | 31 | 245 | 48 | 1251 | 10 |
| 114 | na | na | 90 ± 1 | 203 ± 66 | na |
| 115 | na | na | 87 ± 1 | 100 ± 16 | 107 |
| 116 | na | na | 20 | 1460 | na |
| 117 | na | na | 82 ± 1 | 394 ± 75 | na |
| 118 | na | na | 70 ± 2* | 482 ± 179* | 86 ± 29 |
| 119 | na | na | 40 ± 12 | 1573 ± 1053 | 74 ± 29* |
| 120 | 18 ± 3 | 171 ± 95 | 61 ± 5 | 17 ± 2 | 156 ± 24 |
| 121 | 72 ± 20 | 150 ± 39 | na | na | nt[c] |
| 122 | 100 ± 17 | 3 ± 0 | na | na | 7 ± 2* |
| 123 | 91 ± 17 | 31 ± 2 | na | na | 87 |
| 124 | 50 ± 1 | 202 ± 18 | na | na | na |
| 125 | na | na | 73 | 1335 | na |
| 126 | na | na | 44 ± 2* | 5242 ± 363* | na |
| 127 | 56 ± 12 | 85 ± 36 | na | na | 136 |
| LG120907 | na | na | 74 ± 2 | 27 ± 5 | 26 ± 2 |
| Flut | na | na | 83 ± 1 | 15 ± 2 | 27 ± 8 |
| Cas | na | na | 78 ± 3 | 157 ± 35 | 117 ± 35 |
| DHT | 100 ± 0 | 5 ± 1 | na | na | 3 ± 1 |

[a]Values with standard errors (SEM) represent the mean value of three or more separate experiments with triplicate determinations; values without standard deviation represent a single experiment, and values with * represent the mean value of two experiments with standard deviation.
[b]na = not active (i.e. efficacy of < 10 and potency of > 10,000)
[c]nt = not tested

TABLE 2

Overall agonist and antagonist potentcy of selected androgen receptor modulator compounds of present invention and the reference agonist and antagonist compounds shown in Table 1 on PR, AR, ER, GR and MR.

| Cmpd No. | PR Potency Agon (nM) | PR Potency Antag (nM) | AR Potency Agon (nM) | AR Potency Antag (nM) | ER Potency Agon (nM) | ER Potency Antag (nM) | GR Potency Antag (nM) | MR Potency Antag (nM) |
|---|---|---|---|---|---|---|---|---|
| 101 | na | na | na | 525 | na | na | na | na |
| 102 | na | 398 | na | 193 | na | na | na | na |
| 103 | na | 5938 | na | 27 | na | na | na | 1586 |
| 104 | na | 800 | na | 40 | nt | nt | nt | nt |
| 105 | na | 160 | 125 | 34 | na | 34 | na | 2256 |
| Prog | 4 | na | 436 | 32 | na | na | na | nt |
| RU486 | na | 0.1 | na | 12 | na | 1500 | 0.7 | 1100 |
| DHT | na | 1800 | 3 | na | 1700 | na | na | nt |
| Flut | na | 1900 | na | 15 | na | na | na | na |
| Estr | nt | nt | na | na | 7 | na | na | nt |
| ICI 164 | na | na | na | na | na | 160 | na | na |
| Spir | nt | 268 | nt | nt | na | na | 2000 | 25 | na = not active (i.e., efficacy of > 10 and potency of > 10,000); nt = not tested As can be seen in Tables 1 and 2, Compounds 109 and 112 are highly selective AR antagonists, while Compounds 105, 111 and 113 are mixed AR agonists/antagonists. Importantly, these AR Compounds show very little or no cross reactivity on other sex steroid receptors. In contrast, the known PR antagonist, RU486, shows strong cross reactivity on both GR and AR, showing essentially equal potency as both a PR and GR antagonist, and strong activity as an AR antagonist.

EXAMPLE 30

Mouse Renal Ornithine Decarboxylase (ODC) Activity as an in vivo Assay for Determining the Activity of AR Modulators Ornithine Decarboxylase (ODC) is the first rate-limiting enzyme for polyamine synthesis and catalyzes conversion of L-ornithine to putrescine, releasing $C_2$. It is a constitutive enzyme present in all cells and tissues. ODC concentration is very low in quiescent cells; but, as part of a growth response, it increases many-fold within hours of exposure to trophic stimuli, such as hormones, drugs, and growth factors. See G. Scalabrino, et al. "Polyamines and Mammalian Hormones", *Mol. Cell. Endocrinol.* 77:1–35, 1991.

This enzyme in the mouse kidney is specifically stimulated by androgens, but not by estrogen, progesterone or glucocorticoids. See O. A. Janne, et al. "Ornithine Decarboxylase mRNA in Mouse Kidney: A Low Abundancy Gene Product Regulated by Androgens with Rapid Kinetics", *Ann New York Academy of Sciences* 438:72–84, 1984 and J. F. Catterall, et al. "Regulation of Gene Expression by Androgens in Murine Kidney", *Rec. Prog. Hor. Res.* 42:71–109, 1986. Androgen induction of ODC activity and gene expression occurs rapidly, becoming maximally stimulated within 24 hr of a single dose of testosterone. Therefore, it was used as an acute assay to determine the androgen specific response of compounds, including compounds of the present invention, in vivo.

In this assay, castrated male ICR mice (~30 g, 5–6 week-old) were grouped in fours and treated for 1 or 3 days as follows:

1) Control vehicle
2) Testosterone propionate (TP) (0.01–1.0 mg/mouse or 0.3–30 mg/kg, s.c.)
3) TP (3 mg/kg, s.c.) plus a reference compound or a compound of the present invention (30–90 mg/kg, orally/s.c.) to demonstrate antagonist activity, or
4) A compound of the present invention alone (30–90 mg/kg, orally/s.c.) to demonstrate AR agonist activity The animals are sacrificed 24 hr after last dosing, and the pair of kidneys were collected and homogenized. The homogenates were centrifuged to get supernatant (cytosol), which was incubated with [$^3$H]ornithine for 1 hour. The activity of this enzyme was measured by a titrimetric analysis of the rate of [$^3$H]putrescine production. Results were expressed as femtomoles of [$^3$H]putrescine formed per mg of protein per hour. R. Djurhuus "Ornithine Decarboxylase (EC4.1.1.17) Assay Based Upon the Retention of Putrescine by a Strong Cation-Exchange Paper", *Anal. Biochem.* 113:352–355, 1981.

AR Agonist Mode

Testosterone propionate (TP) induced the ODC activity in a dose-dependent manner within the doses of 0.01 to 1.0 mg/mouse. Even at the highest dose used (1 mg/mouse), the induced ODC activity was not saturated, which was a 700-fold increase compared to castrated controls. Testosterone also showed similar stimulatory effects on ODC activities with less potency compared to TP (See Table 3). However, estradiol (0.02 mg/mouse) or progesterone (1 mg/mouse) did not show any stimulatory activity on this enzyme. The increase in ODC activity was accompanied by parallel, but lesser, changes in seminal vesicle weights. For example, TP (1.0 mg/mouse/day) resulted in a 700-fold increase in ODC activity, whereas increases in seminal vesicle weights were 4- to 5-fold.

TABLE 3

Androgenic Effects of Known Steroid compounds on Mouse Renal ODC activity (fold increase compared to castrated control).

| known compound | Doses (mg/mouse) | | | | |
|---|---|---|---|---|---|
| | 0.01 | 0.03 | 0.1 | 0.3 | 1.0 |
| Testosterone Propionate | | | | | |
| s.c. for 1 day | | | 9.7 | 21.9 | 26.4 |
| s.c. for 3 days | 1 | 10 | 173 | 414 | 707 |
| Testosterone s.c. for 3 days | | 1.5 | 2.3 | 17 | 135 |
| Estradiol s.c. for 1 day | 1.1 | | | | |
| Progesterone s.c. for 1 day | | | | | 1.1 |

AR Antagonist Mode

When testosterone propionate (0.1 mg/mouse) was used to induce the enzyme activity, the reference AR antagonists, flutamide, casodex and cyproterone acetate, inhibited this induction. Compounds of the present invention demonstrated AR antagonist activity in this assay model as shown in Table 4.

TABLE 4

Anti-Androgenic Effects on Mouse Renal ODC Activity

| Compound | Dose[a] (mg/mouse) | % Inhibition of ODC Activity[b] | | |
|---|---|---|---|---|
| | | 1 day s.c. | 1 day p.o. | 3 days p.o. |
| Flutamide | 1 | 88.3 | 37.7 | 60.7 |
| | 3 | 98.1 | | 92.0 |

TABLE 4-continued

Anti-Androgenic Effects on Mouse Renal ODC Activity

| | | % Inhibition of ODC Activity[b] | | |
|---|---|---|---|---|
| Compound | Dose[a] (mg/mouse) | 1 day s.c. | 1 day p.o. | 3 days p.o. |
| Casodex | 1 | nt | 97.0 | 98.9 |
| Cyproterone acetate | 1 | nt | 91.1 | 81.7 |
| 101 | 1 | nt | 31.7 | 26.2 |
| 102 | 1 | 25.4 | −5.2 | nt |
| 107 | 1 | 72 | 42 | nt |
| 120 | 1 | 52 | 46 | nt | a: the administration of all the compounds to castrated mice was combined with TP injection (0.1 mg/mouse/day, s.c.) for testing AR antagonists.
b: % inhibition of ODC activity induced by testosterone propionate (TP). Here, TP group is full induction and 0% inhibition; while, castrated group served as basal line, indicating 100% inhibition. Negative number indicates that the presented compound had no AR antagonist effects, while the ODC activity was certain percentage higher than TP-treated group.

Pharmacological and Other Applications

As will be discernible to those skilled in the art, the androgen receptor modulator compounds of the present invention can be readily utilized in pharmacological applications where AR antagonist or agonist activity is desired, and where it is desired to minimize cross reactivities with other steroid receptor related IRs. In vivo applications of the invention include administration of the disclosed compounds to mammalian subjects, and in particular to humans.

The following Example provides illustrative pharmaceutical composition formulations:

EXAMPLE 31

Hard gelatin capsules are prepared using the following ingredients:

| | Quantity (mg/capsule) |
|---|---|
| COMPOUND 101 | 140 |
| Starch, dried | 100 |
| Magnesium stearate | 10 |
| Total | 250 mg |

The above ingredients are mixed and filled into hard gelatin capsules in 250 mg quantities.

A tablet is prepared using the ingredients below:

| | Quantity (mg/tablet) |
|---|---|
| COMPOUND 101 | 140 |
| Cellulose, microcrystalline | 200 |
| Silicon dioxide, fume | 10 |
| Stearic acid | 10 |
| Total | 360 mg |

The components are blended and compressed to form tablets each weighing 360 mg.

Tablets, each containing 60 mg of active ingredient, are made as follows:

| | Quantity (mg/tablet) |
|---|---|
| COMPOUND 101 | 60 |
| Starch | 45 |
| Cellulose, microcrystalline | 35 |
| Polyvinylpyrrolidone (PVP) (as 10% solution in water) | 4 |
| Sodium carboxymethyl starch (SCMS) | 4.5 |
| Magnesium stearate | 0.5 |
| Talc | 1.0 |
| Total | 150 mg |

The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, and then added to the granules which, after mixing, are compressed on a tablet machine to yield tablets each weighing 150 mg.

Suppositories, each containing 225 mg of active ingredient, may be made as follows:

| | |
|---|---|
| COMPOUND 101 | 225 mg |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of normal 2g capacity and allowed to cool.

An intravenous formulation may be prepared as follows:

| | |
|---|---|
| COMPOUND 101 | 100 mg |
| Isotonic saline | 1,000 mL |
| Glycerol | 100 mL |

The compound is dissolved in the glycerol and then the solution is slowly diluted with isotonic saline. The solution of the above ingredients is then administered intravenously at a rate of 1 mL per minute to a patient.

EXAMPLE 32

The activity of selected compounds of the present invention as AR antagonists was *[] investigated in an immature castrated male rat model. A recognized test of the antiandrogen activity of a given compound, as described in L. G. Hershberger et al., 83 *Proc. Soc. Exptl. Biol. Med.*, 175 (1953); P. C. Walsh and R. F. Gines, "Inhibition of extratesticular stimuli to prostatic growth in the castrated rat by anti-androgens", 86 *Endocrinology*, 624 (1970); and B. J. Furr et al. "ICI 176334: a novel non-steroidal, peripherally selective antiandrogen", 113 *J. Endocrinology*, R7–9 (1987), was used with some modifications. In this modified protocol, we took advantage of the permeability of silicone rubber for steroids as described in P. J. Dziuk and B. Cook (1966)

"Passage of steroids through silicone rubber", Endocrinology 78:208–211, 1966, by implanting a silastic capsule containing testosterone to provide a continuous release of the steroid. Similar approaches have been used in the rat and in hamsters. See, respectively, D. A. Damarsa et al. "Negative feedback control of LH by testosterone: a quantitative study in male rats", *Endocrinology* 99:736–742, 1976, and A. W. Lucky et al., "Hair follicle response of the golden Syrian hamster flank organ to continuous testosterone stimulation using silastic capsules", *J. Invest. Dermatol.* 86:83–86, 1986, the disclosures of which are herein incorporated by reference.

The basis of this assay is the fact that male sexual accessory organs, such as the prostate and seminal vesicles, play an important role in reproductive function. These glands are stimulated to grow and are maintained in size and secretory function by the continued presence of serum testosterone (T), which is the major serum androgen (>95%) produced by the Leydig cells of the testis under the control of the pituitary luteinizing hormone (LH) and follicle-stimulating hormone (FSH). Testosterone is converted to the more active form, dihydrotestosterone (DHT), within the prostate by 5α-reductase. Adrenal androgens also contribute about 20% of total DHT in the rat prostate, and about 40% of that in 65-year old men. See F. Labrie et al., 16 *Clin. Invest. Med.* 475–492 (1993). However, this is not a major pathway since, in both animals and humans, castration without concomitant adrenalectomy leads to almost complete involution of the prostate and seminal vesicles. Therefore, under normal conditions, the adrenals do not support significant growth of prostatic tissue. See M. C. Luke and D. S. Coffey, "The Physiology of Reproduction" ed. by E. Knobil and J. D. Neill, 1, 1435–1487 (1994). Since the male sex organs are the tissues most responsive to modulation by androgen activity, this model is used to determine the androgen-dependent growth of the sex accessory organs in immature castrated rats.

Immature male rats (50–60 g, 21 day-old Sprague-Dawley, Harlan) were castrated under metofane anesthesia. Thereafter, most of the animals were subcutaneously implanted with a 10 mm silastic capsule containing crystalline testosterone, as described in P. J. Dziuk and B. Cook, supra. As a negative control, a group of castrated animals received empty 10 mm silastic implants. Animal groups were dosed for 3 days by oral gavage as follows:

1. Control vehicle (two groups, one with a 10 mm testosterone-containing silastic implant and the other with an empty silastic implant)
2. Flutamide and/or casodex (different doses, oral administration, daily), recognized antiandrogens, as reference compounds and/or a compound of the present invention (different doses, oral administration, daily) to demonstrate antagonist activity.

At the end of the 3-day treatment, the animals were sacrificed, and the ventral prostates and seminal vesicles were collected and weighed. Organ weight data were normalized to body weight of each animal and expressed as mg/100 g body weight. Results were analyzed by analysis of variance followed by the Dunnett's test. Data were transformed to comply with the normality and variance homogeneity criteria required to utilize the analysis of variance and Dunnett's test. The following data transformations were used for the ventral prostate and seminal vesicle: square root and power 0.7 respectively. Thereafter, the data were fitted to a four-parameter logistic equation and potencies derived from the fitted estimates. The same data transformations were used for the equation-fitting phase of the data analysis.

The gain and loss of sexual organ weights reflect the changes of cell number (DNA content) and cell mass (protein content), depending upon the serum androgen concentrations. See Y. Okuda, et al., 145 *J. Urol.,* 188–191 (1991), the disclosure of which is herein incorporated by reference. Therefore, measurement of organ wet weights is sufficient to indicate the bioactivity of androgens and androgen antagonists.

TABLE 5

Effects of reference AR antagonists flutamide and casodex of orchidectomized twenty-one day-old rats implanted with a 10 mm testosterone (T) silastic implant. Numbers enclosed within parentheses denote the number of animals per group.

| Treatment Group[a] | Flutamide | | Casodex | |
|---|---|---|---|---|
| | Ventral Prostate[c] | Seminal Vesicles[c] | Ventral Prostate[c] | Seminal Vesicles[c] |
| T + Vehicle | 80.6 ± 4.6 (5) | 31.8 ± 1.2 (5) | 84.4 ± 5.0 (5) | 30.8 ± 1.7 (5) |
| T + 0.1 mg/kg[a] | 78.9 ± 3.5 (5) | 31.1 ± 0.9 (5) | 76.9 ± 3.7 (5) | 31.6 ± 1.4 (5) |
| T + 1 mg/kg | 73.1 ± 4.6 (5) | 27.9 ± 2.5 (5) | 74.0 ± 6.7 (5) | 31.1 ± 0.8 (5) |
| T + 3 mg/kg | 62.4 ± 3.7 (5) | 22.7 ± 0.9 (5) | 65.8 ± 2.2 (5) | 27.0 ± 1.0 (5) |
| T + 10 mg/kg | 43.0 ± 3.6 (5) | 12.4 ± 1.8 (5) | 50.7 ± 0.9 (5) | 19.5 ± 1.2 (5) |
| T + 30 mg/kg | 28.4 ± 3.1 (5) | 9.1 ± 1.3 (5) | 37.4 ± 3.1 (5) | 12.0 ± 1.9 (5) |
| T + 100 mg/kg | 29.9 ± 1.8 (5) | 9.9 ± 0.4 (5) | 29.4 ± 1.8 (5) | 8.7 ± 1.0 (5) |
| Blank[b]/Vehicle | 28.0 ± 0.9 (5) | 8.0 ± 0.7 (5) | 30.7 ± 4.6 (5) | 6.7 ± 1.0 (5) |

[a]Indicates oral dosage of reference compound, either flutamide or casodex, indicated in the table.
[b]"Blank" refers to administration of an empty 10 mm silastic implant.
[c]Weight in mg/100 g body weight.

TABLE 6

Potency estimates ($ED_{50}$), 95% confidence limits, and inter-assay variabilities of the potency estimates for flutamide and casodex on ventral prostate and seminal vesicle weights, as a demonstration of AR antagonist activity for these reference compounds. The numbers enclosed within parentheses denote the number of independent experiments conducted with five animals per group.

| Standard Compound | Parameter | Potency ($ED_{50}$) Weighted Average ± SE (mg/kg) | 95% Confidence Limits | Inter-Assay Variability for Potency Estimate (% Coefficient of Variation) |
|---|---|---|---|---|
| Flutamide | Ventral Prostate Weight | 4.0 ± 0.6 (3) | 5.3–3.0 | 14.8% |
|  | Seminal Vesicle Weight | 3.3 ± 0.4 (3) | 4.1–2.6 | 11.8% |
| Casodex | Ventral Prostate Weight | 7.0 ± 0.9 (4) | 9.1–5.4 | 13.0% |
|  | Seminal Vesicle Weight | 7.8 ± 0.9 (4) | 9.8–6.2 | 11.8% |

As can be seen from Tables 5 and 6, this assay is a useful predictor of androgen antagonist activity, as reference compounds flutamide and casodex demonstrate a dose-dependent decrease in ventral prostate and seminal vesicle weights. This assay was used to demonstrate the utility of the compounds of the present invention (Tables 7 and 8).

TABLE 7

Effects of Compound 105 and 1,2,3,4-Tetrahydro-2,2-dimethyl-6-trifluoromethyl-8-pyridono[5,6-g]quinoline (LG120907) on ventral prostate and seminal vesicle weights of orchidectomized twenty-one day-old rats implanted with a 10 mm testosterone silastic implant. The numbers enclosed within parentheses denote the number of animals per group.

| Treatment Group[a] | Compound 105 Ventral Prostate[c] | Compound 105 Seminal Vesicle[c] | LG120907 Ventral Prostate[c] | LG120907 Seminal Vesicle[c] |
|---|---|---|---|---|
| T + Vehicle | 74.4 ± 1.3 (5) | 36.2 ± 2.1 (5) | 74.4 ± 1.3 (5) | 36.2 ± 2.1 (5) |
| T + 0.1 mg/kg[a] | 74.8 ± 5.4 (5) | 28.1 ± 3.6 (5) | 78.5 ± 2.0 (5) | 32.9 ± 1.2 (5) |
| T + 1 mg/kg | 63.6 ± 6.6 (5) | 27.4 ± 1.7 (5) | 57.3 ± 1.8 (5) | 28.9 ± 1.4 (5) |
| T + 3 mg/kg | 48.4 ± 6.6 (5) | 24.9 ± 0.9 (5) | 66.4 ± 5.6 (5) | 31.7 ± 2.9 (5) |
| T + 10 mg/kg | 40.0 ± 1.3 (5) | 15.2 ± 0.3 (5) | 59.9 ± 2.7 (5) | 28.2 ± 1.8 (5) |
| T + 30 mg/kg | 24.6 ± 2.0 (5) | 7.1 ± 1.4 (5) | 47.4 ± 2.9 (5) | 16.5 ± 0.8 (5) |
| T + 100 mg/kg | 23.6 ± 2.2 (5) | 7.6 ± 1.4 (5) | 20.2 ± 2.0 (5) | 10.4 ± 1.0 (5) |
| Blank[b]/Vehicle | 25.6 ± 2.3 (5) | 6.3 ± 0.7 (5) | 25.6 ± 2.3 (5) | 6.3 ± 0.7 (5) |

[a]Indicates the oral dosage of the compound indicated in the table.
[b]"Blank" refers to administration of an empty 10 mm silastic implant.
[c]Weight in mg/100 g body weight.

TABLE 8

Potency estimates ($ED_{50}$), 95% confidence limits, and inter-assay variabilities of the potency estimates for Compound 105 and LG120907 on ventral prostate and seminal vesicle weights. The numbers enclosed within parentheses denote the number of independent experiments conducted with five animals per group.

| Standard Compound | Parameter | Potency ($ED_{50}$) Weighted Average ± SE (mg/kg) | 95% Confidence Limits | Inter-Assay Variability for Potency Estimate (% Coefficient of Variation) |
|---|---|---|---|---|
| Compound 105 | Ventral Prostate Weight | 3.1 ± 0.7 (3) | 5.0–2.0 | 23.6% |
|  | Seminal Vesicle Weight | 7.5 ± 1.3 (3) | 10.6–5.3 | 17.5% |
| LG120907 | Ventral Prostate Weight | 18.3 ± 4.8 (2) | 30.5–11.0 | 26.1% |
|  | Seminal Vesicle Weight | 19.2 ± 2.8 (2) | 25.6–14.5 | 14.5% |

From Table 7, it can be seen that Compound 105 demonstrates greater anti-androgen activity on both rat ventral prostate and seminal vesicle weights. At a dose of 30 mg/kg, Compound 105 suppresses ventral prostate weight to castrate levels. A lower organ weight corresponds to greater anti-androgen activity. LG120907 is only partially efficacious at this dose, and requires a 100 mg/kg dose for suppression to castrate levels. This same trend is demonstrated on seminal vesicle weights, as the 30 mg/kg dose of Compound 105 results in complete suppression to castrate levels. However, even the 100 mg/kg dose of LG120907 does not bring the organ weight to castrate levels.

Table 8 shows the potency of the test compounds on ventral prostate and seminal vesicle weights as the weighted average from three separate experiments. The potency ($ED_{50}$) of Compound 105 is significantly greater on both the ventral prostate and seminal vesicles. The increased potency of Compound 105 on these sex accessory tissues is unanticipated based on its structure and in vitro data.

While in accordance with the patent statutes, description of the preferred embodiments and processing conditions have been provided, the scope of the invention is not to be limited thereto or thereby. Various modifications and alterations of the present invention will be apparent to those skilled in the art without departing from the scope and spirit of the present invention.

Consequently, for an understanding of the scope of the present invention, reference is made to the following claims.

What is claimed is:

1. A compound having the formula:

(I)

wherein:
- $R^1$ is hydrogen, F, Cl, Br, I, $NO_2$, $OR^{20}$, $NR^{21}R^{22}$, $SR^{20}$, $C_1–C_4$ alkyl or perhaloalkyl, where $R^{20}$, $R^{21}$ and $R^{22}$ are independently hydrogen, $C_1–C_6$ alkyl or perfluoroalkyl, aryl, or heteroaryl;
- $R^2$ is hydrogen, F, Br, Cl, $C_1–C_4$ alkyl or perhaloalkyl, aryl, or heteroary, $CF_3$, $CF_2H$, $CFH_2$, $CF_2OR^{20}$, $CH_2OR^{20}$, where $R^{20}$ has the same definition given above;
- $R^3$ is hydrogen, $C_1–C_4$ alkyl, F, Cl, Br, I, $OR^{20}$, $NR^{21}R^{22}$ or $SR^{20}$, where $R^{20}$ through $R^{22}$ have the definitions given above;
- $R^4$ and $R^5$ each independently are hydrogen, a $C_1–C_4$ alkyl or perfluoroalkyl, or $R^4$ and $R^5$ taken together can form a three- to seven-membered ring;
- $R^6$ and $R^7$ each independently are hydrogen, a $C_1–C_4$ alkyl or perfluoroalkyl;
- $R^8$ is hydrogen, a $C_1–C_{12}$ alkyl or perfluoroalkyl, hydroxymethyl, aryl, or heteroaryl;
- $R^9$ through $R^{18}$ each independently are hydrogen, a $C_1–C_4$ alkyl or perfluoroalkyl;
- $R^{24}$ is hydrogen, a $C_1–C_4$ alkyl, F, Cl, Br, I, NO2, $OR^{20}$, $NR^{21}R^{22}$ or $SR^{20}$, where $R^{20}$ through $R^{22}$ have the definitions given above;
- m is 1;
- n is 0 or 1;
- o is 0 or 1;
- Y is O or S;
- Z is O, S, NH, $NR^{22}$ or $NCOR^{22}$, where $R^{22}$ has the same definition given above, wherein the compound is an androgen receptor modulator.

2. A compound according to claim 1, wherein the compounds are androgen receptor antagonists.

3. A compound according to claim 1, wherein the compounds are androgen receptor agonists.

4. A compound according to claim 1, wherein the compounds are androgen receptor partial agonists.

5. A compound according to claim 1 selected from the group consisting of (R/S)-6,7,7a,11-tetrahydro-7a-methyl-4-trifluoromethyl-2-pyridono[5,6-g]pyrrolidino[1,2-a]quinoline; (R/S)-3-fluoro-6,7,7a,11-tetrahydro-7a-methyl-4-trifluoromethyl-2-pyridono[5,6-g]pyrrolidino[1,2-a]quinoline; (R/S)-6,7,7a,11-tetrahydro-1,7a-dimethyl-4-trifluoromethyl-2-pyridono[5,6-g]pyrrolidino[1,2-a]quinoline; and (R/S)-3-fluoro-6,7,7a,11-tetrahydro-1,7a-dimethyl-4-trifluoromethyl-2pyridono[5,6-g]-pyrrolidino[1,2-a]quinoline.

6. A pharmaceutical composition comprising a pharmaceutically effective amount of a compound of claim 1 and a pharmaceutically acceptable carrier.

7. A pharmaceutical composition according to claim 6, wherein the composition is formulated for oral, topical, intravenous, suppository or parental administration.

8. A pharmaceutical composition according to claim 6, wherein the compound is administered to a patient as a dosage unit at from about 1 µg/kg of body weight to about 500 mg/kg of body weight.

9. A pharmaceutical composition according to claim 1, wherein the compound is administered to a patient as a dosage unit at from about 10 µg/kg of body weight to about 250 mg/kg of body weight.

10. A pharmaceutical composition according to claim 6, wherein the compound is administered to a patient as a dosage unit at from about 20 µg/kg of body weight to about 100 mg/kg of body weight.

11. A pharmaceutical composition according to claim 6, wherein the composition is effective as an anabolic agent, for stimulation of hematopoiesis or in modulating a condition selected from the group of acne, male-pattern baldness, male hormone replacement therapy, wasting diseases, hirsutism, hypogonadism, prostatic hyperplasia, hormone-dependent cancers, prostate cancer and breast cancer.

12. A method of affecting androgen receptor activity comprising the in vivo administration of a composition according to claim 6.

13. A method of modulating a process mediated by androgen receptors comprising administering to a patient an effective amount of a composition according to claim 6.

14. A method of affecting androgen receptor activity comprising the in vivo administration of a compound according to claim 1.

15. A method of modulating a process mediated by androgen receptors comprising administering to a patient an effective amount of a compound according to claim 1.

16. A method of treating a patient according to claim 15, wherein the compound is effective as an anabolic agent, for stimulation of hematopoiesis or in modulating a condition selected from the group of acne, male-pattern baldness, male hormone replacement therapy, wasting diseases, hirsutism, hypogonadism, prostatic hyperplasia, hormone-dependent cancers, prostate cancer and breast cancer.

17. A method of treating a patient requiring androgen receptor therapy comprising administering to said patient an effective amount of a compound according to claim 1.

18. A method of treating a patient according to claim 17, wherein the compound is effective as an anabolic agent, for stimulation of hematopoiesis or in modulating a condition selected from the group of acne, male-pattern baldness, male hormone replacement therapy, wasting diseases, hirsutism, hypogonadism, prostatic hyperplasia, hormone-dependent cancers, prostate cancer and breast cancer.

* * * * *